(12) United States Patent
Frudakis

(10) Patent No.: US 7,110,885 B2
(45) Date of Patent: Sep. 19, 2006

(54) EFFICIENT METHODS AND APPARATUS FOR HIGH-THROUGHPUT PROCESSING OF GENE SEQUENCE DATA

(75) Inventor: Tony Nick Frudakis, Bradenton, FL (US)

(73) Assignee: DNAPrint genomics, Inc., Sarasota, FL (US)

(*) Notice: Subject to any disclaimer, the term of this patent is extended or adjusted under 35 U.S.C. 154(b) by 475 days.

(21) Appl. No.: 09/964,059

(22) Filed: Sep. 26, 2001

(65) Prior Publication Data

US 2003/0171875 A1 Sep. 11, 2003

Related U.S. Application Data

(60) Provisional application No. 60/274,686, filed on Mar. 8, 2001.

(51) Int. Cl.
G06F 19/00 (2006.01)

(52) U.S. Cl. .......................... 702/20; 702/19

(58) Field of Classification Search ................. 702/19, 702/20; 435/6
See application file for complete search history.

(56) References Cited

U.S. PATENT DOCUMENTS

| | | | |
|---|---|---|---|
| 5,580,728 A * | 12/1996 | Perlin | 435/6 |
| 5,655,019 A * | 8/1997 | McKernan et al. | 455/1 |
| 5,807,681 A * | 9/1998 | Giordano et al. | 435/6 |
| 5,840,484 A | 11/1998 | Seilhamer et al. | |
| 5,908,755 A | 6/1999 | Kumar et al. | |
| 5,953,727 A | 9/1999 | Maslyn et al. | |
| 5,966,712 A | 10/1999 | Sabatini et al. | |
| 5,970,500 A | 10/1999 | Sabatini | |
| 6,007,231 A * | 12/1999 | Vijg et al. | 702/20 |
| 6,023,659 A | 2/2000 | Seilhamer | |
| 6,068,977 A | 5/2000 | Perlin | |
| 6,074,831 A | 6/2000 | Yakhini et al. | |
| 6,094,626 A | 7/2000 | Kephart et al. | |
| 6,114,114 A | 9/2000 | Seilhamer et al. | |

(Continued)

FOREIGN PATENT DOCUMENTS

WO WO 99/05323 2/1999

(Continued)

OTHER PUBLICATIONS

Hwang et al., "Identification and Characterization of a New Member of the Placental Prolactin-Like Portein-C (PLP-C) Subfamily, PLP-Cbeta," Endocrinology, vol. 141, No. 9 (2000) pp. 3343-3352.*

Primary Examiner—Ardin H. Marschel
Assistant Examiner—Jerry Lin
(74) Attorney, Agent, or Firm—John J. Oskorep, Esq.

(57) ABSTRACT

One disclosed method of processing gene sequence data includes the steps of reading gene sequence data corresponding to a gene sequence and coding sequence data corresponding to a plurality of coding sequences within the gene sequence; identifying and storing, by following a set of primer selection rules, primer pair data within the gene sequence data for one of the coding sequences; repeating the acts of identifying and storing such that primer pair data are obtained for each sequence of the plurality of coding sequences; and simultaneously amplifying the plurality of coding sequences in gene sequences from three or more of individuals using the identified pairs of primer sequences. The set of primer selection rules include a rule specifying that all of the primer pair data for the plurality of coding sequences be obtained for a predetermined annealing temperature, which allows for the subsequent simultaneous amplification of sequences from hundreds of individuals in a single amplification run.

26 Claims, 4 Drawing Sheets

U.S. PATENT DOCUMENTS 6,317,507 B1 * 11/2001 Dolfing ............... 382/119
6,401,043 B1 *  6/2002 Stanton et al. ........... 702/20
6,470,277 B1 * 10/2002 Chin et al. ............ 702/19
6,475,736 B1 * 11/2002 Stanton, Jr. ............ 435/6

FOREIGN PATENT DOCUMENTS

WO    WO 00/18960    4/2000
WO    WO 00/56925    9/2000

* cited by examiner

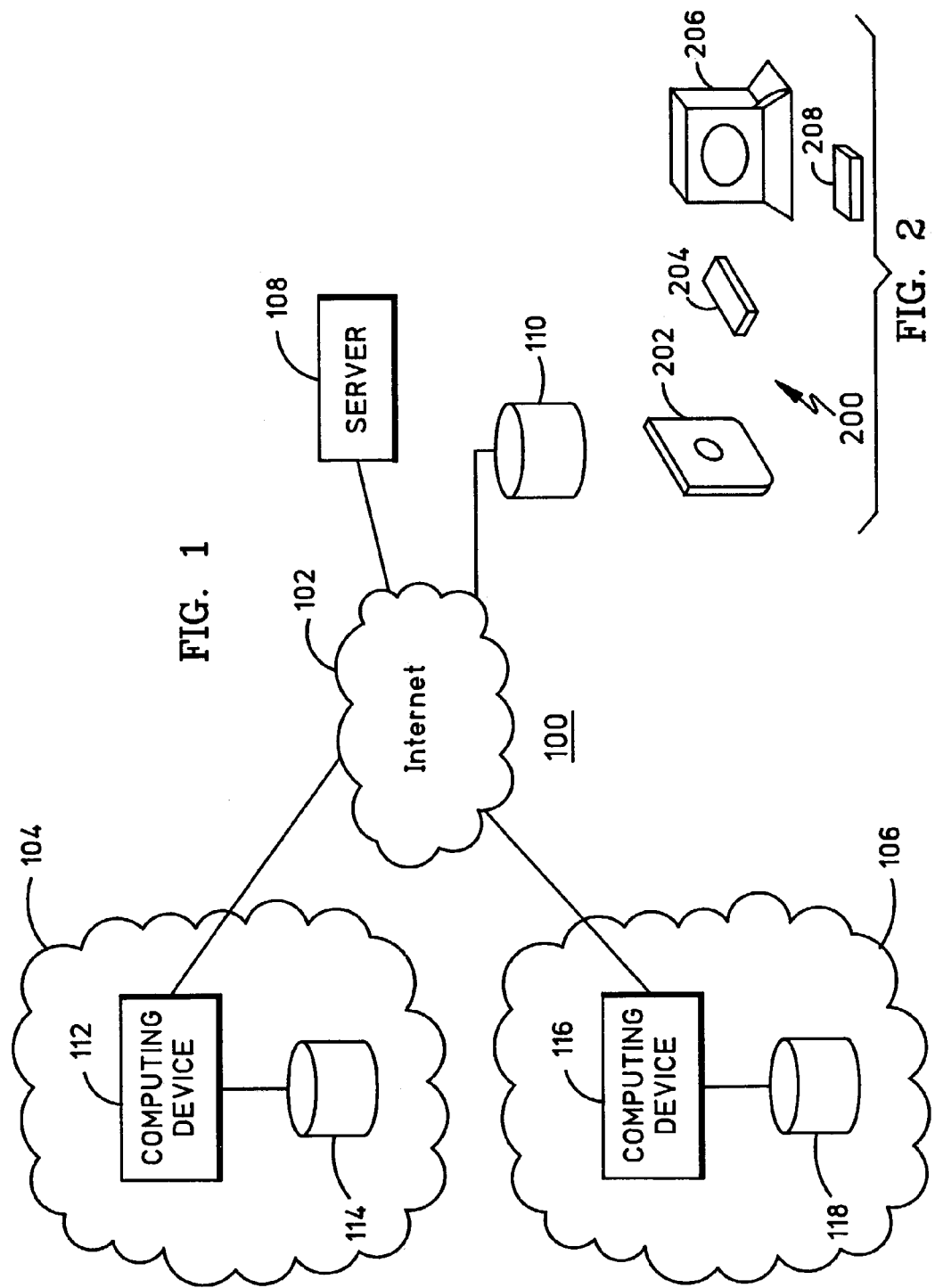

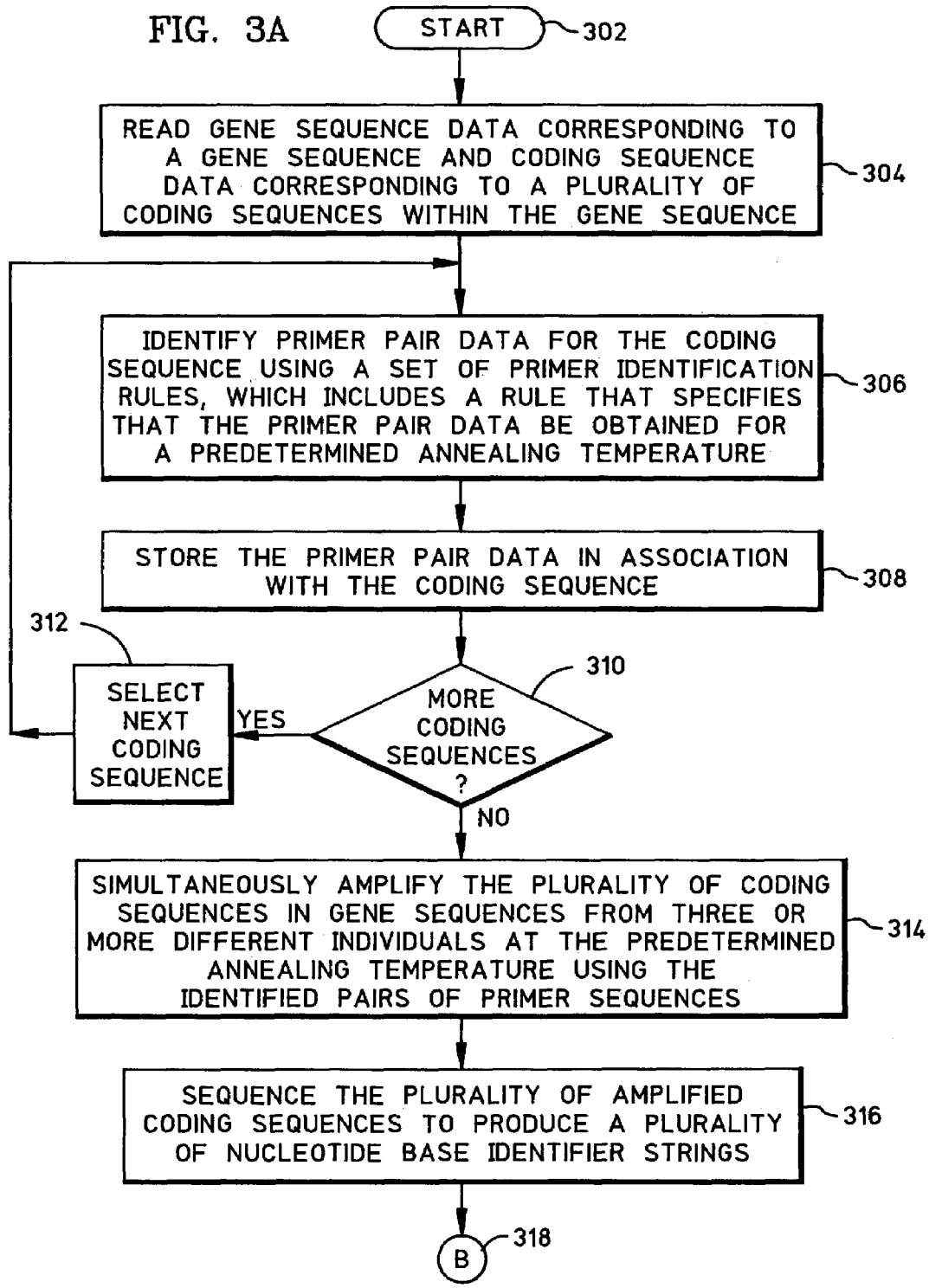

EFFICIENT METHODS AND APPARATUS FOR HIGH-THROUGHPUT PROCESSING OF GENE SEQUENCE DATA

This application claims benefit of the priority of U.S. Provisional Application Ser. No. 60/274,686 filed Mar. 8, 2001.

SEQUENCE LISTING

This patent hereby incorporates by reference a Sequence Listing on compact disc (CD) in accordance with 37 C.F.R. 1.821–1.825. More particularly, two CDs (one original and one duplicate copy) named DNAPRINT_SEQLIST have been submitted to the U.S.P.T.O., each of which includes the Sequence Listing in a file named "seq_listing" created on Dec. 23, 2002 and having a size of 57.1 KB.

BACKGROUND OF THE INVENTION

1. Field of the Invention

The present invention relates generally to the processing of gene sequence data with use of a computer, and more particularly to efficient high-throughput processing of gene sequence data to obtain reliable single nucleotide polymorphism (SNP) data and haplotype data.

2. Description of the Related Art

Bioinformatics is a field in which genes are analyzed with the use of software. A gene is an ordered sequence of nucleotides that is located at a particular position on a particular chromosome and encodes a specific functional product A gene could be several thousand nucleotide base pairs long and, although 99% of the sequences are identical between people, forces of nature continuously pressure the DNA to change.

From generation to generation, systematic processes tend to create genetic equilibria while genetic sampling or dispersive forces create genetic diversity. Through these forces, a variant or unusual change can become not so unusual—it will eventually find some equilibrium frequency in that population. This is a function of natural selection pressures, random genetic drift, and other variables. Over the course of time, this process happens many times and primary groups having a certain polymorphism (or "harmless" mutation) can give rise to secondary groups that have this polymorphism, and tertiary, and so on. Such a polymorphism may be referred to as a single nucleotide polymorphism or "SNP" (pronounced "snip"). Among individuals of different groups, the gene sequence of several thousand nucleotide base pairs long could be different at 5 or 10 positions, not just one.

Founder effects have had a strong influence on our modern day population structure. Since systematic processes, such as mutation and genetic drift, occur more frequently per generation than dispersive process, such as recombination, the combinations of polymorphisms in the gene sequence are fewer than what one would expect from random distributions of the polymorphic sequence among individuals. That is, gene sequence variants are not random distributions but are rather clustered into "haplotypes," which are strings of polymorphism that describe a multi-component variant of a given gene.

To illustrate, assume there are 10 positions of variation in a gene that is 2000 nucleotide bases long in a certain limited human population. The nucleotide base identifier letters (e.g., G, C, A, and T) can be read and analyzed, and given a "0" for a normal or common letter at the position and a "1" for an abnormal or uncommon letter. If this is done for ten people, for example, the following strings of sequence for the polymorphic positions might be obtained:

| Person 1:  | 1000100000 |
|---|---|
| Person 2:  | 0000000000 |
| Person 3:  | 1000100000 |
| Person 4:  | 1111100000 |
| Person 5:  | 0000000000 |
| Person 6:  | 0000000000 |
| Person 7:  | 1000100000 |
| Person 8:  | 1000100000 |
| Person 9:  | 0100000001 |
| Person 10: | 1000100100 |

This list is typical of that which would be found in nature. As shown above, the "1000100000" haplotype is present four times out of ten, the "0000000000" haplotype is present three times out of ten, and the "1000100100" haplotype is present one time out of ten. If this analysis is done for a large enough population, one could define all of the haplotypes in the population. The numbers would be far fewer than that expected from a multinominal probability distribution of allele combinations.

The field of bioinformatics has played an important role in the analysis and understanding of genes. The human genome database, for example, has many files of very long sequences that together constitute (at least a rough draft of) the human genome. This database was constructed from five donors and is rich in a horizontal sense from base one to base one billion. Unfortunately, however, little can be learned from this data about how people genetically differ from one another. Although some public or private databases contain gene sequence data from many different donors or even contain certain polymorphism data, these polymorphism data are unreliable. Such polymorphism data may identify SNPs that are not even SNPs at all, which may be due to the initial use of unreliable data and/or the lack of proper qualification of such data.

In order to discover new SNPs in genes, one must sequence DNA from hundreds of individuals for each of these genes. Typically, a sequence for a given person is about 500 letters long. By comparing the sequences from many different people, DNA base differences can be noticed in about 0.1%–1.0% of the positions, and these represent candidate SNPs that can be used in screens whose role is to determine the relationship between traits and gene "flavors" in the population. The technical problem inherent to this process of discovery is that more than 1.0% of the letters are different between people in actual experiments because of sequencing artifacts, unreliable data (caused by limitations in the sequencing chemistry, namely that the quality goes down as the sequence gets longer) or software errors.

For example, if the error rate is 3% and 500 people with 500 bases of sequence each are being screened, there are (0.03)(500)=15 sites of variation within the sequence. If the average frequency of each variant is 5%, and 500 people are being screened, there are (0.05)(0.03)(500)(500)=375 sequence discrepancies in the data set which represent letters that are potentially different in one person from other people. Finding the "good ones" or true SNPs in these 375 letters is a daunting task because each of them must be visually inspected for quality, or subject to software that measures this quality inefficiently.

Furthermore, one must first amplify regions of the human genome from many different people before comparing the sequences to one another. To amplify these regions, a map of a gene is drawn and addresses around the regions of the gene are isolated so that the parts of the gene can be read. These regions of the gene may be referred to as coding sequences and the addresses around these regions may be referred to as primer sequences. More specifically, a primer is a single-stranded oligonucleotide that binds, via complementary pairing, to DNA or RNA single-stranded molecules and serves for the priming of polymerases working on both DNA and RNA.

Conventional primer design programs that identify primer sequences have existed for years, but they are not suitable for efficient high-throughput data processing of genomic (very large) sequence data. Some examples of conventional primer design programs are Lasergene available from DNAStar Inc. and GenoMax available from Informax, Inc. Basically, conventional primer design programs pick the best primer pairs within a given sequence and provide many alternates from which the user selects to accomplish a particular objective.

Efficient high-throughput reliable methods are becoming critical for quickly obtaining and analyzing large amounts of genetic information for the development of new treatments and medicines. However, the conventional primer design programs are not equipped for high-throughput processing. For example, they cannot efficiently handle large sequences of data having multiple regions of interest and require a manual separation of larger design tasks into their component tasks. Such a manual method would be very time consuming for multiple regions of interest in one large sequence. The output data from these programs are also insufficient, as they bear a loose association to the actual positions provided with the input sequence. Finally, although it is important to obtain a large amount of data for accurate assessment, it is relatively expensive to perform amplification over several runs for a large number of sequences. In other words, one large amplification is less expensive to run than several smaller ones covering the same genetic region. Because there are constraints on the upper size limit, several economic and technical variables should be considered when designing such an experiment.

Accordingly, what are needed are methods and apparatus for use in efficient high-throughput processing of gene sequence data for obtaining reliable high-quality SNP and hapolotype data.

SUMMARY OF THE INVENTION

The present invention relates generally to the processing of gene sequence data with a computer, and more particularly to efficient high-throughput processing of gene sequence data for obtaining reliable single nucleotide polymorphism (SNP) data and haplotype data. One novel software-based method involves the use of special primer selection rules which operate on lengthy gene sequences, where each sequence has a plurality of coding regions located therein. Such a sequence may have, for example, 100,000 nucleotide bases and 20 identified coding regions.

The primer selection rules may include a rule specifying that all primer pairs associated with the plurality of coding regions be obtained for a single predetermined annealing temperature. This rule could allow for the subsequent simultaneous amplification of many sequences in a single amplification run at the same annealing temperature. The rule that provides for this advantageous specification requires that each primer sequence has a length that falls within one or more limited ranges of acceptable lengths, and that each primer has a similar G+C nucleotide base pair content The primer selection rules may also include a rule specifying that a single primer pair be identified for two or more coding regions if they are sufficiently close together. This rule also provides for efficiency as the single primer pair may be used for the amplification of two or more coding sequences. Yet even another rule specifies that no primer sequence be selected for that which exists in prestored gene family data. This rule is important since it avoids identifying primer pairs that may amplify sequences other than those desired.

The method includes the particular acts of reading gene sequence data corresponding to the gene sequence and coding sequence data corresponding to the plurality of coding sequences within the gene sequence; identifying and storing, by following the special primer selection rules, primer pair data within the gene sequence data for one of the coding sequences; repeating the acts of identifying and storing such that primer pair data are obtained for each sequence of the plurality of coding sequences; and simultaneously amplifying the plurality of coding sequences in gene sequences from three or more individuals at the predetermined annealing temperature using the identified pairs of primer sequences.

Reliable single nucleotide polymorphism (SNP) data and haplotype data are subsequently identified with use of these amplified sequences. More particularly, the method includes the additional steps of sequencing the plurality of amplified coding sequences to produce a plurality of nucleotide base identifier strings (which include, for example, nucleotide base identifiers represented by the letters G, A, T, and C); positionally aligning the plurality of nucleotide base identifier strings to produce a plurality of aligned nucleotide base identifier strings; and performing a comparison amongst aligned nucleotide base identifiers at each nucleotide base position.

At each nucleotide base position where a difference amongst aligned nucleotide base identifiers exists, the method includes the additional steps of reading nucleotide base quality information (for example, phred values) associated with the aligned nucleotide base identifiers where the difference exists; comparing the nucleotide base quality information with predetermined qualification data; visually displaying the nucleotide base quality information for acceptance or rejection; and if the nucleotide base quality information meets the predetermined qualification data and is accepted, providing and storing resulting data (SNP identification data) that identifies where the difference amongst the aligned base identifiers exists.

After providing and storing all of the resulting data that identifies where the differences exist, the method involves the following additional acts. For each aligned nucleotide base identifier at each nucleotide base position where a difference exists, the method involves the acts of comparing the nucleotide base identifier with a prestored nucleotide base identifier to identify whether the nucleotide base identifier is a variant; and providing and storing additional resulting data that identifies whether the nucleotide base identifier is a variant The providing and storing of such additional resulting data may involve providing and storing a binary value of '0' for those nucleotide base identifiers that are identified as variants and a binary value of '1' for those nucleotide base identifiers that are not. The accumulated additional resulting data identifies is haplotype identification data.

Advantageously, the methods described herein allow for high-throughput processing of gene sequence data that is quick, efficient, and provides for reliable output data.

BRIEF DESCRIPTION OF THE DRAWINGS

FIG. 1 is a block diagram of a computer system which embodies the present invention;

FIG. 2 is an illustration of software components which may embody or be used to implement the present invention; and FIGS. 3A–3C form a flowchart describing a method of efficient high-throughput processing of gene sequence data.

DETAILED DESCRIPTION OF THE PREFERRED EMBODIMENTS

Figure 3B:
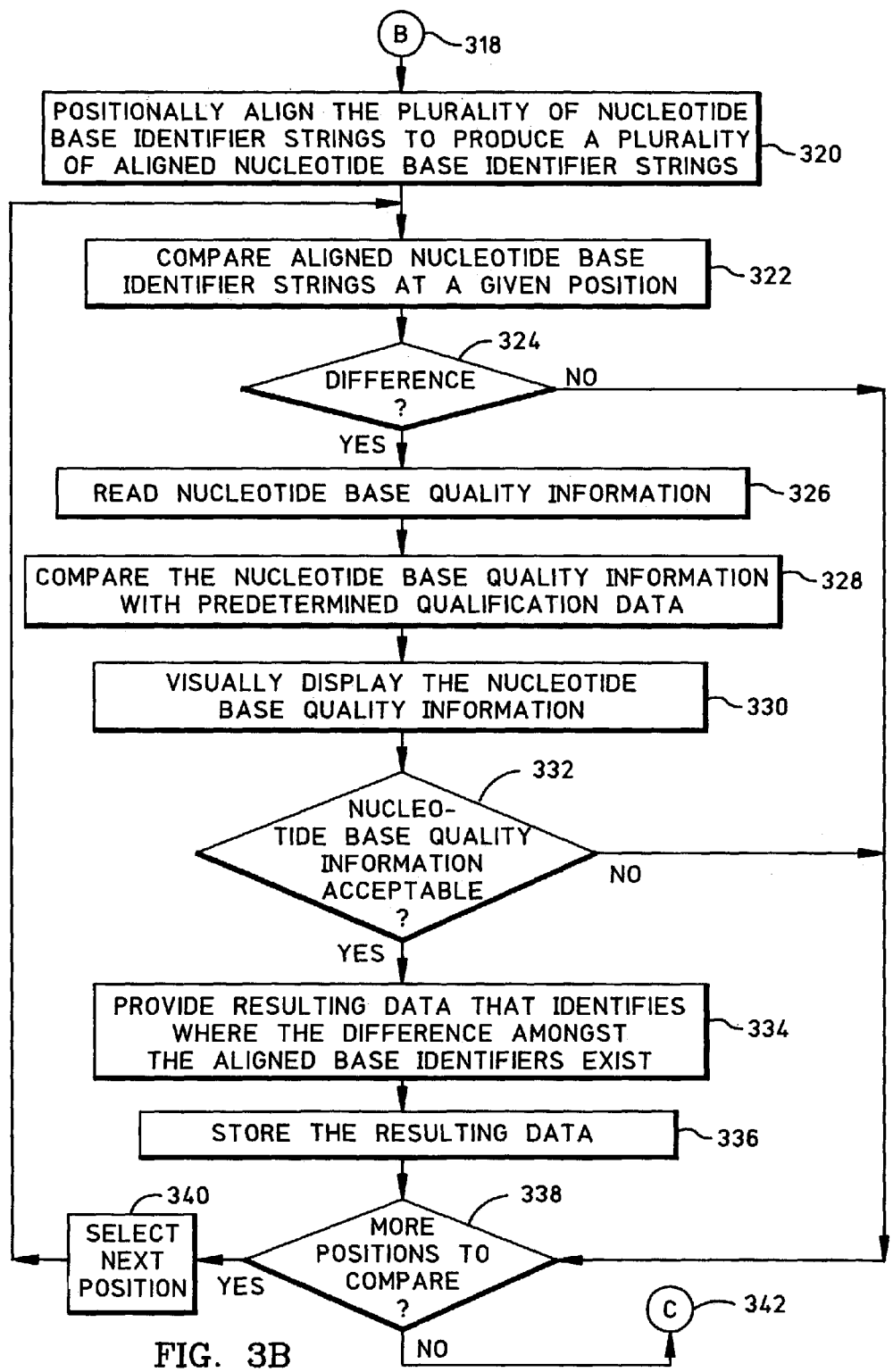

FIG. 1 is a block diagram of a computer system 100 which embodies the present invention. Computer system 100 includes a network 102 and computer networks 104 and 106. Network 102 is publicly accessible, and a server 108 and a database 110 which are coupled to network 102 are also publicly accessible. On the other hand, computer networks 104 and 106 are private. Each one of computer networks 104 and 106 include one or more computing devices and databases. For example, computer network 104 includes a computing device 112 and a database 114, and computer network 106 includes a computing device 116 and a database 118. The computing devices may include any suitable computing device, such as a personal computer (PC).

Network 102 may be the Internet, where an Internet Service Provider (ISP) is utilized for access to server 108 and database 110. Database 110 stores public domain gene sequence data. Also, the inventive software is preferably used in connection with and executed on computing device 112 of private network 104. Although a preferred computer system is shown and described in relation to FIG. 1, variations are not only possible, but numerous as one skilled in the art would readily understand. For example, in an alternative embodiment, network 102 may be an Intranet and database 110 a proprietary, private DNA sequence database.

The methods described herein may be embodied and implemented in connection with FIG. 1 using software components 200 shown in FIG. 2. The software may be embedded in or stored on a disk 202 or memory 204, and executable within a computer 206 or a processor 208. Thus, the inventive features may exist in a signal-bearing medium which embodies a program of machine-readable instructions executable by a processing apparatus which perform the methods.

Such software is preferably used in connection with and executed on computing device 112 of private network 104. Preferably, the system functions within the context of a PC network with a central Sun Enterprise server. The program can be loaded and run on any desktop PC that operates using the Linux or Unix operating system. Other versions could also function in a Windows environment Alternatively, the software could operate on a publicly accessible server and available for use through a public network such as the Internet.

Figure 3C:
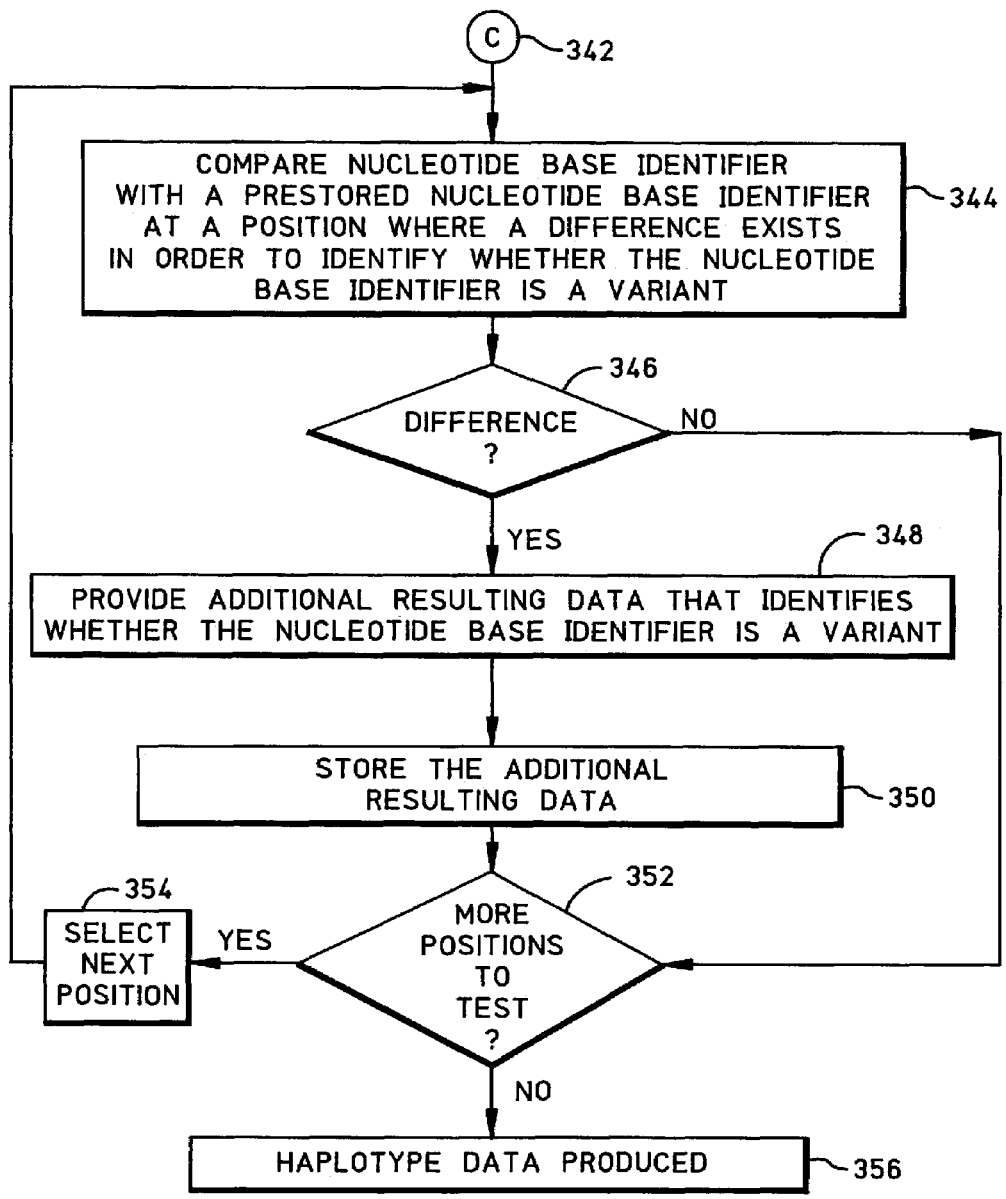

FIGS. 3A–3C form a flowchart which describes a method for efficient high-throughput processing of gene sequence data. This flowchart can be used in connection with software components 200 of FIG. 2 in the systems described in FIG. 1. Beginning at a start block 302 of FIG. 3A, gene sequence data corresponding to a gene sequence and coding sequence data corresponding to a plurality of coding sequences within the gene sequence are read (step 304). Next primer pair data within the gene sequence data are identified for one of the coding sequences by following a set of primer selection rules (step 306). The set of primer selection rules includes special rules for efficient, high-throughput processing.

For example, the primer selection rules may include a rule specifying that all primer pair data for the plurality of coding regions be obtained for a single predetermined annealing temperature (e.g., 62° Celsius). This rule allows for the subsequent simultaneous amplification of many sequences in a single amplification run at the predetermined annealing temperature. This primer selection rule further specifies that each primer sequence have a length that falls within one or more limited ranges of acceptable lengths. The primer selection rules may also include a rule specifying that a single primer pair be identified for two or more coding regions if they are sufficiently close together, which provides for efficiency as the single primer pair can be used for the amplification of two or more coding sequences. As yet another example, the primer selection rules may include a rule specifying that no primer sequence data be selected for that which exists in prestored gene family data, which is important since the program avoids selecting primer pairs that amplify sequences other than those intended.

Referring back to FIG. 3A, the primer pair data that were identified in step 306 are stored in association with the coding sequence (step 308), and may be displayed or outputted. If additional coding sequences need to be considered (step 310), the next coding sequence is selected (step 312) and steps 306 and 308 are repeated. Thus, the acts of identifying and storing are repeated such that primer pair data are obtained for each coding sequence within the gene sequence. Once all of the coding sequences have been considered at step 310, the primer sequences are used in the amplification process.

In particular, the plurality of coding sequences in gene sequences from three or more individuals (typically 100s of individuals) are simultaneously amplified in a gene amplification machine at the predetermined annealing temperature using the identified pairs of primer sequences (step 314). In the embodiment described, the predetermined annealing temperature is 62° Celsius, but in practice it may be any suitable temperature. Next, the plurality of amplified coding sequences are sequenced to produce a plurality of nucleotide base identifier strings (step 316). Each nucleotide base identifier string corresponds to a respective sequence of the plurality of amplified coding sequences. In the embodiment described, the nucleotide base identifiers are represented by the letters G, A, T, and C. The partial flowchart of FIG. 3A ends at a connector B 318, which connects with connector B 318 of FIG. 3B.

Single nucleotide polymorphism (SNP) data and haplotype data are subsequently identified with use of these amplified sequences. Beginning at connector B 318 of FIG. 3B, each string of the plurality of nucleotide base identifier strings is positionally aligned with the other to produce a plurality of aligned nucleotide base identifier strings (step 320). This may be performed with use of conventional Clustal functionality, which is described later below. Next, a comparison amongst aligned nucleotide base identifiers is performed at a given nucleotide base position (step 322).

If a difference amongst aligned nucleotide base identifiers exists (step 324), nucleotide base quality information associated with the aligned nucleotide base identifiers where the difference exists is read (step 326). This nucleotide base quality information may be, for example, phred values described later below. The nucleotide base quality information is then compared with predetermined qualification data (step 328). Next, the nucleotide base quality information is visually displayed for acceptance or rejection by the end-user (step 330). This step is important because phred values in themselves are not entirely adequate for determining quality. The reason is that phred uses a relative signal-to-noise ratio, but common sequence artifacts often show as signals having high ratios. If the nucleotide base quality information meets the predetermined qualification data and is accepted (step 332), resulting data (SNP identification data) that identifies where the difference amongst the aligned base identifiers exists is provided (step 334). This resulting data is stored (step 336).

If there are additional nucleotide base positions (step 338), the next nucleotide base position is considered (step 340) and steps 322–338 are repeated. Thus, steps 322–338 continue to execute until all of the differences amongst the aligned nucleotide base identifiers are identified. Step 338 is also executed if no difference exists at step 324, if the nucleotide base quality information is not acceptable at step 332, or if the user rejects the finding based on its visual appearance. The partial flowchart of FIG. 3B ends at a connector C 342, which connects with connector C 342 in FIG. 3C.

After providing and storing all resulting data that identify where differences amongst the aligned nucleotide base identifiers exist, additional acts are performed starting at connector C 342 of FIG. 3C. At a nucleotide base position where a difference exists, the nucleotide base identifier is compared with a prestored nucleotide base identifier in order to identify whether it is a variant (step 344). The prestored nucleotide base identifier is known from the stored data in step 336. This data could be stored as variant nucleotide bases or as encoded sites (for example major, minor).

Next, additional resulting data that identifies whether a given nucleotide base identifier is a variant is provided (step 348). This additional resulting data is stored (step 350) and may be displayed or outputted. Where differences do not exist amongst aligned nucleotide base identifiers, it is assumed that no variants exist Steps 348–350 may involve providing and storing a binary value of '0' for those nucleotide base identifiers that are identified as variants, and a binary value of '1' for those nucleotide base identifiers that are not. If additional nucleotide base positions need to be considered (step 352), then the next nucleotide base position is selected (step 354) and steps 344–352 are repeated. Step 352 is also executed if no difference is found at step 346. Thus, repeating of the acts occurs so that they are performed for each aligned nucleotide base identifier at each nucleotide base position where a difference exists. The repeating of steps ends when all nucleotide base positions have been considered at step 352. The combined additional resulting data provide haplotype identification data (step 356).

Additional Details Regarding Primer Sequence Selection and Amplification. Regarding steps 302–314 in FIG. 3A above, which may be referred to as the preamplification process, raw human genome data is used and the method basically draws little maps with the data. Additional details regarding the preamplification process will now be described.

Coding sequences are regions within a gene sequence that encode the protein of a gene. RNA is made from DNA only at these positions. When the RNA is turned into protein, the protein sequence is a translation of the DNA sequence at the coding region. The sequence between coding sequences is called intron, which is a DNA section that divides exons. Exons are the DNA segments that store information about the part of the amino acid sequence of the protein.

The object of the present invention is to survey the coding sequences at each coding region for a given gene in many different people, which is time consuming and expensive using conventional approaches. Therefore, a preamplification strategy is designed so that many sequences can be read in an efficient and inexpensive manner. Amplification uses two addresses, one in front of the region of interest and one behind it. These two addresses define sites where short pieces of DNA bind and are extended by an enzyme called thermus aquaticus (TAQ) polymerase. Preferably, a high fidelity TAQ variant would be used, such as Pfu polymerase. The two pieces of DNA together with the enzyme result in the amplification or geometric increase in the copy number of the sequence between the two addresses. After amplification, the software processes read and compare many sequences to one another to find out where people differ. Without amplification, there is too little DNA to read.

One object of the preamplification process is to appropriately select these addresses, which are the primer sequences, for each one of the coding regions. Ordinarily, this is not a trivial task. For any given coding region, there are typically large numbers of potential primer pair solutions from which to select, and often most of these would result in an inefficient or failed amplification because of non-specificity. The preamplification process described herein works in connection with a plurality of coding regions for many genes and identifies a plurality of primer regions so that amplification can be performed in a specific, cost-effective, and efficient manner.

The software program accepts as input (1) a genome database sequence file, which may be many hundreds of thousands of letters long and downloaded from the freely available human genome database (default format for convenience); (2) data (e.g., numbers) that indicate where the coding regions are in the input sequence file. The file containing the coding region data (taken from the annotation of a publicly accessible human genome data file) may be referred to as a "join" file because the data in this file typically resemble the following:

join(8982 . . 9313, 1 . . 81, 17131 . . 17389, 20010 . . 20169, 21754 . . 22353)/gene="CES1 AC020766"

OR join(81 . . 140,1149 . . 1320,1827 . . 2092,2402 . . 2548, 2648 . . 3089)/gene="example gene AC10003"

In the second-listed join file above, the first coding region indicated is the region from 81 to 140; the second coding region indicated is from 1149 to 1320, etc. The object is to select a small region of sequence (e.g., 18–22 letters) in front of and behind each coding region in the input sequence file for each coding region identified in the join file. These small sequences are the primers and, for each identified coding region, the program finds a flanking pair of primer sequences. These primer sequences are then named and presented to the user.

Using the two input files, the software is designed to more particularly perform the following in association with steps 302–314 of FIG. 3A:

(1) Use the numbers in the input join file to identify the coding regions in the input sequence file;

(2) Identify or select suitable primer regions around coding regions in the most efficient manner (e.g., sometimes the primers will flank a single coding region, and sometimes they will flank two or even three coding regions if they are close enough to be amplified efficiently);

(3) Select primer pairs for the same annealing temperature (i.e., the temperature required to get them to do their job during amplification). Thus, if one designs ten primer pairs all with the same annealing temperature, say 62° Celsius, they can all be used in an amplification machine together as each amplification run uses a single fixed temperature;

(4) Avoid ambiguous letters (e.g. the letter "n") when selecting primer regions;

(5) Design primers using a strategy to reduce the chance that the primer will be within what is called a "repeat" region. This strategy involves recognizing poly-A stretches, ensuring that the least amount of intron sequence possible is present between the two primers (as repeats tend to be removed from exon boundaries by buffer space);

(6) Display to the user all of the statistics surrounding the selections (as examples, how many letters exist between two primers of a pair, the precise numerical position of each of the selected primers, etc.); and (7) Output the primer sequences in a database compatible format (e.g., tab delimited) for easy ordering from primer synthesis vendors.

Now the following input join file join (81 . . 140)/gene="example gene AC10009"

and the following input sequence file

```
  1 GAATTCTTTC CAGAAGGCTT TCCATTTACT TTTCCTAGAT TCATCAGAAG AATCATTATC   SEQ ID NO: 1

61 TACAGCAGCT GTAACTGATT GAAATGTATT TTATGAACAA TAAGACTTGA AAGTTAAAAT

121 TGCTCCTTTA TCCATGTACT GAAGAATAAA TATTGTGAAA GCAGTCATAA AAACAGAAGT

181 AATCTTTTGG TACCTCTGCA TTAGAACTCT TTATTAACCA GGTGTATTGC CATTCAACAG

241 TAATATTTTG AAAGGAATCT CTATTTTTGA GCAGGTTTCA ACTTCTGCTT TTTATTTTAA

301 ACAGTAGACT TGAAATATTC AGTAACCATG CTATAAAGAG CTATGCTGTA AGACAGCTTT

361 TTCTATTTAT AGAGCATGGT TTTGAAATTA TAACAAAGCA TGGGTTTTAT CCTGAAATCA

421 TTCATAAATA ACACGTACCA AAACTTTAAT ACGGGCTAGC CAGTGTGAGC CAGTGTGACG
``` are considered. For the input sequence file, the number of the first letter of a line is shown at the beginning of each line and there are spaces every ten letters. Typically, there is an annotation before the sequence in the file, such as that shown below, which is ignored by the software:

Short sequences (e.g., between 18–22 letters) in front of and behind this coding region are selected based on a set of primer selection rules. The program then names these two primer sequences and presents them to the user at the end of the analysis. This is done seamlessly for multiple coding regions identified in the input join file. From the example

```
LOCUS       AL355303      157796 bp     DNA         HTG        08-SEP-2000
DEFINITION  Homo sapiens chromosome 10 clone RP11-445P17, *** SEQUENCING IN
            PROGRESS ***, 19 unordered pieces.
ACCESSION   AL355303
VERSION     AL355303.11  GI:10086110
KEYWORDS    HTG; HTGS_PHASE1; HTGS_DRAFT.
SOURCE      human.
```

The input join file identifies the coding region, which is underlined in the sequence below:

above, the following primer pair data (in small letters) are selected or designed for the given coding region:

```
  1 GAATTCTTTC CAGAAGGCTT TCCATTTACT TTTCCTAGAT TCATCAGAAG AATCATTATC   SEQ ID NO: 1

61 TACAGCAGCT GTAACTGATT GAAATGTATT TTATGAACAA TAAGACTTGA AAGTTAAAAT

121 TGCTCCTTTA TCCATGTACT GAAGAATAAA TATTGTGAAA GCAGTCATAA AAACAGAAGT

181 AATCTTTTGG TACCTCTGCA TTAGAACTCT TTATTAACCA GGTGTATTGC CATTCAACAG

241 TAATATTTTG AAAGGAATCT CTATTTTTGA GCAGGTTTCA ACTTCTGCTT TTTATTTTAA

301 ACAGTAGACT TGAAATATTC AGTAACCATG CTATAAAGAG CTATGCTGTA AGACAGCTTT

361 TTCTATTTAT AGAGCATGGT TTTGAAATTA TAACAAAGCA TGGGTTTTAT CCTGAAATCA

421 TTCATAAATA GCACGTACCA AGACTTGAAC ACGGGCTAGC CAGTGTGAGC CAGTGTGACG
```

```
  1 GAATTCTttc cagaaggctt tccatttacT TTTCCTAGAT TCATCAGAAG AATCATTATC  SEQ ID NO: 1

61 TACAGCAGCT GTAACTGATT GAAATGTATT TTATGAACAA TAAGACTTGA AAGTTAAAAT

121 TGCTCCTTTA TCCATGTACT GAAGAATAAA TATTGTGAAA GCAGTCATAA AAACAGAAGT

181 AATCTTTTGG TACCTCTGCA TTAGAACTCT TTATTAACCA GGTGTATTGC CATTCAACAG

241 TAATATTTTG AAAGGAATCT CTATTTTTGA GCAGGTTTCA ACTTCTGCTT TTTATTTTAA

301 ACAGTAGACT TGAAATATTC AGTAACCATG CTATAAAGAG CTATGCTGTA AGACAGCTTT

361 TTCTATTTAT AGAGCATGGT TTTGAAATTA TAACAAAGCA TGGGTTTTAT CCTGAAATCA

421 TTCATAAATa gcacgtacca agacttgaac ACGGGCTAGC CAGTGTGAGC CAGTGTGACG
```

Since there are typically about ten important regions in a given sequence, there are typically about twenty short primer sequences which are produced. Oftentimes, however, a single primer pair that flanks two (or more) coding regions is picked so that the actual total number of identified primer pairs will be less than two times the number of coding regions.

The two sequences are also named according to specific rules. Here, the names for the example as TPMTE2-5 and TPMTE2-3 are given. The two primer sequences are presented to the user in the output form below.

```
TPMTE2-5 ttccagaaggctttccatttac    SEQ ID NOs: 2–3

TPMTE2-3 gttcaagtcttggtacgtgct
```

Note that the TPMTE2-5 sequence is identical to the first picked sequence whereas the second sequence, TPMTE2-3, is the reverse and compliment of the second picked sequence.

In the preferred embodiment, the following set of primer selection rules are used for selecting primer sequences:

Rule 1: The number of combined "G"s and "C"s should be roughly equal the number of combined "A"s and "T"s.

Rule 2: There should be no longer than four consecutive "G"s together (e.g., . . . GGGG . . . ), four consecutive "C"s together, four consecutive "A"s together, and four consecutive "T"s together.

Rule 3: The length of each primer sequence should fall within the range of 18–22 (inclusive). The length is determined by giving a value of four for each "G", four for each "C", two for an "A", and two for a "T", and then calculating the sum of numbers such that the total sum for any selected sequence must equal 62. Thus, depending on the number of "G"s, "C"s, "T"s and "A"s, the total length of sequence necessary to get a value of 62 will usually fall within the range of 18 to 22 letters (inclusive).

Rule 4: The number of letters that fall in between the two selected sequences (herein referred to as a "block") should be equal to some rough integer multiple of 420 letters. For example, the number can be 420, 840, 1280, 1700, or 2120 (2120 is the maximum and 420 is the minimum). The number of letters does not need to be exactly 420, 840, or 1280, etc. however, but can be reasonably close; say plus or minus 50 or even 75. This range also can be chosen arbitrarily at first and then modified later. For example, if plus or minus 50 is chosen, the range should be 370–470, 790–890, or 1230–1330, etc.

Rule 5: At least one of the primer sequences must be within 100 letters of the beginning or the end of the coding region.

Rule 6: If the size of a block is larger than 1400, a third short sequence should be picked to reside roughly at position "700" in that block. This sequence should have the letters "seq" at the end of its name. For example, in the sequence below, the block is 2290 letters long:

```
  1 GAATTCTttc cagaaggctt tccatttacT TTTCCTAGAT TCATCAGAAG AATCATTATC  SEQ ID NOs: 4–5

61 TACAGCAGCT GTAACTGATT GAAATGTATT TTATGAACAA TAAGACTTGA AAGTTAAAAT

121 TGCTCCTTTA TCCATGTACT GAAGAATAAA TATTGTGAAA GCAGTCATAA AAACAGAAGT

181 AATCTTTTGG TACCTCTGCA TTAGAACTCT TTATTAACCA GGTGTATTGC CATTCAACAG

241 TAATATTTTG AAAGGAATCT CTATTTTTGA GCAGGTTTCA ACTTCTGCTT TTTATTTTAA

301 ACAGTAGACT TGAAATATTC AGTAACCATG CTATAAAGAG CTATGCTGTA AGACAGCTTT

361 TTCTATTTAT AGAGCATGGT TTTGAAATTA TAACAAAGCA TGGGTTTTAT CCTGAAATCA

421 TGCTCCTTTA TCCATGTACT GAAGAATAAA TATTGTGAAA GCAGTCATAA AAACAGAAGT

481 AATCTTTTgg tacctctgca ttagaactcT TTATTAACCA GGTGTATTGC CATTCAACAG

541 TAATATTTTG AAAGGAATCT CTATTTTTGA GCAGGTTTCA ACTTCTGCTT TTTATTTTAA

601 ACAGTAGACT TGAAATATTC AGTAACCATG CTATAAAGAG CTATGCTGTA AGACAGCTTT
```

-continued

```
 661 TTCTATTTAT AGAGCATGGT TTTGAAATTA TAACAAAGCA TGGGTTTTAT CCTGAAATCA

721 TGctcctttg tccatgtact gaagAATAAA TATTGTGAAA GCAGTCATAA AAACAGAAGT

. . . 1000 bases . . .

1781 AATCTTTTGG TACCTCTGCA TTAGAACTCT TTATTAACCA GGTGTATTGC CATTCAACAG

1841 TAATATTTTG AAAGGAATCT CTATTTTTGA GCAGGTTTCA ACTTCTGCTT TTTATTTTAA

1901 ACAGTAGACT TGAAATATTC AGTAACCATG CTATAAAGAG CTATGCTGTA AGACAGCTTT

1961 TTCTATTTAT AGAGCATGGT TTTGAAATTA TAACAAAGCA TGGGTTTTAT CCTGAAATCA

2021 TGCTCCTTTA TCCATGTACT GAAGAATAAA TATTGTGAAA GCAGTCATAA AAACAGAAGT

2081 AATCTTTTGG TACCTCTGCA TTAGAACTCT TTATTAACCA GGTGTATTGC CATTCAACAG

2141 TAATATTTTG AAAGGAATCT CTATTTTTGA GCAGGTTTCA ACTTCTGCTT TTTATTTTAA

2201 ACAGTAGACT TGAAATATTC AGTAACCATG CTATAAAGAG CTATGCTGTA AGACAGCTTT

2261 TTCATAAATa gcacgtacca agacttgaac
```

At the region around the letter at position "700", one cannot find a third short sequence that meets the criteria of having roughly equal G+C and A+T. A suitable sequence around position "723", however, can be found and is shown in lower case. In this example, three sequences are presented to the user: the first two read exactly as they appear in the lower case letters, and the last one being a reverse and compliment of the sequence at position "2270":

```
TPMTE2-5   ttccagaaggctttccatttac      SEQ ID NOs: 6-8

TPMTE2-seq ggtacctctgcattagaactc

TPMTE2-3   gttcaagtcttggtacgtgct
```

The following is a logic summary for the primer identification rules according to the preferred embodiment:

(1) Define the smallest block of sequence that surrounds and completely encompasses the coding region and is either 700 (+/-100) letters long, 1400 (+/-100) letters long, 2100 (+/-100) letters long, 2800 letters long (+/-200). That is, identify the smallest such block from those having a length=n*(700+/-100) for n={1, 2, 3, 4}.

(2) Find a sequence at the beginning of this block such that:
   (a) the sequence is 18–22 letters long;
   (b) the value of the sum of the letters is exactly 62, where a G=4, C=4, A=2 and T=2. Put another way, Sum (T)*2+Sum (A)*2+Sum (G)*4+Sum (C)*4=62. Using this rule, G+C will be either 9, 10, or 11 since only with these values is it possible to have a sequence that is 18–22 letters long with the sum of values=64;
   (c) No greater than four of the same consecutive letters must exist (e.g., . . . TTT . . . is fine but . . . GGGGG . . . is not) and, if a string of four letters exist in the "5" prime primer, the same string of four or three letters should not exist in the "3" prime primer; and
   (d) the last letter should be a "G" or a "C", not an "A" or a "T".

(3) Find a sequence following the end of the block such that the sequence follows the same rules as described in (2) above.

(4) After identifying two or more blocks, if two blocks can be constructed in the input sequence such that the end of one block overlaps with the beginning of another, or such that the end of one is within, say 100 letters of the beginning of another, the two blocks are merged, as long as the new merged block is not greater than 2800 (+/-200). It is preferable to have one large block compared to two or more smaller ones. If the blocks are merged, the first sequence selected for the first block and the last sequence selected for the second block forms the two sequences of the new merged block. The second sequence for the first block and the first sequence of the second block are discarded.

The selected sequences are also named by the software, preferably as follows. There are three parts to the name. The first is the gene which is the same as the input sequence file name. For example, for the gene "TPMT" all sequences the program finds for the input sequence file will have "TPMT" in the name. In addition, the first block found includes in its name "E1", the second block found includes in its name "E2", the third "E3", and so on. If two blocks are merged, however, both of these tags will be included in the name of the merged block in order. For example, if "E1" and "E2" blocks are merged, then the characters "E1E2" will be in the new name for the new merged block. Finally, the first sequence found for a block will have the characters "-5" and the second will have the characters "-3".

Below is a naming example where there are five blocks and two sequences for each block, except where blocks "2" and "3" were merged, and the merged block is 1260 (+/-100) letters long and required a third sequence to be selected:

```
TPMTE1-5
TPMTE1-3
TPMTE2E3-5
TPMTE2E3-3
TPMTE2E3SEQ
TPMTE4-5
TPMTE4-3
TPMTE5-5
TPMTE5-3
```

Another way to describe the naming process is presented. The 5-prime and the 3-prime primer may be presented to the user based on the following logic:

(1) The name of the gene (which is the sequence file name) and block appears in the name of each primer sequence;
(2) The gene and block name corresponding to the sequence file is provided in front of the name for a block is provided. If the sequence file is named "AHR", for example, the first block name would include "AHRE1" and the second block name would include "AHRE2";
(3) The "5" prime or "3" prime designation is also presented in the name of the primer. For example, the primers for the first block of the AHR gene would read:

AHRE1-5—the first sequence found (sequence whose numerical position is least—e.g. at position 60)
AHRE1-3—the second sequence found (sequence whose numerical position is most—e.g. at position 420)

After naming, the sequence of letters for each primer sequence may be presented as follows:

1. Present the first sequence (called the "5" primer) as it appears in the sequence, letter for letter but without the blank spaces;
2. Present the second sequence (called the "3" primer) such that
   a. The sequence is reversed such that the end is now the beginning and the beginning is now the end and then,
   b. "A" is substituted for each "T"
   c. "T" is substituted for each "A"
   d. "G" is substituted for each "C"
   e. "C" is substituted for each "G"
   (For example: "AATTATGCCT" would become "AGGCATAATT")
3. Present any third sequence for a block (if necessary because the block is 1260+/−100 letters long) as it appears in the input sequence exactly, letter for letter but without blank spaces.

An example output looks like:

```
TYRE15  TTGCATGTTGCAAATGATGTCC    SEQ ID NOs: 9–14

TYRE13  CAACCCAGGTCATCGTTCAC

TYRE25  CCTCTCAAGCACATTGATCAC

TYRE23  TATACTGATCTGAGCTGAGGC
``` and so on, until . . .

```
TYRE9-5  TAACATTCACACTAATGGCAGC

TYRE9-3  TGCTTCTCCTCTAGAGGCTG
```

The numerical position of each primer sequence relative to the input sequence is preferably presented as well.

The following is an example summary of a join file, a gene sequence file (including relevant portions only for brevity), and output data, for the gene "CES1 AC020766". In the gene sequence file below, the coding regions are highlighted in bold print.

```
================================================================
JOIN FILE FOR GENE "CES1 AC020766"

join(80513 . . . 81472, 81911 . . . 82007, 82114 . . . 82219, 85116 . . .
85265, 89595 . . . 89651)/gene ="
CES1 AC020766"
================================================================
SEQ ID NOs: 15–20
================================================================
GENE SEQUENCE FILE FOR "CES1 AC020766"

1  aacttagcaa acacatgatc ttgtatatag tagacatcat tattgttttc ccctctattc 61  ttcttttcaa tttctgaatc ataaggattg cctgagccta ggagatcaag gccagccttg 121  gcaacatggc gaaatgccat ctctacaaaa aaaaaaaaaa aaattatcta ggtgtggtgg 181  caagcaccag tggtcccagc tactcagaag gctgaggtgg gaggattgct tgagcccagg

*

*

*

28561  agtagagtgc tggcatactc agtaagacta tattgaataa atgaatgaat aaccccagaa 28621  taaaaatgta actataaatg tgttatccta ggtctcaaat cagaatgatc tgaaagttag 28681  gaaaccccc  tgccactgca gagatctcat cttactttta tgtcctatta taatgggaga 28741  ctatggcaag aaatttttga tatctacaga atagatctct atttggacca attttcatct 28801  ttgtttgatt caataaacag gctaagttct acttacgaag cctataaaac tccaaaactc 28861  caaatatcca catattccta aatatgtcac ctaactctaa tacatataca acatgatgag 28921  tacacatcct gtccattttc aagaacttat gcactcatca ctgtacacct tgatatctag

*

*

*
```

-continued

```
79801  agttaatgca cacagtttgg ctagttttgg cttcaaaatt aattaaactg tatcaatgta
79861  ttttgaagtg ttaagtcatc tgtatgcttt agctccttct atagatgagg caaatataca
79921  aacagattaa actgactttt acagaataat tattctttta ccttgtttac atggaaagga
79981  atcctccatt ttaggatgca cataaaatgc cagcctatgt tgatgacatt gccttaacac
80041  tttttttta agtaattta cagggtagtt aacctgtaaa agaaacagtg gataaacttg
80101  aaaatgctaa tagcaaaaaa cacttcagcc atggcacata caaccagaag ccaatgatat
80161  ccttcaacta tagaaattag cggtgttttc tgtttattcc tgaagcagga ttccatattc
80221  aagccagaaa ttgtcattca acagaaaaaa tcaggtcaaa acaatcaatc acataatgta
80281  gcaagacaaa agtatgtgct tatgtgaaga aaacaaaaa caacaaataa ccgaactttt
80341  attttcttga atataatatt gatggcaaga ttgctaagag gtcatccctg tatttagttt
80401  agataaaggc ttccagcata gaacactgtt aagaagtaac tgtcaggagc tatgcagaag
80461  tgatgagagg caaataaat aaaaactaga aaagcaggtt ttaattttct at<u>agacttta</u>
80521  <u>ttacacatta ttatgttacg agacaaatgc agataattct taatttatca aatttgtgag</u>
80581  <u>cttaattaac aaaaatattt gaccctcacc agaaaaacag ataactctaa atctactctg</u>
80641  <u>aaaatctaat caattgcgaa gtattaccta tttggagact atgtattata tcaaagataa</u>
80701  <u>agctactatt ctcacagaac atatggggtc attggcagcc aaccaataat gaagtaaata</u>
80761  <u>ttctaatatt tgggaaaata ctgagaaaac taataaattg tcctggatat tatttattct</u>
80821  <u>tgcctttaca aaagacttac acatccaaat gagattagtt tagaatagaa gttttagtt</u>
80881  <u>cagaaaatgt tcaaagtcca atacagtcat ggctaatcag agactagaga acctttataa</u>
80941  <u>aggtaagtag gcttgaaaac ccttggaaac tgagcagtct tattttgaac tagcatgttt</u>
81001  <u>taatcaaagg tatggaatta atcaaatatc aattaagaat tactggaatg cacactcatg</u>
81061  <u>ccaaatgaca actaacatgt tatttcctac tatgatgact ctttgatttg agtcagatgg</u>
81121  <u>cataaaaaaa tattgctagc tatacaataa attttactct tctgcttctg ctctctaaag</u>
81181  <u>aaaaatctta ttttttcaca taagaagctc atggaatcga atgttaatta agaaaagat</u>
81241  <u>agggtaagta caactggggg aaagacagta cctctaatta cataggaaat ccatgaaaga</u>
81301  <u>attaatcatc ataagagaag aatcattttt ccagtagccc cactaccatg aatgatattt</u>
81361  <u>tcatgagcct cggccacctt ctccaatgga tattgagaac ctatcacagg tttcaaccag</u>
81421  <u>ccaatttcca ttccagcttg aagggctgct gcatattgct gaaattcctc ctaagaaaag</u>
81481  gaaaaacaaa tttcttttg tagtgaaccg tatgatttaa ttttcagaag cattaaaaac
81541  acttcagaat ctaagtgtta taccatgaag agtctcttac aaatgtgtga cttttgtcaa
81601  cttgtccaga actatagaaa agtagttat ctacagggta accataaatc ccatctgcct
81661  gagacagtgt tagtgtacaa aatacctgtt gtcctgaaat tattactagt atcacatttc
81721  tatctcaaaa ggtatgctta cctggatata aattatactg tcaccctagt tgtccttctg
81781  gtgactaatc cttaccaact cccactagtc atataactaa gtttaacatc tattcaaact
81841  ttcagcttgc ctgagtaggc aaactgtacc aatgtttaag ttaccaaaat cagaagtact
81901  tctttcccta <u>ccttggttga ggaaaagaga gtaactccaa ttatactcga ctcctttgcc</u>
81961  <u>atggtgtctc gtgggtttat ttcaatagta cctctgctgc caacaaccta</u> acatgaaaaa
82021  cagcaattct acagttaaag attactgtaa aatagtgtta aattgtggta aaacattaaa
82081  gtggtaaaaa aaaaaaaag aaaggaata <u>cttactatca ctcgtcctcc atgtgacaga</u>
82141  <u>agactcaagt ctttactaag atttacatta gctaacattt caataattat atcaattcct</u>
```

-continued

```
82201  ttctcaccaa catacttcta tataataaaa gagaaatgta gagtaagata gcaagtgaaa
82261  aactgtaaaa tagctactat ctgtacaaga tattatagaa atatgtttca aatgatatat
82321  aaatgctaca tctttgagac taataatgca aaattttaaa taatctaatt atataatcac
82381  gatgtaattc caaggtacca gccagaacat ctaaactgat aaaaatttgt actaaataca
82441  ttgctgtagt gaaataaagt ttgtctggaa ttttcaggtg ctagactcaa cttgagtata
82501  aaatacttag ctgaaaattt tctatctgta aaataaactt tcataaagaa acaataaatc
82561  aaaagcccca aaccccagg gggctcccat ttttattaat aaacaaaaag caaagaaga
82621  tatcattagc tgttcggttt tgcatgattt ttgttgtttt agtgcatttg gttttgttct
82681  aaatggttta tcatctgttt gatgcactaa ctcttttggg ctcttggatg ttggacgctg
82741  gctcttacaa aaagctacac acatctacat tatattcatt ttattttaac acacacacac
82801  aaatgaatcc ctgtgcccgg gattgcacta ggtaccagga atacaaatac aaacataggg
82861  agctcaaaac aaaactagtg agaaagatgg gaaatactac agtcatagct ataaagtaat
82921  gggctaagta acacattagc agaaataaat catagaatac agagaaaaaa ggttaaggtt
82981  tgattgcctg ccatggtcag ataaagttcc acagagacga tgaactgggc cctcaggat
83041  gaataggagt ttcccaagcc aaaagaaagg aaaatgagta aggggaagct agacctgagg
83101  ctgagtcagt ctggaccaaa gaaacagaaa agcaaagatg gaggggactg agaacacaag

*

*

*

84301  taacgggcca tttttcatct ttgtgaatat tcttggataa tggtatcagc agtgctagat
84361  cttaggttcc ccagacgtat aacaaaggag tgcttttgtt cggcttttg gcaagatgat
84421  tgcaaaaaag gtaataaact ctcactctta tttttcctt catttgtaat gatctaattt
84481  acacagtact caatatttgg gaaattctaa tctccccaac gtgaggaagt ggttgaggat
84541  tagcaaagca ataagtgttt agcaaattgc taatatagta caagtgaaga acttcagaat
84601  ctgcttgaat tctgttaaat gcagcaacta aataaatgcc acctcaccat tttggatgca
84661  gtagtgatta ttcctccaaa gcatccagct aacaaatgaa ctttattccc tgggccacac
84721  agatccagtt tgtaatttac agatatctca ccttccatgg agaattcaca tcagtagaaa
84781  ttatattaag aatacctcac agctgcaaat acaaagctgc agctttactt agaatgttat
84841  ttgcattaaa aaatcaattt ttatagctct aagattctag agaagctata ttctatttaa
84901  tacacataaa caatacaaaa atgatagtaa agttttaaaa cttagacatc tgttttttaa
84961  ataaattaaa gttttaaaac acgcataaaa attcatcgca ctgaaaaaag gaagcaaaca
85021  gctttaaagg agtagttggt taaaaacata ttaaaaaacc acgcaagtct ccaaggaaca
85081  aagtttgact tttgtaaaac agtggaaaat tttaccttaa ttttatcaat gtaattcact
85141  tctctgtgat tgaacacttc atgggctcca ttttgcaaaa caatcttttg tccttcctca
85201  gtaccagcag tgcccaaaat ctttaagcca taagctctag caatttggca tgctgctaat
85261  ccaacctgaa aaacaaatat aacccaagag ttatatattc tctacactcc tgtaaacact
85321  taaatacata caatgaactt aagattccta taggcccac cctaacttta aggaacttaa
85381  gagtgtaaat gaagaaataa gaaaaacagc taactttaat tgagcattta aaatattcca
85441  ggaaccatac taaataattt ctacatattg ttttattcta tcctcacaat gaccctataa
85501  agtagatact attattgtcc ctattgtaca gataagaaag ttgaagcttc aaattataag
```

```
85561  taatttggcc aagtcatatg cggagatgga acaggagtt agaccagtct gactgcagaa
85621  cttgagtttt taaccactgc atcaagatgt ttgcagggtt taaagatgat cagaacatgc
85681  tctctgactt ctttgtgcat atgaaattct aaataacaaa tgtaaggcct ccaccattta
85741  agtagaagag ataggtatat gggcaaatta actaattcat ccatatggtg aatgtttata
85801  gagtgtttac gatgtgctag acatggtact taatgtaaga aataaactta tattctaagg
85861  gtggaggaag ataatagtca tatgaatgaa taaaataaat tcaggaaata aaagtgctaa
85921  gaaaaaataa gactggctgt tgggttaaag agacaggaat agggctatt taggtcatca
85981  ggaagagcca ctctgaaaaa atgagacctg aaaaaagtga ggaacaagcc acgagaacat
86041  ccggtcagcc acgtggagga tgctgtgggc atagtgaatg ccatggcta acctggcgag
86101  gtgggaatgc agttggggtc aaagaacaga aagagggca gtgtgtctca gggagggcg
86161  tgtacgaaag ggtcgaagat gaggccagaa aggccaagtc acacagaatc tgagggtga
86221  gggtagaggc ttccgagtat attaaaacct gtgcagaacc acgggagagc ttaagccagg
86281  aaatgatctg gttgactcag gctttaaaaa ggttgctcca attacatgtg aggcacaaag
86341  aaagcggtga ggaaaatggg aggaggaaga tcagtttgta gctgttagaa cagtctagat
86401  aagagatgaa gctggcttga acaaaggtgg tggcactgga aaaataaac aaattcagat
86461  atagtttaga ggtaagctaa tgggacttcc tcacagattg aatgcgggag atgaggaaaa
86521  gagaaaaata caggctgtct cctatgtctt tggccagatt aactgggtag agtgagaaga
86581  ctggagaaca ctaagtttgt gaaaatctcc agatttcact ttgccaagtg tggtggcgca
86641  tgcctgtaat cccagctatg tgggaggctg aggcaggagg atcgcttggg cccaggaatt
86701  tgaggagttt gggattgcag tgatcatgcc actgcactcc agtctgggca acggagcaag

*
                                *
                                *

88861  atccagtgac agagttcatg tggatttctt gttaaattct aactgcagag ctctaacttt
88921  tccctctaag ctcctgagag gcagattggc agctagtttc tcgaagaggt ttctgacagc
88981  cctgcattgg gtgatttcat tgaagggctt attttaagtt ctgagtcctc ctcccccatt
89041  cccccacatt agcattttca gccatgggtt gtggtgttaa ggacagggct gtatacgtgc
89101  actccatgga tgtcatcaaa gtgcagcagg caagcagcag aagggagata gaaggactaa
89161  gaattcacag tgtggcttta ccgtgctgtc tggggcaaca taggtaagct ttaatgagcc
89221  ttagtttcct tatctaaggg aatatggaat taatatcaac cttaaagaac tgtttaaaat
89281  tctaaataaa tatttttata acatatgcta cttgaaggca aaaacaaggc cagtttatct
89341  tagtctacac ccaatacagg tggaaaatct aacatatttt tgaaggggtg ctctgttgag
89401  tttattaacc aagaaatgct aaactaatga caaaacatca ccttcagaag accaaaatca
89461  aaagttttac tacataaaga aaaaaagcac ctttgactct atttataaat ctgacttta
89521  aaaatgacca aaggaactat aatgtgaaac ccataaaccc aagcttgttt caaatacat
89581  taaaaaaaat acttactcct ccacttgccc catgaaccag aacactctct ccagctttca
89641  cacaggcact gcaaaggaaa gcataagtta catcacctta ttttttgaag ctaattaatc
89701  tcgggtgttt tcatcatctt aaggaatttc taccccctagt ctggctaaca cttacacaaa
89761  cagcaaatgc aacctgacat acagccccaa atattcccta agctccacag aataaacaaa
89821  gccttcaatt catttattcc ttgaacaaat atttattggg agtctttatg ttccaggcac
```

-continued

```
89881  tatgctgctg acactggga tgactatgtg gtgctacttc tgagtggcta cagtccttgt
89941  gggttgtgaa gtaaaattgc tgagcctgga ggatctggaa tctctcattc ccatatatcc
90001  cccacagaaa gggcctcaaa gcaggtttat tatatagctc agtctttatt ctgtggtcta
90061  gagtaatgtc caagtaaaca cagtagctat ttttttttgcc caaggaaaga aagaaatttt
90121  tcttctccat gtctctgaac atcaggttgc accagccttg tactctttca gggaggaatg
90181  ctgagttagc aaaggtcaga gagtaggaaa tgcaataaat tctatcacaa agattcccat
90241  gtcatccccc tgaaatgtcc agattctctg gtgaaatggc attttctttt tacttccagt
90301  tcacatgact acttttctag tatgtactga aaagaaggga catgcagcaa ggcatgaggg
90361  gatgcctcac tattccagat ggacggtgcc aatgtcaaaa gccagcagat gctgtgagat
90421  ccagatctga ctctcaggaa ggctctctta cttcctcaaa caatgtgggg tggccacact
90481  gcagagacat tatagaacat tatgctccac ctgggaaaga gaacagtaac cagagtcctg
90541  ctcccagcta tgcaccaaca gctgagaagt ggcaacaatg agcaataagt gaagctttct
90601  cccacactct tgcttagagc tgaagggact gaggacaata tgttaaagta aaacataaac
90661  ataagggat aggatgacta gtgttaaact atgggatatg aaatacctcc caaagaaatt
90721  tttcaaaaat tcttataaga tgcccctcaa acactaaaga cacattctca taaatccctg
90781  gggcctgggg tgaggggaga aaaagcaggc aaatcccctc ctgaatcctt gcacagagtc
90841  gctgtgacag ttaattttat gtgtcaactt gactgggcca aggaacccaa tatttgttcc
90901  aacattactc tgttacagaa acagtgtttt ttttttttttt cgaatgagat taacaatgga
90961  atagctggat tttgagtaaa gcagatgacc ctctagaatg tgggtgggcc tcatccaatc
91021  agttgaaggc ttttgttttc aaagactgac ctccgatgag caagagtaaa ttcagccagc
91081  aaactttcta tggacttaaa ctgcacctct tccttgtgtc tcccatctgc tggcccaccg
91141  caacagattt tagactcacc agtcctccac aatttcatgg gtcaactctt taaaatcaat
91201  caatctgtgt gcgcgtgtgt gtgtgtgtgt gtgtatgtgt acagagtgac tgattcttaa
91261  ggaatttata tagagataaa tgatagatca gatcaaatag aagatcaaat agatagatga
91321  ttgactgata gatagacaga cagacacaca tcccgttgtt tgtttctctg gagaaccctg

*
                                    *
                                    *

147841 acagacagag atagacagag gcagagtcag ggagaggcag agaaagaaag agaacaagaa
147901 agcttaaaga tagtccaaac gcaaagctgt ctttaaaaaa tgcatactct attactggca
147961 acaaagtttt ataatctata cattttatga accactaatc cttaatttat tcaagatcac
148021 aacagggac tcatattata gagtcaagta aatatcatta ccaacatttt atttaacagt
148081 ttgtcctcct taattacatg gagaatgata tagtgactcc ttcatgcctt tttttctcct
148141 taacaagcca tatgcaggaa agtttccatg ctgcgcaaac ataaagaaa gttatatttc
148201 attcctaana gaaaactgaa aagc
```

```
================================================================
SEQ ID NOs: 21-40
================================================================

OUTPUT FROM PROGRAM

NUMBER OF JOINS    4

1. 80513 . . . 81472
2. 81911 . . . 82219
3. 85116 . . . 85265
4. 89595 . . . 89651

JOIN NUMBER ----- 1
  Length of pair 959
   Starting position of block   79813
   Block length (700 + pairlength + 800)    2459
Block . . .
agtttggctagttttggcttcaaaattaattaaactgtatcaatgtattttgaagtgttaagtcatctgtatgcttt agctccttctatagatgaggcaaatatacaaacagattaaactgactttttacagaataattattcttttaccttgtt tacatggaaaggaatcctccatttttaggatgcacataaaatgccagcctatgttgatgacattgccttaacactttt tttttaagtaattttacaggggtagttaacctgtaaaagaaacagtggataaacttgaaaatgctaatagcaaaaaac acttcagccatggcacatacaaccagaagccaatgatatccttcaactatagaaattagcggtgttttctgtttatt cctgaagcaggattccatattcaagccagaaattgtcattcaacagaaaaaatcaggtcaaaacaatcaatcacata atgtagcaagacaaaagtatgtgcttatgtgaagaaaaacaaaaacaacaaataaccgaacttttatttttcttgaat ataatattgatggcaagattgctaagaggtcatccctgtatttagtttagataaaggcttccagcatagaacactgt taagaagtaactgtcaggagctatgcagaagtgatgagaggcaaataatataaaaactagaaaagcaggttttaatt ttctatagactttattacacattattatgttacgagacaaatgcagataattcttaatttatcaaatttgtgagctt aattaacaaaaatatttgaccctcaccagaaaaacagataactctaaatctactctgaaaatctaatcaattgcgaa gtattacctatttggagactatgtattatatcaaagataaagctactattctcacagaacatatgggtgcattggca gccaaccaataatgaagtaaatattctaatatttgggaaaatactgagaaaactaataaattgtcctggatattatt tattcttgcctttacaaaagacttacacatccaaatgagattagtttagaatagaggtttttagttcagaaaatgtt caaagtccaatacagtcatggctaatcagagactagagaacctttataaaggtaagtaggcttgaaaacccttggaa actgagcagtcttattttgaactagcatgttttaatcaaaggtatggaattaatcaaatatcaattaagaattactg gaatgcacactcatgccaaatgacaactaacatgttatttcctactatgatgactctttgatttgagtcagatggca taaaaaatattgctagctatacaataaattttactcttctgcttctgctctctaaagaaaaatcttattttttcac ataagaagctcatggaatcgaatgttaattaaagaaaagatagggtaagtacaactgggggaaagacagtacctcta attacataggaaatccatgaaagaattaatcatcataagagaagaatcattttttccagtagccccactaccatgaat gatattttcatgagcctcggccaccttctccaatggatattgagaacctatcacaggtttcaaccagccaatttcca ttccagcttgaagggctgctgcatattgctgaaattcctcctaagaaaaggaaaaacaaatttcttttttgtagtgaa ccgtatgatttaattttcagaagcattaaaaacacttcagaatctaagtgttataccatgaagagtctcttacaaat gtgtgacttttgtcaacttgtccagaactatagaaaaagtagttatctacagggtaaccataaatcccatctgcctg agacagtgttagtgtacaaaatacctgttgtcctgaaattattactagtatcacatttctatctcaaaaggtatgct tacctggatataaattatactgtcaccctagttgtccttctggtgactaatccttaccaactcccactagtcatata actaagtttaacatctattcaaactttcagcttgcctgagtaggcaaactgtaccaatgtttaagttaccaaaatca gaagtacttcttttcctaccttggttgaggaaaagagagtaactccaattatactcgactcctttgccatggtgtct cgtgggtttatttcaatagtacctctgctgccaacaacctaacatgaaaaacagcaattctacagttaaagattact gtaaaatagtgttaaattgtggtaaaacattaaagtggtaaaaaaaaaaaaaagaaaaggaatacttactatcactc
```

```
gtcctccatgtgacagaagactcaagtctttactaagatttacattagctaacatttcaataattatatcaattcct ttctcaccaacatacttctatataataaaagagaaatgtagagtaagatagcaagtgaaaaactgtaaaatag□
```

```
Actual comp position    80450    sequence    tatgcagaagtgatgagaggc
Reverse comp position   80450    sequence    gcctctcatcacttctgcata
 g c t a  toalno  totalvalue 8    2  4  7  21  62

Actual comp position    81019    sequence    tactggaatgcacactcatgc
Reverse comp position  81019     sequence    gcatgagtgtgcattccagta
 g c t a  toalno  totalvalue 4    6  5  6  21  62

JOIN NUMBER ----- 2
   Length of pair 308
   Starting position of block    81211
    Block length (700 + pairlength + 800)    1808
Block . . .
```

```
tggaatcgaatgttaattaaagaaaagatagggtaagtacaactgggggaaagacagtacctctaattacataggaa atccatgaaagaattaatcatcataagagaagaatcattttttccagtagccccactaccatgaatgatattttcatg agcctcggccaccttctccaatggatattgagaacctatcacaggtttcaaccagccaatttccattccagcttgaa gggctgctgcatattgctgaaattcctcctaagaaaaggaaaaacaaatttcttttttgtagtgaaccgtatgattta attttcagaagcattaaaaacacttcagaatctaagtgttataccatgaagagtctcttacaaatgtgtgacttttg tcaacttgtccagaactatagaaaaagtagttatctacagggtaaccataaatcccatctgcctgagacagtgttag tgtacaaaatacctgttgtcctgaaattattactagtatcacatttctatctcaaaaggtatgcttacctggatata aattatactgtcaccctagttgtccttctggtgactaatccttaccaactcccactagtcatataactaagtttaac atctattcaaactttcagcttgcctgagtaggcaaactgtaccaatgtttaagttaccaaaatcagaagtacttctt ttcctaccttggttgaggaaaagagagtaactccaattatactcgactcctttgccatggtgtctcgtgggtttatt tcaatagtacctctgctgccaacaacctaacatgaaaaacagcaattctacagttaaagattactgtaaaatagtgt taaattgtggtaaaacattaaagtggtaaaaaaaaaaaaagaaaaggaatacttactatcactcgtcctccatgtg acagaagactcaagtctttactaagatttacattagctaacatttcaataattatatcaattcctttctcaccaaca tacttctatataataaaagagaaatgtagagtaagatagcaagtgaaaaactgtaaaatagctactatctgtacaag atattatagaaatatgtttcaaatgatatataaatgctacatctttgagactaataatgcaaaattttaaataatct aattatataatcacgatgtaattccaaggtaccagccagaacatctaaactgataaaaatttgtactaaatacattg ctgtagtgaaataaagtttgtctggaattttcaggtgctagactcaacttgagtataaaatacttagctgaaaattt tctatctgtaaaataaactttcataaagaaacaataaatcaaaagccccaaaccccaggggctcccatttttatt aataaacaaaaagcaaaagaagatatcattagctgttcggttttgcatgattttttgttgttttagtgcatttggttt tgttctaaatggtttatcatctgtttgatgcactaactcttttgggctcttggatgttggacgctggctcttacaaa aagctacacacatctacattatattcatttttattttaacacacacacacaaatgaatccctgtgcccgggattgcac taggtaccaggaatacaaatacaaacataggagctcaaaacaaaactagtgagaaagatgggaaatactacagtca tagctataaagtaatgggctaagtaacacattagcagaaataaatcatagaatacagagaaaaaggttaaggtttg attgcctgccatggtcagataaagttccacagagacga□
```

```
Actual comp position    81844    sequence    gcttgcctgagtaggcaaac
Reverse comp position   81844    sequence    gtttgcctactcaggcaagc
 g c t a  toalno  totalvalue 6    5  4  5  20  62

Actual comp position    82362    sequence    tgtaattccaaggtaccagcc
Reverse comp position  82362     sequence    ggctggtaccttggaattaca
 g c t a  toalno  totalvalue 4    6  5  6  21  62
```

```
JOIN NUMBER -----  3
Length of pair 149
 Starting position of block    84416
 Block length (700 + pairlength + 800)    1649
Block . . .
tgattgcaaaaaaggtaataaactctcactcttattttttccttcatttgtaatgatctaatttacacagtactcaa tatttgggaaattctaatctccccaacgtgaggaagtggttgaggattagcaaagcaataagtgtttagcaaattgc taatatagtacaagtgaagaacttcagaatctgcttgaattctgttaaatgcagcaactaaataaatgccacctcac cattttggatgcagtagtgattattcctccaaagcatccagctaacaaatgaactttattccctgggccacacagat ccagtttgtaatttacagatatctcaccttccatggagaattcacatcagtagaaattatattaagaatacctcaca gctgcaaatacaaagctgcagctttacttagaatgttatttgcattaaaaaatcaattttttatagctctaagattct agagaagctatattctatttaatacacataaacaatacaaaaatgatagtaaaagtttaaaacttagacatctgttt tttaaataaattaaagtttttaaaacacgcataaaaattcatcgcactgaaaaaaggaagcaaacagctttaaaggag tagttggttaaaaacatattaaaaaaccacgcaagtctccaaggaacaaagtttgacttttgtaaaacagtggaaaa ttttaccttaattttatcaatgtaattcacttctctgtgattgaacacttcatgggctccatttttgcaaaacaatct tttgtccttcctcagtaccagcagtgcccaaaatctttaagccataagctctagcaatttggcatgctgctaatcca acctgaaaaacaaatataacccaagagttatatattctctacactcctgtaaacacttaaatacatacaatgaactt aagattcctataggacccaccctaactttaaggaacttaagagtgtaaatgaagaaataagaaaaacagctaacttt aattgagcatttaaaatattccaggaaccatactaaataatttctacatattgttttattctatcctcacaatgacc ctataaagtagatactattattgtccctattgtacagataagaaagttgaagcttcaaattataagtaatttggcca agtcatatgcggagatggaaacaggagttagaccagtctgactgcagaacttgagttttttaaccactgcatcaagat gtttgcagggtttaaagatgatcagaacatgctctctgacttctttgtgcatatgaaattctaaataacaaatgtaa ggcctccaccatttaagtagaagagataggtatatgggcaaattaactaattcatccatatggtgaatgtttataga gtgtttacgatgtgctagacatggtacttaatgtaagaaataaacttatattctaagggtggaggaagataatagtc atatgaatgaataaaataaattcaggaaataaaagtgctaagaaaaaataagactggctgttgggttaaagagacag gaatagggctatttaggtcatcaggaagagccactctgaaaaaatgagacctgaaaaagtgaggaacaagccacg agaacatccggtcagccacgtggaggatgctgt□

Actual comp position    85062    sequence    gcaagtctccaaggaacaaag
Reverse comp position    85062    sequence    ctttgttccttggagacttgc
 g c t a toalno   totalvalue 5    5  2  9   21   62

Actual comp position    85563    sequence    gatggaaacaggagttagacc
Reverse comp position 85563    sequence    ggtctaactcctgtttccatc
 g c t a toalno   totalvalue 7  3  3  8   21   62

JOIN NUMBER -----  4
Length of pair 56
 Starting position of block    88895
 Block length (700 + pairlength + 800)    1556
Block . . .
attctaactgcagagctctaacttttccctctaagctcctgagaggcagattggcagctagtttctcgaagaggttt ctgacagccctgcattgggtgatttcattgaagggcttattttaagttctgagtcctcctcccccattcccccacat tagcattttcagccatgggttgtggtgttaaggacagggctgtatacgtgcactccatggatgtcatcaaagtgcag caggcaagcagcagaagggagatagaaggactaagaattcacagtgtggctttaccgtgctgtctggggcaacatag gtaagctttaatgagccttagtttccttatctaagggaatatggaattaatatcaaccttaaagaactgtttaaaat tctaaataaatattttttataacatatgctacttgaaggcaaaaacaaggccagtttatcttagtctacacccaatac aggtggaaaatctaacatattttttgaaggggtgctctgttgagtttattaaccaagaaatgctaaactaatgacaaa acatcacctcagaagaccaaaatcaaagttttactacataaagaaaaaaagcacctttgactctatttataaatc tgacttttaaaaatgaccaaaggaactataatgtgaaacccataaacccaagcttgtttcaaaatacattaaaaaa
```

-continued

```
atacttactcctccacttgccccatgaaccagaacactctctccagctttcacacaggcactgcaaaggaaagcata agttacatcaccttattttttgaagctaattaatctcgggtgttttcatcatcttaaggaatttctaccc ctagtct ggctaacacttacacaaacagcaaatgcaacctgacatacagccccaaatattccctaagctccacagaataaacaa agccttcaattcatttattccttgaacaaatatttattgggagtctttatgttccaggcactatgctgctggacact gggatgactatgtggtgctacttctgagtggctacagtccttgtgggttgtgaagtaaaattgctgagcctggagga tctggaatctctcattcccatatatccccca cagaaagggcctcaaagcaggtttattatatagctcagtctttatt ctgtggtctagagtaatgtccaagtaaacacagtagctattttttttgcccaaggaaagaaagaaattttt cttctc catgtctctgaacatcaggttgcaccagccttgtactctttcagggaggaatgctgagttagcaaaggtcagagagt aggaaatgcaataaattctatcacaaagattcccatgtcatccccctgaaatgtccagattctctggtgaaatggca ttttcttttacttccagttcacatgactactttt ctagtatgtactgaaaagaagggacatgcagcaaggcatgag gggatgcctcactattccagatggacggtgccaatgtcaaaagccagcagatgctgtgagatccagatctgactctc aggaaggctctcttact□

Actual comp position     89543    sequence    gtgaaacccataaacccaagc
Reverse comp position    89543    sequence    gcttgggtttatgggtttcac
 g c t a toalno   totalvalue 3     7   2   9   21  62

Actual comp position     90103    sequence    ctccatgtctctgaacatcag
Reverse comp position 90103       sequence    ctgatgttcagagacatggag
 g c t a toalno   totalvalue 3  7  6  5  21  62
================================================================
```

An additional rule relating to gene family members may also be included in the set of primer selection rules. Many genes in the human genome are members of gene families, which means that they closely resemble other genes at other positions in the genome. When primer sequences are selected for a certain gene, one may later find that the selected primers are actually undesirably present in these other family members. The cycle of selecting an appropriate primer sequence for a given gene, that is, identifying a candidate primer sequence, searching the public database to find out whether or not it is specific to that gene, identifying that it is not specific to the gene, reselecting another candidate primer sequence, etc., could go on for several loops before an appropriate primer sequence is identified.

An example command for operating the function for this task is:

primer611 sult1a1.txt sult1a1join.txt primerout sult1a2.txt sult1a3.txt where the program executable command is primer611, the input sequence file within which to find primers is sult1a1.txt, the input join file that tells the program where the coding (exons) regions is sult1a1join.txt, the output file is primerout, and the other two files, sult1a2.txt and sult1a3.txt, are sequence files of family members. The number of gene family files which may be included can be large.

When the program selects a candidate primer in the sult1a1.txt file, it then reads the sult1a2.txt and sult1a3.txt files to see if it is present If it is present, it discards it and selects another candidate primer. If it is not present in the files, it selects and stores it and goes on to find the next primer. The program also looks at the family member files in both forward and reverse directions to be complete and eliminate the user from having to format these files to be in the proper coding orientation.

Thus, the software can select primers that are unique to the gene of interest and can be relied upon for genes that are members of families. This functionality can be added to the functionality of picking the best primers around the exons of a gene for the primer design process—select the candidate primer only if it is unique to the target file and not present in the gene family files.

To further illustrate the functionality and output, below is a listing of the primeronly file and and a portion of the primerout file (listing the $1^{st}$ three primer pairs). The command used to generate this output is:

primer611 topo2a.txt topo2ajoin.txt primerout topo2b.txt chr18.txt.

The primerout file is defined in the fourth element of the above command and the primeronly file below is created and named automatically. The primerout file has each of the exon regions defined in the topo2ajoin.txt file printed out with " . . . . . " before and after the exon, and documents the steps that the program went through when picking the primers. The primerout file lists candidate primer sequences that otherwise met the primer selection rules, but was found in one of the gene family files and was therefore rejected (see areas that read "FOUND in"). The output presentation allows a user to go back to a specific region and redesign a primer if the primer selected happens to be in a repetitive sequence region not screened out with the gene family files. This may be done, for example, by doing a database search.

```
===========================================================================
"PRIMERONLY" FILE
=========================================================================== topE1E2-5                   actgtggaaacagccagtaga
        ☐
        topE1E2-3                   tcttgataacctcgctgtgtc
        ☐

☐
        topE3E4E5-5
        ☐ topE3E4E5-3
        ☐

☐
        topEGE7E8-5                 atgtgccaccctctatccag
        topEGE7E8-3                 ttagagatgatgaataaagctcc topE9E10E11-5               cccagcctaacagttcttttg
        topE9E10E11-3               ccactacgctcggccaattt topE12E13E14-5              aagagaacagtaactcccgtc
        topE12E13E14-3              caqcactgattccatgcatac topE15-5                    gccagaagttgtaggttcaag
        topE15-3                    ctttactcagtcccaagctct topE16-5                    gcgtgacacatagcaagtgc
        topE16-3                    gccagttcttcaatagtaccc topE17E18E19-5              gagaagaacctttgccaatgg
        topE17E18E19-3              ctccaccattactctcaccaa topE20E21E22-5              tgcctgtataccgggatatac
        topE20E21E22-3              ttgacaaaggtatactgctgga topE23-5                    cttctgtctccacaccttcc
        topE23-3                    ggagaqgtgagagagaqatg topE24-5
        topE24-3 topE25E26E27-5              aattgtttctcctactaccctc
        topE25E26E27-3              aacccatctcaaagatttaggc topE28E29-5                 aatgcctgtattgaattgcagg
        topE28E29-3                 taaaaccagtcttqggcttgg
===========================================================================

===========================================================================
"PRIMEROUT" FILE
===========================================================================

Gene Name: top

Sequence File: topo2a.txt
        Join File: top2ajoin.txt
        Output File: primerout No of Family sequence files: 2
        Family Sequence File: topo2b.txt
        Family Sequence File: chr18.txt
        Number of characters in Sequence file: 22080
        Number of Lines in Sequence file: 2

JOIN Values . . .                                29

1           1           66      topE1
            2         290          502      topE2
            3        1443         1616      topE3
            4        1806         1907      topE4
            5        2015         2152      topE5
            6        4630         4768      topE6
            7        5136         5293      topE7
            8        5586         5711      topE8
            9        6318         6428      topE9
           10        6571         6676      topE10
           11        6767         6876      topE11
```

-continued

```
            12          8378         8470     topE12
            13          8770         8884     topE13
            14          8988         9109     topE14
            15         10207        10355     topE15
            16         12180        12411     topE16
            17         12598        12732     topE17
            18         12852        13052     topE18
            19         13194        13389     topE19
            20         14138        14229     topE20
            21         14332        14496     topE21
            22         14628        14711     topE22
            23         16803        16934     topE23
            24         18702        18854     topE24
            25         19098        19221     topE25
            26         19328        19371     topE26
            27         19799        19933     topE27
            28         21275        21474     topE28
            29         21792        22080     topE29

SORTED JOIN Values . . .

1             1           66     topE1
             2           290          502     topE2
             3          1443         1616     topE3
             4          1806         1907     topE4
             5          2015         2152     topE5
             6          4630         4768     topE6
             7          5136         5293     topE7
             8          5586         5711     tapE8
             9          6318         6428     topE9
            10          6571         6676     topE10
            11          6767         6876     topE11
            12          8378         8470     topE12
            13          8770         8884     topE13
            14          8988         9109     topE14
            15         10207        10355     topE15
            16         12180        12411     topE16
            17         12598        12732     topE17
            18         12852        13052     topE18
            19         13194        13389     topE19
            20         14138        14229     topE20
            21         14332        14496     topE21
            22         14628        14711     topE22
            23         16803        16934     topE23
            24         18702        18854     topE24
            25         19098        19221     topE25
            26         19328        19371     topE26
            27         19799        19933     topE27
            28         21275        21474     topE28
            29         21792        22080     topE29

COMBINED JOIN Values . . .

1          1           502     topE1E2
     2       1443          2152     topE3E4E5
     3       4630          5711     topE6E7E8
     4       6318          6876     topE9E10E11
     5       8378          9109     topE12E13E14
     6      10207         10355     topE15
     7      12180         12411     topE16
     8      12598         13389     topE17E18E19
     9      14138         14711     topE20E21E22
    10      16803         16934     topE23
    11      18702         18854     topE24
    12      19098         19933     topE25E26E27
    13      21275         22080     topE28E29

Total no of joins: 13

PAIR NO: 1 First 1 Second 502 Name
        topE1E2
        PAIR Length . . . 501
        Block Length . . . : 1301
        Block starting position . . . : 0 n . . .
nnnattcagtaccaaatttactgtggaaacagccagtagaqaatacaagaaaatgttcaaacaggcaagtaaataag tgtcttgtaccttaatgataaatggtagtagtatagccatttataatggcattaatgattggtttaatttaacataa
```

-continued

```
tttataagctattgaagtatggaaaattataagcatatatattaggttattaggactcataaatttatgttatttac
ttccagtttgtgagatgacttgaattttcatgttttcctattctttacttccatagacatggatggataatatggqa
agagctggtgagatggaactcaagcccttcaatggagaagattatacatgtatcacctttcagcctgatttgtctaa
gtttaaaatgcaaagcctggacaaagatattgttgcactaatggtcagaagagcatatgatattgctggatccacca
aagatgtcaaagtctttcttaatggaaataaaactgccat ...
gagtattttcctggatgttaaggataataagggatttttgtaatcattgtcaagtgcaaaattgaattttttcccctc
ccatatgttttttgtttgtttgtttgtttgtttgagacagagtctcacactgttgcccgggctgqagtgcagtg
gcacgatctcggctcaccgcaacctccacctcccaggttcacgcaattctcctgcctcagcctcccaagtagctggg
attacaggtgcctgccaccacacctggctaattttttgtattttagtagagacaggtttcactatgttggccaggc
tggtctcgaacaccagacctcatgatccacccgtcttggcctcccaaagtgctgggattacaggcatgagccactgc
acctggcccaaccatatgtatttcttaccacttctcacatatgttcttgaaagagaatggtatgccacatttttt
aatcagctcatttaaacttaccgaaggaatttcttttctcaaagaaacacctaaaataaatatttcatgtccttttt
ttattttccttttctttcttttcttgataacctcgctgtgtcacccaggctggagtacagtgatgcaatcacggct
cactacagcctggacctcccaggctcaagcgatcatcccacctcagcttctggagtagctggaaatgcaggcagcac
caccatgcccagctaatttttttttttctttttaatagagqtggggatctcactatgttgcccaggctggtcttgaa
ctcctgggctcaagtgatccacccacctc□
```

Did not get PRIMER, what to do, DO NOT HAVE ENOUGH CHARACTERS: 1 TO DEAL

| | | | | | |
|---|---|---|---|---|---|
| Seq ... | tcttgataacctcgctgtgtc | FOUND in: | chr18.txt at | 8964 | position |
| Seq ... | ttgataacctcgctgtgtcac | FOUND in: | chr18.txt at | 8966 | position |
| Seq ... | gataacctcgctgtgtcacc | FOUND in: | chr18.txt at | 8968 | position |
| Seq ... | ataacctcgctgtgtcaccc | FOUND in: | chr18.txt at | 8969 | position |
| Seq ... | caggctggagtacagtgatg | FOUND in: | chr18.txt at | 8988 | position |
| Seq ... | aggctggagtacagtgatgc | FOUND in: | chr18.txt at | 8989 | position |
| Seq ... | ctggagtacagtgatgcaatc | FOUND in: | chr18.txt at | 8992 | position |
| Seq ... | ggagtacagtgatgcaatcac | FOUND in: | chr18.txt at | 8994 | position |
| Seq ... | gagtacagtgatgcaatcacg | FOUND in: | chr18.txt at | 8995 | position |
| Seq ... | agtacagtgatgcaatcacgg | FOUND in: | chr18.txt at | 8996 | position |
| Seq ... | cagtgatgcaatcacggctc | FOUND in: | chr18.txt at | 9000 | position |
| Seq ... | gtgatgcaatcacggctcac | FOUND in: | chr18.txt at | 9002 | position |
| Seq ... | gcaatcacggctcactacag | FOUND in: | chr18.txt at | 9007 | position |
| Seq ... | caatcacggctcactacagc | FOUND in: | chr18.txt at | 9008 | position |
| Seq ... | aatcacggctcactacagcc | FOUND in: | chr18.txt at | 9009 | position |
| Seq ... | tcaagcgatcatcccacctc | FOUND in: | chr18.txt at | 9043 | position |
| Seq ... | aagcgatcatcccacctcag | FOUND in: | chr18.txt at | 9045 | position |
| Seq ... | gatcatcccacctcagcttc | FOUND in: | chr18.txt at | 9049 | position |
| Seq ... | tcatcccacctcagcttctq | FOUND in: | chr18.txt at | 9051 | position |
| Seq ... | cacctcagcttctggagtag | FOUND in: | chr18.txt at | 9057 | position |
| Seq ... | acctcagcttctggagtagc | FOUND in: | chr18.txt at | 9058 | position |
| Seq ... | ctcagcttctggagtagctg | FOUND in: | chr18.txt at | 9060 | position |
| Seq ... | tcagcttctggagtagctgg | FOUND in: | chr18.txt at | 9061 | position |

-continued

| | | | | | |
|---|---|---|---|---|---|
| Seq . . . | cttctggagtagctggaaatg | FOUND in: | chr18.txt at | 9065 | position |
| Seq . . . | ttctggagtagctggaaatgc | FOUND in: | chr18.txt at | 9066 | position |
| Seq . . . | ggagtagctggaaatgcagg | FOUND in: | chr18.txt at | 9070 | position |
| Seq . . . | gagtagctggaaatgcaggc | FOUND in: | chr18.txt at | 9071 | position |
| Seq . . . | gtagctggaaatgcaggcag | FOUND in: | chr18.txt at | 9073 | position |
| Seq . . . | tagctggaaatgcaggcagc | FOUND in: | chr18.txt at | 9074 | position |
| Seq . . . | gggatctcactatgttgccc | FOUND in: | chr18.txt at | 9139 | position |

```
PRIMER 2 actual: -2130704935 . . . tctcactatgttgcccaggc

Letters 20 g count 4 t count 6 c count 7 a count 3 total
62
reverse: -2130704935 ... gcctgggcaacatagtgaga
topE1E2-3 gcctgggcaacatagtgaga Number of letters between pairs: -2131274331

PAIR NO: 2 First 1443 Second 2152 Name
topE3E4E5
PAIR Length . . . 709
Block Length . . . : 2208
Block starting position . . . : 743
``` tgcctgccaccacacctggctaatttttgtatttttagtagagacaggtttcactatgttggccaggctggtctcg aacaccagacctcatgatccacccgtcttggcctcccaaagtgctgggattacaggcatgagccactgcacctggcc caaccatatgtatttttcttaccacttctcacatatgttcttgaaaagagaatggtatgccacatttttaatcagct cattttaaacttaccgaaggaatttctttctcaaagaaacacctaaaataaatatttcatgtcctttttttattttc cttttcttcttttcttgataacctcgctgtgtcacccaggctggagtacagtgatgcaatcacggctcactacag cctggacctcccaggctcaagcgatcatcccacctcagcttctggagtagctggaaatgcaggcagcaccaccatgc ccagctaattttttttttctttttaatagaggtggggatctcactatgttgcccaggctggtcttgaactcctggg ctcaagtgatccacccacctcggcctgtgtcctttaatgaccattcccttatgcctatcagtgaacatcattgcatt ggttttggaaagtcctcatagtctatcattgaacctattttttaataactttcttaatactgttacctttaattcct gtacagg . . .

aaaaggatttcgtagttatgtggacatgtatttgaaggacaagttggatgaaactggtaactccttgaaagtaatac atgaacaagtaaaccacaggtgggaagtgtgtttaactatgagtgaaaaaggctttcagcaaattagctttgtcaac agcattgctacatccaaggtaattttattcttaaattattaatcatgatttatctttacatatatgtgttcttattg ttttttaatatataaagtgcacttgaatattgggctagcttagtataaaggaggttaaattagttttaatgtttgat tattataattttgaggatactgagttttcagtttggtattttttccttattagggtggcagacatgttgattatgta gctgatcagattgtgactaaacttgttgatgttgtgaagaagaagaacaagggtggtgttgcagtaaaagcacatca ggtatgtgcttttggcagttttcttttttctaaagtcaaggaagaagagaaaggctataaataaagcatgagtacatt tttagtggcttaatatcaacttctattgcaggtgaaaaatcacatgtggattttgtaaatgccttaattgaaaacc caacctttgactctcagacaaaagaaaacatgactttacaacccaagagctttggatcaacatgccaattgagtgaa aaatttatcaaagctt . . .

gagtacttagaggaaaataaaaatagaaacacctgactttatttccattgcacttcttagctctgcagaaacaatg attcttctcatagtgagcttctccaagtcttcccaatctgaaaaggaagtaaaaaagggctttactttaactgattt accaaagacttaatgaccgtctatatttcagtatttcccaattacatttaccattaagcttagatcacttttgaat taatctagctgtttaacaaacaccctcacttaaatgcctaagacttgctttcagtcaacacatccaaaattgaattt gttacctccatactcactgatttgcccatacaagcagccccccactctcaacaaaaaaacaacttcctatcttagt aaaaagccccaaccaacctctaggttgtataaacaagaaagctgggagccttcctttatttcccctcctctctaatc -continued

```
cggtcaataagaatcatctcttggatgctgcagtagcttctcaccattatctcttttttggtttactacaataggtt cttaaccttcatactggttaagtccttccttggaatgcttttgagtgacttttgtgttaaaacacccatttttatc ttcactctcatttgaaatctttcaatgacttccactcagggaaagtccaaattccataatttggccaacaagaaaga tctgctgtaatctaattacacctacttctccaactcatctcagtgccagttttcgtatattgtcctgttgctttta aattactgaaaagcacagtgctcttcccc□
```

| | | | |
|---|---|---|---|
| Seq . . . ccattcccttatgcctatcag | FOUND in: | chr18.txt at 9221 | position |
| Seq . . . gaccattcccttatgcctatc | FOUND in: | chr18.txt at 9219 | position |
| Seq . . . tcaagtgatccacccacctc | FOUND in: | chr18.txt at 9182 | position |
| Seq . . . actcctgggctcaagtgatc | FOUND in: | chr18.txt at 9172 | position |
| Seq . . . tgaactcctgggctcaagtg | FOUND in: | chr18.txt at 9169 | position |
| Seq . . . cttgaactcctgggctcaag | FOUND in: | chr18.txt at 9167 | position |
| Seq . . . aggctggtcttgaactcctg | FOUND in: | topo2b.txt at 36055 | position |

PRIMER 1:
1246 . . .
tcactatgt-
tgcccag-
gctg

Letters 20
g count 5
t count 6
c count 6
a count 3
total
62
topE3E4E5-5cactatgttgcccaggctg

| | | | |
|---|---|---|---|
| Seq . . . gcctaagacttgctttcagtc | FOUND in: | chr18.txt at 10319 | position |
| Seq . . . cctccatactcactgatttgc | FOUND in: | chr18.txt at 10365 | position |
| Seq . . . ctccatactcactgatttgcc | FOUND in: | chr18.txt at 10366 | position |
| Seq . . . tccatactcactgatttgccc | FOUND in: | chr18.txt at 10367 | position |
| Seq . . . cactgatttgcccatacaagc | FOUND in: | chr18.txt at 10375 | position |
| Seq . . . ctgatttgcccatacaagcag | FOUND in: | chr18.txt at 10377 | position |
| Seq . . . tgatttgcccatacaagcagc | FOUND in: | chr18.txt at 10378 | position |
| Seq . . . tttgcccatacaagcagccc | FOUND in: | chr18.txt at 10381 | position |
| Seq . . . cccaaccaacctctaggttg | FOUND in: | chr18.txt at 10445 | position |
| Seq . . . taaacaagaaagctgggagcc | FOUND in: | chr18.txt at 10467 | position |
| Seq . . . caagaaagctgggagccttc | FOUND in: | chr18.txt at 10471 | position |
| Seq . . . aagaaagctgggagccttcc | FOUND in: | chr18.txt at 10472 | position |
| Seq . . . ctgggagccttcctttatttc | FOUND in: | chr18.txt at 10479 | position |
| Seq . . . tgggagccttcctttatttcc | FOUND in: | chr18.txt at 10480 | position |
| Seq . . . gaatcatctcttggatgctgc | FOUND in: | chr18.txt at 10525 | position |
| Seq . . . atcatctcttggatgctgcag | FOUND in: | chr18.txt at 10527 | position |
| Seq . . . atctcttggatgctgcagtag | FOUND in: | chr18.txt at 10530 | position |
| Seq . . . ctcttggatgctgcagtagc | FOUND in: | chr18.txt at 10532 | position |
| Seq . . . ggatgctgcagtagcttctc | FOUND in: | chr18.txt at 10537 | position |
| Seq . . . tgctgcagtagcttctcacc | FOUND in: | chr18.txt at 10540 | position |
| Seq . . . ctggttaagtcctttccttgg | FOUND in: | chr18.txt at 10605 | position |

-continued

| | | | | | | |
|---|---|---|---|---|---|---|
| Seq . . . | ttcaatgacttccactcaggg | FOUND in: | chr18.txt at | 10689 | position |
| Seq . . . | atgacttccactcagggaaag | FOUND in: | chr18.txt at | 10693 | position |
| Seq . . . | cttccactcagggaaagtcc | FOUND in: | chr18.txt at | 10697 | position |
| Seq . . . | ctcagggaaagtccaaattcc | FOUND in: | chr18.txt at | 10703 | position |
| Seq . . . | tggccaacaagaaagatctgc | FOUND in: | chr18.txt at | 10730 | position |
| Seq . . . | gccaacaagaaagatctgctg | FOUND in: | chr18.txt at | 10732 | position |
| Seq . . . | cacctacttctccaactcatc | FOUND in: | chr18.txt at | 10764 | position |
| Seq . . . | cctacttctccaactcatctc | FOUND in: | chr18.txt at | 10766 | position |
| Seq . . . | cttctccaactcatctcagtg | FOUND in: | chr18.txt at | 10770 | position |
| Seq . . . | ttctccaactcatctcagtgc | FOUND in: | chr18.txt at | 10771 | position |
| Seq . . . | ctccaactcatctcagtgcc | FOUND in: | chr18.txt at | 10773 | position |
| Seq . . . | ccaactcatctcagtgccag | FOUND in: | chr18.txt at | 10775 | position |

Did not get PRIMER, what to do, DO NOT NAVE ENOUGH CHARACTERS: 2208 TO DEAL

PAIR NO: 3 First 4630 Second 5711 Name topE6E7E8
PAIR Length . . . 1081

Block Length . . . 2580

Block starting position . . . 3930 gatctcagttcactgcaacccgcgcctccocaggttaaagoaattctcctgcctcagcctcccaagcagctaggatta cagccatctcaccaccaccatgcctggctaccctttttttttttttttttttttttgagacggagtttcactttt gtcacccaggctggagtgcaatggtgcgatcttggctcgctgcaacctctacctcctgggttcaagcgattctcctg cctcagcctcccgagtagctggaattacaggtgcccaccaccacgccagctaattttttgtattttttagtagagccgg ggtttcgccatgttggccaggccggtctcaaactcctgacctcaggtgttctgcccaccttggcctcctaaagtgct gggattataggcgtgagccaccgtgcctggtctaatttgttttaaccactatatctccaacaagtagctcagtgcta gcacaatataattatatagtaaatatttattgaacgaatgaaccaaaaggagcagctccctcagtggtgataacctg acatgggaagatgtgccaccctctatccagaaattattgttctacatcttttaatttttgaatcatttttatttgt attaaggctcatttgtattctagatttctgatagatcccttcttccctaatatgatccctaatatgaatcttctcgt tttcagg . . .

cattggctgtggtattgtagaaagcatactaaactgggtgaagtttaaggcccaagtccagttaaacaagaagtgtt cagctgtaaaacataatagaatcaagggaattcccaaactcgatgatgccaatgatgcaggtatatatttaataatg tttccaaacttttaagtcttatagttgttattttattcattaatggcataccacggatatttatttttccccttgaca gaataactatattcaacagaataacttgttaaaaatcggcccgtttcctattatggaagatttaggtcatttccatg ttataaataatattgaggtgattattttggagtataaaacaagaatgtttatattatgatctattacctaacaaata attttgctcattatatagtaaattgtgttttatcacaaggctataaacagcatgttcaagttagtatatttgaggtt gaactaaatgtgctaatattaatatgtatatttttattttaggggccgaaactccactgagtgtacgcttatcctg actgagggagattcagccaaactttggctgtttcaggccttggtgtggttgggagagacaaatatgggttttccc tcttagaggaaaaatactcaatgttcgagaagcttctcataagcaggtagaatataagacgatcttcagaatctaaa tctaatttataatacaagacttatgcttatatttaattccctcattaggcattttaaaatatattttagacaattt gtgcttattttgagaaattaggtacattgtagcctatttttaacagacctttctgatgtagtaaattataagctaata gctcaaaatactggagctcaagaaaatccaagcaacatatactgttaaatttctttgttcttttcaaatttataaac gatgcttttttttggtatatgtccatttcagatcatggaaaatgctgagattaacaatatcatcaagattgtgggtct -continued

```
tcagtacaagaaaaactatgaagatgaagattcattgaagacgcttcgttatgggaagataatgattatgacagatc agt . . .

cagatttgttattaaattttagattgttcaactaaattaagcatgtcttaatttaatttcattgttttttgccatg aaaataaattacttaaataggagctttattcatcatctctaatcaacatctaatcagatatgcttatatcatatgta tgttgcaaatacaggttaagtgagtctggatttgaacagacctttttttgattcccatagaaaatttgacaaattgcc agtaggtcagtcataatattttttatttctaaacaattctttgtttgtttgagatggagtttcgcccttgtcgccc aggctggagtgcaatggtgcaatcttggctcactgcaacctccgcctcatgggttcaagcgattctcctgcctcagc ctcccgagtagctgggattgcaggcggatgccaccacacccaactaattttgtatttttagtggagacagggtttc accatgttggccaggctggtctcgaacgcctgacctcaggcgatccgcctgcctcggcctcccaaagttctgggatt acagatgttagctaccacgcccagcctaacagttcttttgaactttggctttcaaatctttctaggaccaagatggt tcccacatcaaaggcttgctgattaattttatccatcacaactggccctctcttctgcgacatcgttttctggagga atttatcactcccattgtaaaggtacgctaatttctaagtaccatcatggatattttaagaccctactcctcaaacc tggatatacatataagccccgtcacatgt□

PRIMER 1: 4479 . . . atgtgccaccctctatccag
        Letters 20 g count 3 t count 5 c count 8 a count 4 total
        62
        topE6E7E8-5 atgtgccaccctctatccag
        PRIMER 2 actual: 6005 . . . gagtgcaatggtgcaatcttg Letters 21 g count 7 t count 6 c count 3 a count 5 total
        62 reverse: 6005 . . . caagattgcaccattgcactc
        topE6E7E8-3 caagattgcaccattgcactc Number of letters between pairs: 1526
======================================*
======================================*
======================================*
============================================================
```

There are two gene family files in this comparison. The topo2b.txt file is a human genome sequence for a gene called topoisomerase 2b, which is highly related to the gene of interest, topoisomerase 2a. In the primerout file, many of the candidate primers the program selected were present in this family member and were therefore rejected. This demonstrates the utility of the functionality of this program. The second family member sits on chromosome 18 and is a pseudogene (a duplicated region of DNA that does not make a real gene—a serious nuisance for designing primers that are to amplify a single genetic position). The program has accommodated for this as well; it selected a candidate primer that was found in this file a large number of times.

Without this functionality, primers that would amplify three different regions at the same time would be designed: the topo2a region of interest; the topo2b region related to it; and a nuisance region in chromosome 18. Unfortunately, the resulting data would show numerous discrepancies that are not real polymorphisms. These sequences are actually from different genetic positions that are highly similar to one another but not identical. Thus, most of the "SNPs" found in this manner are not SNPs at all. If one tried to genotype people at a "false SNP," they would get incoherent data as they would be looking at three different positions within the genome at the same time. It is important to produce data for single positions at a time so that the data can be accurately read and interpreted.

Advantageously, the rules that the inventive software uses in the preamplification process are different than those of conventional programs in that they are suitable for use in designing high throughput experiments where many different things can be done simultaneously. It is more efficient to do simultaneous amplifications of four or five regions in 500 people, for example, rather than doing them one by one. This is where the rule regarding the fixed predetermined annealing temperature (e.g., 62° Celsius) comes into play: since all of the primers selected by the program have the same annealing temperature, the work can be done more efficiently. Another example is where the software automatically decides if a single primer pair can be utilized for two or more coding regions, which saves additional time and expense. Furthermore, the rule regarding gene family data is important for generating reliable output data and for efficiency.

The output of the software is also unique. The numbers included in the output use the numbering pattern that exists in the input sequence file (for example, starting at "10003") rather than starting at "1" like most other programs. This means that a primer at position "11234" can be quickly located, whereas in other programs the number for the primer would be "1231" and one would have to perform the math to figure out its location. This is particularly important for those primers that have to be redesigned manually due to having certain characteristics that can only be determined through a database search.

Additional Details Regarding The Discovery of Reliable SNP and Haplotype Data. The description that follows provides additional details regarding steps 318–342 of FIG. 3B, which may be referred to as part of the post-amplification process. As described earlier, one important goal of the program is to find reliable discrepancies between individuals at a sequence of a particular genetic locus or location in the genome. To do this, the inventive methods use a direct measure of the nucleotide base quality, or "phred" score, of an observed discrepancy (at steps 326–328 of FIG. 3B).

Actual DNA sequence data files, called chromatograms, are utilized as input, as quality information is an inherent part of such files. As is well-known, a sequence chromatogram looks like a series of colorful peaks and valleys. The color of a peak indicates the DNA base present at that position in the sequence. Peaks in a graph for a good sequence tend to be higher than for a bad sequence, and overlapping peaks tend to indicate poor reliability. Such information is used to determine whether a discrepancy in a sequence alignment represents a good candidate SNP or not.

The functionality of a conventional phred program is used to call the quality of every letter, and the program aligns the sequences and finds where they are "reliably" different from one another. By reliable, it is meant that the differences in sequence are differences between letters of good quality. An example of one such program is the phred program available from the University of Washington, which ascribes a numerical value to indicate the quality of each letter of a sequence. The phred functionality makes a separate file with all of these numbers, for each letter.

DNA sequences from various individuals are aligned using a conventional sequence alignment algorithm (at step 320), such as that provided using conventional Clustal software functions available by and from the EMBL, Heidelberg Germany, and is a re-write of the popular Clustal V program described by Higgins, Bleasby, and Fuchs (1991) CABIOS, 8, 189–191 (Thompson, J. D., Higgins, D. G. and Gibson, T. J. (1994) (CLUSTAL W: improving the sensitivity of progressive multiple sequence alignment through sequence weighting, positions-specific gap penalties and weight matrix choice. Nucleic Acids Research, 22:4673–4680). Thus, the sequence alignment file is the first input file to the program. Any discrepancy that occurs within a neighborhood of other discrepancies is recognized so that the quality value information can be checked. If this information is greater than predetermined quality information, such as a user-defined input value, it is accepted and presented to the user for final acceptance. If not, it is discarded. The quality control file created from the phred functionality serves as the second input file.

In the sequence within which the discrepancy occurs, positions of the minor letters of the discrepancy are presented to the end-user. This lets the end-user contemporaneously call up the raw DNA sequence chromatogram and find the actual trace data peak for the letter. This is advantageous because a visual inspection of raw DNA sequence data is the most reliable method of determining whether a discrepancy is valid. While the purpose of the software is to eliminate many time consuming steps, in some cases, borderline quality values nonetheless necessitate its execution. The presentation of the precise position and relevant file names for a discrepancy makes this step easy to execute. Also, the end-user is shown presentations of discrepancies that do not meet the quality control criteria. This is important because, in some cases, a borderline quality value may conceal good data due to other problems with sequence compressions or peak spacing.

Another important attribute is afforded the software because it can recognize reliable base deletion polymorphisms. This is performed by parsing the phred quality data for the bases surrounding the deletion in randomly selected sequences which contain the deletion. With conventional programs, if a discrepancy is a deleted base there is no quality control information to check since no data is produced for a non-base (and there is consequently no phred value for the deleted base). This eliminates any discovery of single base deletion polymorphisms. Deletion polymorphisms are common and, since the goal is to thoroughly document the various genetic haplotypes in a population, a SNP-finding program that can recognize deletion polymorphisms offers competitive advantages. Not knowing all of the variants in a gene sequence causes the resolution of haplotype-based studies to be sub-optimal, compared to being able to recognize all variants (including deletion polymorphisms).

The software may also incorporate rules to maximize efficiency during these steps. For example, the program may focus on determining the phred value for discrepancies that fall within a block of sequence with an acceptable average phred value. As another example, the user-defined phred value could be different for different regions of the sequence. In another variation, the program is configured to recognize amino acid differences by translating the sequences and instructed to only present candidate polymorphisms that result in a change in amino acid sequence.

Example Walk-Through. Input=(1) Clustal W alignment file and (2) phred quality file. The user inputs a minor letter phred quality control value for the current run, as well as a local phred quality control value. For example, the user may enter the values "24" and "17" for the the minor letter and local phred quality control values, respectively. Then, from the first input file, each column (position or slice) of the alignment is analyzed to determine whether the column is homogeneous (i.e., whether each sequence has the same letter at that position) or heterogeneous (i.e. whether there are two or more different letters at that position).

As an example, consider the following:

```
AHRE11-3
AGGGGGTAGATTTTAAAAAT-CATGTTAATGTTATTTACT-

ARRE11-3-E10
AGCGGGTAGATTTTAAAAAT-CATGTTAATGTTATTTACT-

AHRE11-3a
AGGTGTAAGATTTTAAAAATACATGTTAATGTTATTTACT-

AHRE11-3u
AGGGGTA-GATTTCAAAAATACATGTTAATGTTATTTACT-

14
AGGGGTA-GATTTTAAAAATACATGTTAATGTTATTTACT-

AHRE11-3-C4
AGGGGTAAGATTTTAAAAATACATGTTAATGTTATTTACT-

AHRE11-3-D5
AGGGGTAAGATTTTAAAAATACATGTTAATGTTATTTACT-
```

The first column of letters is homogeneous. So is the second and third. The fourth is heterogeneous, as is the sixth, etc.

The second input file is the phred quality file, which takes the format of the 1×N matrix below for each sequence. The entry for the first sequence above (AHRE11-3) appears below:

>AHRE11-3 folder=AHRE11-3 length=414

8 9 23 24 32 34 27 27 34 34 32 32 34 34 32 32 29 29 26 26
26 28 34 31 29 29 32 35 35 35 45 45 45 40 35 35 39 32 33
32

In this file, the first two letters are of very low quality or reliability because, for biochemical reasons, sequencing reactions routinely have trouble at the beginning of a sequence read.

For each column of the alignment, the software recognize whether there is a discrepancy (i.e., major and minor letters.) If a discrepancy exists, then the following logic is executed:

For each minor letter, read the phred value. For example, in column 14 above, sequence AHRE11-3u has a C but the others have a T. The "C" is a minor letter and it has the value 34.

Calculate the average phred value for the major letter (G in column 14 above)

Calculate the average phred value for each minor letter (in column 14 above, there is only one minor so this is the same as the phred value for that letter.

Determine the number of major letters.

Determine the number of minor letters.

Calculate the average phred value for the block of letters 7 in front and 7 behind the column using all of the input sequences and their quality values. This will be called the local phred quality value.

To process the job, the phred value of the minor letter and average phred value of the major letter are utilized such that If the phred value of any minor letter in the column is greater than the user-defined threshold value, And If the average phred value of the major letter for the column is above a different threshold value defined by the user, Then label the column as accepted and present to the user for visual inspection.

Alternatively, a more sophisticated method for determining the worth of a positional column is to use a function to calculate the probability that a column contains a reliable polymorphism using the average quality value for the column, the quality values for the minor letters, the quality value for the region around the column (using all the sequences), or other variables. For this approach the following logic is utilized:

1) A column with a high average major letter phred score and a high minor letter phred score is a better column than one with
    a) a low average major letter phred score and a high minor letter phred score;
    b) a high average major letter phred score and a low minor letter phred score;
    c) a low average major letter phred score and a low minor letter phred score; and 2) A column with a discrepancy in a region of sequence that has a high local phred quality value is better than one in a region with a low local phred quality value.

Preferably, a probability function is employed for this task, including variables for that which is measured above. For example, one might use Bayes' theorem to calculate this probability; for every column a vector is created from the variables calculated above and the linear equation:

$$y = A_1 X_1 + A_2 X_2 + A_3 X_3 \ldots A_n X_n$$

giving the vector $Y=(A_1, A_2, A_3 \ldots A_n)$, where An are parameters.

Then determine a Bayesian estimate $p(w|x) = [p(x|w)p(w)]$ divided by $p(x)$, where $p(w|x)$=classification score of the column as good or bad or somewhere in between (called the posterior probability), $p(x)$ is the frequency or uniqueness or worth of this vector, and $p(w)$ is the frequency or uniqueness of the class. $P(x|w)$ is the conditional probability that x is observed given that w is also observed—in this frequency that vectors of the above An are observed for true SNP columns (determined using other suitable biochemical techniques).

Once the alignment file has been inspected for every column, the results are presented to the user. For example, if the probability is high that a column contains a reliable polymorphism, then the column is presented to the user along with 7 letters in front and 7 letters behind for each sequence in the alignment For example,

```
Sequence 1        TTTATCTGACTGGAG
Sequence 2        TTTATCTGACTGGAG
Sequence 3        TTTATCTCACTGGAG
```

Also, the "average" sequence 200 letters in front and 200 letters behind the column is presented. For example,

```
ATTATGCTCG ATTATGCTCG ATTATGCTCG ATTATGCTCG ATTATGCTCC
ATTATGCTCG ATTATGCTCG ATTATGCTCG ATTATGCTCG ATTATGCTCG
ATTATGGTCG ATTATGCTCG ATTATGCTCG ATTATGCTCG ATTATGCTCG
ATTATGCTCG ATTATGCTCG ATTATGCTCG ATTATGCTCG ATTATGCTCG G/C
ATTATGCTCG ATTATGCTCG ATTATGCTCG ATTATGCTCG ATTATGCTCG
ATTATGCTCG ATTATGCTCG ATTATGCTCG ATTATGCTCG ATTATGCTCG
ATTATGCTCG ATTATGCTCG ATTATGCTCG ATTATGCTCG ATTATGCTCC
ATTATCCTCG ATTATGCTCG ATTATGCTCG ATTATGCTCG ATTATGCTCG
```

In the above example, there is only one column with discrepancies; each of the other columns are homogeneous. In practice, this will be unusual and the presentation will look more like the following (note the letters R, Y, M):

```
YTTATGCTCG ATTATGCTCG ATTATGCTCG ATTATGCTCG ATTATGCTCG

ATTATGCTCG ATTATGCTCG RTTATGCTCG ATTATGCTCG ATTATGCTCG

ATTATGCTCG ATTATGCTCG ATTATGCTCG ATTATGCTCG ATTATGCTCG

ATTATGCTCG ATTATGCTCG ATTATGCTCG ATTATGCTCG ATTATGCTCG S

ATTATGCTCG ATMATGCTCG ATTATGCTCG ATTATGCTCG ATTATGCTCG

ATTATGCTCG ATTATGCTCG ATTATGCTCG ATTATGCTCG ATTATGCTCG

ATTATGCTCG ATTATGCTCG ATTATGCTCG ATTATGCTCG ATTATGCTCG

ATTATGCTCG ATTATGCTCG ATTATGCTCG ATTATGCTCG ATTATGCTCG
```

Where

R=A or G

Y=C or T

K=G or T

M=A or C

S=G or C

W=A or T

N=any base

B=C,G, or T

D=A,G or T

H=A,C or T

V=A,C or G

Other information may also be presented, such as the following: (a) for each sequence with a minor letter, the sequence name and the associated phred value for the minor letter; and (b) the local region phred score.

Example Output Below is a file that shows what the software produces as it inspects a single discrepancy.

```
k = 70
Position of Reference sequence without dashes:
65
Position of complement sequence: 209

Indicator

QUALITY INFORMATION
Discrepancies at position
70

Minor letter 1::-::1
Minor letter 2::A::1
Major letter ::G::60
Got '-' as minor value Got 1
minor characters
Minor characters ::: A Check quality for mlnor A Got sequence, sequence
id AHRE9-5-D7
No of dashes before minor
character position 67
Quality value (
4) is lessthan24 at position 4
Total No of minor charaters quality is less than24 is 1
Total No of minor charaters
quality is greater than24 is 0

AHRE9-5-D2          C-TCTGAGTTA;Accumulated SNP # 0 S

AHRE9-5-H1          C-TCTGAGTTA;Accumulated SNP # 0 S

AHRE9-5-C4          C-TTTGAGTTA;Accumulated SNP # 0 S

ABRE9-5-B5          C-TCTGAGTTA;Accumulated SNP # 0 S

AHRE9-5-D5          C-TTTGAGTTA;Accumulated SNP # 0 S

AHRE9-5-A6          C-TCTGAGTTA;Accumulated SNP # 0 S
```

-continued

```
AHRE9-5-B2      C-TCTGAGTTA;Accumulated SNP # 0 S
AHRE9-5-C3      C-TCTGAGTTA;Accumulated SNP # 0 S
AHRE9-5-C2      C-TCTGAGTTA;Accumulated SNP # 0 S
AHRE9-5-D3      C-TCTGAGTTA;Accumulated SNP # 0 S
AHRE9-5-E2      C-TTTGAGTTA;Accumulated SNP # 0 S
AHRE9-5-F2      C-TCTGAGTTA;Accumulated SNP # 0 S
AHRE9-5-E1      C-TCTGAGTTA;Aocumulated SNP # 0 S
AHRE9-5-G2      C-TCTGAGTTA;Accumulated SNP # 0 S
AHRE9-5-G3      C-TCTGAGTTA;Accumulated SNP # 0 S
AHRE9-5-H2      C-TTTGAGTTA;Accumulated SNP # 0 S
ABRE9-5-D1      C-TTTGAGTTA;Accumulated SNP # 0 S
AHRE9-5-F1      C-TTTGAGTTA;Accumulated SNP # Q S
AHRE9-5-D12     CATTCGAGTTA;Accumulated SNP # 0 S
AHRE9-5-B4      CAT-CGAGTTA;Accumulated SNP # 0 S
AHRE9-5-D6      CAT-CGAGTTA;Accumulated SNP # 0 S
AHRE9-5-C1      CAT-CGAGTTA;Accumulated SNP # 0 S
AHRE9-5-A12     CAT-CGAGTTA;Accumulated SNP # 0 S
AHRE9-5-B11     CAT-AGAGTTA;Accumulated SNP # 0 S
AHRE9-5-D7      --AATAGAGTA;Accumulated SNP # 1 S
AHRE9-5-H12     ------GGTTA;Accumulated SNP # 0 S
AHBE9-5-D4      C-TCTGAGTTA;Accumulated SNP # 0 S
AHRE9-5-C5      C-TCTGAGTTA;Accumulated SNP # 0 S
AHRE9-5-B1      C-TCTGAGTTA;Accumulated SNP # 0 S
AHRE9-5-B3      C-TCTGAGTTA;Accumulated SNP # 0 S
AHRE9-5-A3      C-TCTGAGTTA;Accumulated SNP # 0 S
AHRE9-5-C6      CAT-CGAGTTA;Accumulated SNP # 0 S
AHRE9-5-F11     C-TCCGAGTTA;Accumulated SNP # 0 S
AHRE9-5-G11     C-TCCGAGTTA;Accumulated SNP # 0 S
AHRE9-5-C12     C-TTCGAGTTA;Accumulated SNP # 0 S
AHRE9-5-E10     C-TCCGAGTTA;Accumulated SNP # 0 S
AHRE9-5-C10     CTC-CGAGTTA;Accumulated SNP # 0 S
AHRE9-5-G12     CTCNCGAGTTA;Accumulated SNP # 0 S
AHRE9-5-D10     CATTCGAGTTA;Accumulated SNP # 0 S
AHRE9-5-D8      CATTCGAGTTA;Accumulated SNP # 0 S
AHRE9-5-D9      CATCCGAGTTA;Accumulated SNP # 0 S
AHRE9-5-E11     C-TCCGAGTTA;Accumulated SNP # 0 S
AHRE9-5-C9      CAT-TGAGTTA;Accumulated SNP # 0 S
AHRE9-5-E8      TATTCGAGTTA;Accumulated SNP # 0 S
AHRE9-5-B10     TCATCGAGTTA;Accumulated SNP # 0 S
AHRE9-5-D11     TCTTCGAGTTA;Accumulated SNP # 0 S
```

```
                    -continued
     AHRE9-5-C8        CAT-CGAGTTA;Accumulated SNP # 0 S AHRE9-5-B8        TCTTCGAGTTA;Accumulated SNP # 0 S AHRE9-5-F8        TCTCNGAGTTA;Accumulated SNP # 0 S AHRE9-5-H11       TCTCCGAGTTA;Accumulated SNP # 0 S AHRE9-5-A8        CAT-CGAGTTA;Accumulated SNP # 0 S AHRE9-5-F12       C-TTCGAGTTA;Accumulated SNP # 0 S AHRE9-5-E12       C-TCCGAGTTA;Accumulated SNP # 0 S AHRE9-5-F7        CATCCGAGTTA;Accumulated SNP # 0 S AHRE9-5-G10       C-TCCGAGTTA;Accumulated SNP # 0 S AHRE9-5-B9        C-TTCGAGTTA;Accumulated SNP # 0 S AHRE9-5-C7        --CTTGAGT-A;Accumulated SNP # 0 S AHRE9-5-F10       AATCCGAGTTA;Accumulated SNP # 0 S AHRE9-5-C11       CATTCGAGTTA;Accumulated SNP # 0 S AHRE9-5-A10       ACTCCGAGTTA;Accumulated SNP # 0 S AHRE9-5-F9        C-TCCGAGTTA;Accumulated SNP # 0 S AHRE9-5-G8        C-TCCGAGTTA;Accumulated SNP # 0 S
Left:
Right:
AGTTACAATGATATAATCTGGTCTTCCATTTTTATAAAGCAGGCGTGCATTAGACTGGACCCAAGTCCATCG

GTTGTTTTTTGTAAGAAGCCGGA-

AAACTATCATGCCACTTTCTCCANTCTTAATCACTAAAATAAAATTAAAWA---

ATTAAATTATCAAACCCCCAAATC-AATATAGTAAAGATTATTCCTAAAA

Do you want to choose this into SNP data? [y/n] n
************************************************************************
========================================================================
```

Now consider the text window below which shows an alignment produced by the software. Note the small numbers at the end of most of the lines (most are 0, some 1; one 17, one 22). When a discrepancy in the last two sequences having a quality score on the borderline is seen, and the number of "Accumulated SNPs" is high as it is shown in the last two lines, the discrepancy can be ignored as the large number indicates that the sequence is of poor quality. This inference is good because real SNPs occur at a frequency of about 1 in 200 letters and the high numbers are much greater than one would expect If it were not for these numbers, one would have to go and look at the sequence trace file to see if the discrepancy was real or not Using this technique, it has never been observed that a discrepancy in a sequence with a large Accumulated SNP number turns out to be a real SNP upon visual inspection of the trace data. Thus, time can be saved by avoiding to have to regularly view such trace data.

```
                 S13462.DPG-51-CP1  ACAATCCTTAA;Accumulated SNP #: 0 S

S13462.DPG-90-CP1  ACAATCCTTAA;Accumulated SNP #: 0 S

S13462.DPG-92-CP1  ACAATCCTTAA;Accumulated SNP #: 0 S

S13462.DPG-83-CP1  ACAATCCTTAA;Accumulated SNP #: 0 S

S13462.DPG-75-CP1  ACAATCCTTAA;Accumulated SNP #: 0 S

S13462.DPG-22-CP1  ACAATCCTTAA;Accumulated SNP #: 0 S

S13462.DPG-37-CP1  ACAATCCTTAA;Accumulated SNP #: 0 S

S13462.DPG-96-CP1  ACAATCCTTAA;Accumulated SNP #: 1 S
```

```
                                        -continued
S13462.DPG-93-CP1 ACAATCCTTAA;Accumulated SNP #: 1 S S13462.DPG-12-CP1 ACAATCCTTAA;Accumulated SNP #: 1 S S13462.DPG-20-CP1 ACAATCCTTAA;Accumulated SNP #: 0 S S13462.DPG-59-CP1 ACAATCCTTAA;Accumulated SNP #: 0 S S13462.DPG-86-CP1 ACAATCCTTAA;Accumulated SNP #: 0 S S13462.DPG-16-CP1 ACAATCCTTAA;Accumulated SNP #: 1 S S13462.DPG-19-CP1 ACAATCCT-A-;Accumulated SNP #: 1 S S13462.DPG-42-CP1 ACAAACCT-----;Accumulated SNP #: 17 S S13462.DPG-14-CP1 ACAAACCTTAT;Accumulated SNP #: 22 S
Indicator          ^
mar 204 404
Right Margin
Left:
CTCAGGTCCCACAGCAACAATATCATTCAAACTGGAATTAAAACATACACACATAATATATAAGGTGAAGGT

ATTGAACATTACAGGATTATTAACTGGCATTCCTCACTGTCTATTCCTAAAATCAAGATGTGGGATGGAGCCTTCGT

GCT
AGCTATAATGGAACACAATTAATATGAAATTAGTCCTGCCGATACAAT

Right: CTTAAAGGGCGAATTCGTTTAAACCTGCAGGACTAG--------------------------------
---
---
Quality Values for Minor :::
18
Total No of minor charaters quality is less than 21 is 1
Total No of minor charaters quality is greater than 21 is 0
Do you want to choose this into SNP data? [y/n]
==============================================================================
```

The inventive software has several useful features which distinguish it from other programs that use phred quality control data to find reliable discrepancies:

1) Other phred-based programs simply present the discrepancies that show a phred value above some arbitrary number. The problem is that it is quite common to find discrepancies with letters having quality values. Take the example below:

```
                    TAATTC

ATATAT

TAATTC

TAATTC
```

Note that the second sequence is "shifted" relative to the other three due to one single sequencing mistake called an insertion, which is common. The alignment program is not perfect and does not always make the correct alignment by shifting the sequences relative to one another. Even though the quality values for the letters A, T, A, A, T and T are very good, they are not SNPs but rather sequencing/alignment errors. Most other programs would output these letters as good candidate SNPs, so if the end-user did not go back to the data to inspect it valuable time and expense would be incurred by designing genotyping experiments based on incorrect data.

The inventive program avoids this by visually presenting a local neighborhood of sequences to the end-user for those discrepancies that meet the phred threshold value. In other words, the program presents a block of sequences (such as the one above) so that an experienced user can recognize common errors such as this shift error.

Other common errors the end-user might notice are discrepancies in strings of sequence (such as GGGGG), or a phenomena called "bleedthrough". A conventional program relying just on phred score would select those mistakes and bad experiments would subsequently be designed. Since the inventive program shows the local sequence around this region for all the sequences, it is obvious to a trained molecular biologist that the finding by the software is incorrect and should be discarded.

So one advantage of the software is that it presents a snapshot of the data, along with a query line asking if the user wishes to accept the data or not, so that invaluable human input is included in the SNP discovery analysis.

2) Another advantage is that the precise position and sequence that the discrepancy occurs is readily apparent to the user. The example output above shows how this data is presented. Notice that each discrepancy is advantageously identified by using k="column number". This is important in case the end-user wants to call up the sequence data electropherogram, since it tells him which one to call up and where to go to see the relevant base. This is often done in different windows on the desktop. Visual inspection of raw DNA sequence data is the most reliable method of determining whether a discrepancy is valid. While the purpose of software is to eliminate such time consuming steps, in some cases borderline quality values require visual inspection. The presentation of the precise position and relevant file names for a discrepancy makes this step easy to perform.

3) Another advantage is that the end-user can specify a quality control value for a run of the program, then go back and repeat the run using a different quality control value. The quality for a position that meets the threshold requirements is also reported to the user so that borderline cases can be further reviewed.

4) Yet even another advantage is that the program presents the neighboring 200 letters of average sequence (for all of the individuals in an analysis) in front of and behind candidate SNP locations. This is important because when submitting SNP locations to a SNP consumables company (e.g., Orchid), one must submit the neighboring sequence as well so that the kit can be designed to assay this SNP in thousands of people.

5) Finally, another advantage is that the user can visualize deletion mutations, which do not have corresponding phred values. A unique attribute is afforded the software because of this functionality. The program can recognize reliable base deletion polymorphisms and present them to the user for visual inspection. In conventional programs, if a discrepancy is a deleted base there is no quality control information to check since no data is produced for a non-base or deleted base (and there is consequently no phred value for the deleted base). This would eliminate the discovery of single base deletion polymorphisms. Deletion polymorphisms are common and, since the goal is to thoroughly document the various genetic haplotypes in a population, a SNP finding program that can recognize deletion polymorphisms offers competitive advantages. Not knowing all of the variants in a gene sequence causes the resolution of haplotype-based studies to be sub-optimal, compared to being able to recognize all of the variants.

In an alternate embodiment, the software does not use actual DNA sequence data files or chromatograms but rather accepts and utilizes sequence information in text format which is freely available and downloadable from publicly available databases. For quality control, an indirect measure of quality is used. For example, any discrepancy that occurs within a bleedthrough region, or within the neighborhood of discrepancy clusters is ignored.

It should be readily apparent and understood that the foregoing description is only illustrative of the invention and in particular provides preferred embodiments thereof. Various alternatives and modifications can be devised by those skilled in the art without departing from the true spirit and scope of the invention. E.g., gene data from human, animal, plant, or other may be utilized in connection with the methods. Accordingly, the present invention is intended to embrace all such alternatives, modifications, and variations which fall within the scope of the appended claims.

What is claimed is:

1. A method of processing gene sequence data with use of one or more computers, the method comprising:

reading, by the computer, gene sequence data corresponding to a gene sequence and coding sequence data corresponding to a plurality of coding sequences within the gene sequence;

identifying, by the computer following a set of primer selection rules, primer pair data within the gene sequence data, the primer pair data corresponding to a pair of primer sequences for one of the coding sequences, the set of primer selection rules including a first rule specifying that the primer pair data for the coding sequence be obtained for a predetermined annealing temperature;

the set of primer selection rules including a second rule specifying that, based on a comparison of the primer pair data and gene family data, wherein the gene family data represents a gene family member of the gene sequence other than the gene sequence, stored in a file, the primer pair data for the coding sequence must fail to match the gene family data;

storing the primer pair data;

repeating the acts of identifying and storing such that primer pair data are obtained for each coding sequence of the plurality of coding sequences at the predetermined annealing temperature; and simultaneously amplifying the plurality of coding sequences in gene sequences from three or more individuals at the predetermined annealing temperature using the identified pairs of primer sequences, such that a plurality of amplified coding sequences from the three or more individuals are obtained.

2. The method of claim 1, wherein the first rule further specifies that each primer sequence have a length that falls within one or more predetermined ranges of lengths.

3. The method of claim 1, wherein the set of primer selection rules includes a third rule specifying that a single primer pair be identified for two coding regions if one coding region is within a predetermined number of nucleotide base identifiers from the other coding region.

4. The method of claim 1, further comprising:
sequencing the plurality of amplified coding sequences to produce a plurality of nucleotide base identifier strings.

5. The method of claim 4, wherein the plurality of nucleotide base identifier strings includes nucleotide base identifiers represented by the letters G, A, T, and C.

6. The method of claim 5, further comprising:
positionally aligning, by the computer, the plurality of nucleotide base identifier strings to produce a plurality of aligned nucleotide base identifier strings.

7. The method of claim 6, further comprising:
performing, by the computer, a comparison amongst aligned nucleotide base identifiers at each nucleotide base position of the plurality of aligned nucleotide base identifier strings.

8. The method of claim 7, performing the following additional acts at each nucleotide base position where a difference amongst aligned nucleotide base identifiers exists:

reading, by the computer, nucleotide base quality information associated with the aligned nucleotide base identifiers where the difference exists;

comparing, by the computer, the nucleotide base quality information with predetermined qualification data;

visually displaying, from the computer, the nucleotide base quality information for acceptance or rejection; and if the nucleotide base quality information meets the predetermined qualification data and is accepted: providing and storing resulting data that identifies where the difference amongst the aligned base identifiers exists.

9. The method of claim 8, wherein the resulting data comprise single nucleotide polymorphism (SNP) identification data.

10. The method of claim 8, wherein the nucleotide base quality information comprise one or more phred values.

11. The method of claim 9, wherein after providing and storing all resulting data that identifies where the differences amongst the aligned nucleotide base identifiers exist, performing the following additional acts for each aligned nucleotide base identifier at each nucleotide base position where a difference exists:

comparing, by the computer, the nucleotide base identifier with a predetermined nucleotide base identifier to identify whether the nucleotide base identifier is a variant; and providing and storing, by the computer, additional resulting data that identifies whether the nucleotide base identifier is a variant.

12. The method of claim 11, wherein the additional resulting data comprises haplotype identification data.

13. The method of claim 12, wherein providing and storing additional resulting data comprises providing and storing a binary value of '0' for those nucleotide base identifiers that are identified as variants and a binary value of '1' for those nucleotide base identifiers that are not.

14. A computer program product comprising:
a computer-usable storage medium;
computer-readable program code embodied on said computer-usable storage medium; and
the computer-readable program code for effecting the following acts on a computer:
  reading gene sequence data corresponding to a gene sequence and coding sequence data corresponding to a plurality of coding sequences within the gene sequence;
  identifying primer pair data within the gene sequence data by following a set of primer selection rules, the primer pair data corresponding to a pair of primer sequences for one of the coding sequences,
  the set of primer selection rules including a first rule specifying that the primer pair data for the coding sequence be obtained for a predetermined annealing temperature;
  the set of primer selection rules including a second rule specifying that, based on a comparison of the primer pair data and gene family data, wherein the gene family data represents a gene family member of the gene sequence other than the gene sequence, stored in a file, the primer pair data for the coding sequence must fail to match the gene family data;
  storing the primer pair data; and
  repeating the acts of identifying and storing such that primer pair data are obtained for each coding sequence of the plurality of coding sequences at the predetermined annealing temperature, so that the plurality of coding sequences can be simultaneously amplified in gene sequences from three or more of individuals at the predetermined annealing temperature using the identified pairs of primer sequences to produce a plurality of amplified coding sequences from the three or more individuals.

15. The computer program product of claim 14, wherein the first rule further specifies that each primer sequence have a length that falls within one or more predetermined ranges of lengths.

16. The computer program product of claim 14, wherein the set of primer selection rules includes a third rule specifying that a single primer pair be identified for two coding regions if one coding region is within a predetermined number of nucleotide base identifiers from the other coding region.

17. The computer program product of claim 14, wherein the plurality of amplified coding sequences are sequenced to produce a plurality of nucleotide base identifier strings.

18. The computer program product of claim 17, wherein the plurality of nucleotide base identifier strings includes nucleotide base identifiers represented by the letters G, A, T, and C.

19. The computer program product of claim 18, wherein the computer-readable program code is for effecting the following further acts on the computer:
  positionally aligning the plurality of nucleotide base identifier strings to produce a plurality of aligned nucleotide base identifier strings.

20. The computer program product of claim 19, wherein the computer-readable program code is for effecting the following further acts on the computer:
  performing a comparison amongst aligned nucleotide base identifiers at each nucleotide base position of the plurality of aligned nucleotide base identifier strings.

21. The computer program product of claim 20, wherein the computer-readable program code is for effecting the following additional acts at each nucleotide base position where a difference amongst aligned nucleotide base identifiers exists:
  reading nucleotide base quality information associated with the aligned nucleotide base identifiers where the difference exists;
  comparing the nucleotide base quality information with predetermined qualification data;
  visually displaying the nucleotide base quality information for acceptance or rejection; and
  if the nucleotide base quality information meets the predetermined qualification data and is accepted: providing and storing resulting data that identifies where the difference amongst the aligned base identifiers exists.

22. The computer program product of claim 21, wherein the resulting data comprise single nucleotide polymorphism (SNP) identification data.

23. The computer program product of claim 21, wherein the nucleotide base quality information comprise one or more phred values.

24. The computer program product of claim 22, wherein after providing and storing all resulting data that identifies where the differences amongst the aligned nucleotide base identifiers exist, performing the following additional acts for each aligned nucleotide base identifier at each nucleotide base position where such difference exists:
  comparing the nucleotide base identifier with a predetermined nucleotide base identifier to identify whether the nucleotide base identifier is a variant; and
  providing and storing additional resulting data that identifies whether the nucleotide base identifier is a variant.

25. The computer program product of claim 24, wherein the additional resulting data comprises haplotype identification data.

26. The computer program product of claim 25, wherein providing and storing additional resulting data comprises providing and storing a binary value of '0' for those nucleotide base identifiers that are identified as variants and a binary value of '1' for those nucleotide base identifiers that are not.

* * * * *

SEQUENCE LISTING

<160> NUMBER OF SEQ ID NOS: 239

<210> SEQ ID NO 1
<211> LENGTH: 480
<212> TYPE: DNA
<213> ORGANISM: Homo Sapiens

<400> SEQUENCE: 1
gaattctttc cagaaggctt tccatttact tttcctagat tcatcagaag aatcattatc    60
tacagcagct gtaactgatt gaaatgtatt ttatgaacaa taagacttga aagttaaaat   120
tgctccttta tccatgtact gaagaataaa tattgtgaaa gcagtcataa aaacagaagt   180
aatcttttgg tacctctgca ttagaactct ttattaacca ggtgtattgc cattcaacag   240
taatattttg aaaggaatct ctattttga gcaggtttca acttctgctt tttattttaa   300
acagtagact tgaaatattc agtaaccatg ctataaagag ctatgctgta agacagcttt   360
ttctatttat agagcatggt tttgaaatta taacaaagca tgggttttat cctgaaatca   420
ttcataaata acacgtacca aaactttaat acgggctagc cagtgtgagc cagtgtgacg   480

<210> SEQ ID NO 2
<211> LENGTH: 22
<212> TYPE: DNA
<213> ORGANISM: Homo Sapiens

<400> SEQUENCE: 2
ttccagaagg ctttccattt ac                                             22

<210> SEQ ID NO 3
<211> LENGTH: 21
<212> TYPE: DNA
<213> ORGANISM: Homo Sapiens

<400> SEQUENCE: 3
gttcaagtct tggtacgtgc t                                              21

```
<210> SEQ ID NO 4
<211> LENGTH: 780
<212> TYPE: DNA
<213> ORGANISM: Homo Sapiens

<400> SEQUENCE: 4
gaattctttc cagaaggctt tccatttact tttcctagat tcatcagaag aatcattatc      60
tacagcagct gtaactgatt gaaatctatt ttatgaacaa taagacttga aagttaaaat     120
tgctccttta tccatgtact gaagaataaa tattgtgaaa gcagtcataa aaacagaagt     180
aatcttttgg tacctctgca ttagaactct ttattaacca ggtgtattgc cattcaacag     240
taatattttg aaaggaatct ctattttga gcaggtttca acttctgctt tttattttaa     300
acagtagact tgaaatattc agtaaccatg ctataaagag ctatgctgta agacagcttt     360
ttctatttat agagcatggt tttgaaatta aacaaagca tgggttttat cctgaaatca     420
tgctccttta tccatgtact gaagaataaa tattgtgaaa gcagtcataa aaacagaagt     480
aatcttttgg tacctctgca ttagaactct ttattaacca ggtgtattgc cattcaacag     540
taatattttg aaaggaatct ctattttga gcaggtttca acttctgctt tttattttaa     600
acagtagact tgaaatattc agtaaccatg ctataaagag ctatgctgta agacagcttt     660
ttctatttat agagcatggt tttgaaatta aacaaagca tgggttttat cctgaaatca     720
tgctccttg tccatgtact gaagaataaa tattgtgaaa gcagtcataa aaacagaagt     780

<210> SEQ ID NO 5
<211> LENGTH: 510
<212> TYPE: DNA
<213> ORGANISM: Homo Sapiens

<400> SEQUENCE: 5
aatcttttgg tacctctgca ttagaactct ttattaacca ggtgtattgc cattcaacag      60
taatattttg aaaggaatct ctattttga gcaggtttca acttctgctt tttattttaa     120
acagtagact tgaaatattc agtaaccatg ctataaagag ctatgctgta agacagcttt     180
ttctatttat agagcatggt tttgaaatta aacaaagca tgggttttat cctgaaatca     240
tgctccttta tccatgtact gaagaataaa tattgtgaaa gcagtcataa aaacagaagt     300
aatcttttgg tacctctgca ttagaactct ttattaacca ggtgtattgc cattcaacag     360
taatattttg aaaggaatct ctattttga gcaggtttca acttctgctt tttattttaa     420
acagtagact tgaaatattc agtaaccatg ctataaagag ctatgctgta agacagcttt     480
ttcataaata gcacgtacca agacttgaac                                      510

<210> SEQ ID NO 6
<211> LENGTH: 22
<212> TYPE: DNA
<213> ORGANISM: Homo Sapiens

<400> SEQUENCE: 6
ttccagaagg ctttccattt ac                                               22

<210> SEQ ID NO 7
<211> LENGTH: 21
<212> TYPE: DNA
<213> ORGANISM: Homo Sapiens

<400> SEQUENCE: 7
ggtacctctg cattagaact c                                                21
```

```
<210> SEQ ID NO 8
<211> LENGTH: 21
<212> TYPE: DNA
<213> ORGANISM: Homo Sapiens

<400> SEQUENCE: 8
gttcaagtct tggtacgtgc t                                              21

<210> SEQ ID NO 9
<211> LENGTH: 22
<212> TYPE: DNA
<213> ORGANISM: Homo Sapiens

<400> SEQUENCE: 9
ttgcatgttg caaatgatgt cc                                             22

<210> SEQ ID NO 10
<211> LENGTH: 20
<212> TYPE: DNA
<213> ORGANISM: Homo Sapiens

<400> SEQUENCE: 10
caacccaggt catcgttcac                                                20

<210> SEQ ID NO 11
<211> LENGTH: 21
<212> TYPE: DNA
<213> ORGANISM: Homo Sapiens

<400> SEQUENCE: 11
cctctcaagc acattgatca c                                              21

<210> SEQ ID NO 12
<211> LENGTH: 21
<212> TYPE: DNA
<213> ORGANISM: Homo Sapiens

<400> SEQUENCE: 12
tatactgatc tgagctgagg c                                              21

<210> SEQ ID NO 13
<211> LENGTH: 22
<212> TYPE: DNA
<213> ORGANISM: Homo Sapiens

<400> SEQUENCE: 13
taacattcac actaatggca gc                                             22

<210> SEQ ID NO 14
<211> LENGTH: 20
<212> TYPE: DNA
<213> ORGANISM: Homo Sapiens

<400> SEQUENCE: 14
tgcttctcct ctagaggctg                                                20

<210> SEQ ID NO 15
<211> LENGTH: 240
<212> TYPE: DNA
<213> ORGANISM: Homo Sapiens

<400> SEQUENCE: 15
```

```
aacttagcaa acacatgatc ttgtatatag tagacatcat tattgttttc ccctctattc    60 ttctttttcaa tttctgaatc ataaggattg cctgagccta ggagatcaag gccagccttg   120
gcaacatggc gaaatgccat ctctacaaaa aaaaaaaaaa aaattatcta ggtgtggtgg   180
caagcaccag tggtcccagc tactcagaag gctgaggtgg gaggattgct tgagcccagg   240
```

<210> SEQ ID NO 16
<211> LENGTH: 420
<212> TYPE: DNA
<213> ORGANISM: Homo Sapiens

<400> SEQUENCE: 16

```
agtagagtgc tggcatactc agtaagacta tattgaataa atgaatgaat aaccccagaa    60
taaaaatgta actataaatg tgttatccta ggtctcaaat cagaatgatc tgaaagttag   120 gaaaccccccc tgccactgca gagatctcat cttactttta tgtcctatta taatgggaga   180
ctatggcaag aaattttga tatctacaga atagatctct attttggacca attttcatct   240 ttgtttgatt caataaacag gctaagttct acttacgaag cctataaaac tccaaaactc   300
caaatatcca catattccta aatatgtcac ctaactctaa tacatataca acatgatgag   360
tacacatcct gtccattttc aagaacttat gcactcatca ctgtacacct tgatatctag   420
```

<210> SEQ ID NO 17
<211> LENGTH: 3360
<212> TYPE: DNA
<213> ORGANISM: Homo Sapiens

<400> SEQUENCE: 17

```
agttaatgca cacagtttgg ctagttttgg cttcaaaatt aattaaactg tatcaatgta    60
ttttgaagtg ttaagtcatc tgtatgcttt agctccttct atagatgagg caaatataca   120
aacagattaa actgactttt acagaataat tattctttta ccttgtttac atggaaagga   180
atcctccatt ttaggatgca cataaaatgc cagcctatgt tgatgacatt gccttaacac   240
ttttttttta agtaattta cagggtagtt aacctgtaaa agaaacagtg gataaacttg   300
aaaatgctaa tagcaaaaaa cacttcagcc atggcacata caaccagaag ccaatgatat   360
ccttcaacta tagaaattag cggtgttttc tgtttattcc tgaagcagga ttccatattc   420
aagccagaaa ttgtcattca acagaaaaaa tcaggtcaaa acaatcaatc acataatgta   480
gcaagacaaa agtatgtgct tatgtgaaga aaaacaaaaa caacaaataa ccgaactttt   540
attttcttga atataatatt gatggcaaga ttgctaagag gtcatccctg tatttagttt   600
agataaaggc ttccagcata gaacactgtt aagaagtaac tgtcaggagc tatgcagaag   660
tgatgagagg caaataatat aaaaactaga aaagcaggtt ttaattttct atagacttta   720
ttacacatta ttatgttacg agacaaatgc agataattct taatttatca aatttgtgag   780
cttaattaac aaaaatattt gaccctcacc agaaaaacag ataactctaa atctactctg   840
aaaatctaat caattgcgaa gtattaccta tttggagact atgtattata tcaaagataa   900
agctactatt ctcacagaac atatggggtc attggcagcc aaccaataat gaagtaaata   960
ttctaatatt tgggaaaata ctgagaaaac taataaattg tcctggatat tatttattct  1020
tgcctttaca aaagacttac acatccaaat gagattagtt tagaatagag gttttagtt  1080 cagaaaatgt tcaaagtcca atacagtcat ggctaatcag agactagaga accttataa  1140 aggtaagtag gctgaaaac ccttggaaac tgagcagtct tattttgaac tagcatgttt  1200
taatcaaagg tatggaatta atcaaatatc aattaagaat tactggaatg cacactcatg  1260
```

```
ccaaatgaca actaacatgt tatttcctac tatgatgact ctttgatttg agtcagatgg    1320
cataaaaaaa tattgctagc tatacaataa attttactct tctgcttctg ctctctaaag    1380
aaaaatctta ttttttcaca taagaagctc atggaatcga atgttaatta agaaaagat     1440 agggtaagta caactggggg aaagacagta cctctaatta cataggaaat ccatgaaaga    1500
attaatcatc ataagagaag aatcatttt ccagtagccc cactaccatg aatgatattt     1560
tcatgagcct cggccacctt ctccaatgga tattgagaac ctatcacagg tttcaaccag    1620
ccaatttcca ttccagcttg aagggctgct gcatattgct gaaattcctc ctaagaaaag    1680 gaaaacaaa tttctttttg tagtgaaccg tatgatttaa ttttcagaag cattaaaaac     1740
acttcagaat ctaagtgtta taccatgaag agtctcttac aaatgtgtga cttttgtcaa    1800
cttgtccaga actatagaaa agtagttat ctacagggta accataaatc ccatctgcct     1860
gagacagtgt tagtgtacaa atacctgtt gtcctgaaat tattactagt atcacatttc     1920
tatctcaaaa ggtatgctta cctggatata aattatactg tcaccctagt tgtccttctg    1980
gtgactaatc cttaccaact cccactagtc atataactaa gtttaacatc tattcaaact    2040
ttcagcttgc ctgagtaggc aaactgtacc aatgtttaag ttaccaaaat cagaagtact    2100
tcttttccta ccttggttga ggaaaagaga gtaactccaa ttatactcga ctcctttgcc    2160
atggtgtctc gtgggtttat ttcaatagta cctctgctgc caacaaccta acatgaaaaa    2220
cagcaattct acagttaaag attactgtaa aatagtgtta aattgtggta aaacattaaa    2280
gtggtaaaaa aaaaaaaaag aaaaggaata cttactatca ctcgtcctcc atgtgacaga    2340
agactcaagt ctttactaag atttacatta gctaacattt caataattat atcaattcct    2400
ttctcaccaa catacttcta tataataaaa gagaaatgta gagtaagata gcaagtgaaa    2460
aactgtaaaa tagctactat ctgtacaaga tattatagaa atatgtttca aatgatatat    2520 aaaatgctaca tctttgagac taataatgca aaattttaaa taatctaatt atataatcac    2580
gatgtaattc caaggtacca gccagaacat ctaaactgat aaaaatttgt actaaataca    2640
ttgctgtagt gaaataaagt ttgtctggaa ttttcaggtg ctagactcaa cttgagtata    2700
aaatacttag ctgaaaattt tctatctgta aaataaactt tcataaagaa acaataaatc    2760
aaaagcccca aaccccagg gggctcccat ttttattaat aaacaaaaag caaagaaga     2820 tatcattagc tgttcggttt tgcatgattt ttgttgtttt agtgcatttg gttttgttct    2880
aaatggttta tcatctgttt gatgcactaa ctcttttggg ctcttggatg ttggacgctg    2940
gctcttacaa aaagctacac acatctacat tatattcatt ttattttaac acacacacac    3000
aaatgaatcc ctgtgcccgg gattgcacta ggtaccagga atacaaatac aaacataggg    3060
agctcaaaac aaaactagtg agaaagatgg gaaatactac agtcatagct ataaagtaat    3120
gggctaagta acacattagc agaaataaat catagaatac agagaaaaaa ggttaaggtt    3180
tgattgcctg ccatggtcag ataaagttcc acagagacga tgaactgggc cctcagggat    3240
gaataggagt ttcccaagcc aaaagaaagg aaaatgagta aggggaagct agacctgagg    3300
ctgagtcagt ctggaccaaa gaaacagaaa agcaaagatg gagggactg agaacacaag     3360
```

<210> SEQ ID NO 18
<211> LENGTH: 2460
<212> TYPE: DNA
<213> ORGANISM: Homo Sapiens

<400> SEQUENCE: 18

| | |
|---|---|
| taacgggcca ttttttcatct ttgtgaatat tcttggataa tggtatcagc agtgctagat | 60 |
| cttaggttcc ccagacgtat aacaaaggag tgcttttgtt cggcttttg gcaagatgat | 120 |
| tgcaaaaaag gtaataaact ctcactctta ttttttcctt catttgtaat gatctaattt | 180 |
| acacagtact caatatttgg gaattctaa tctccccaac gtgaggaagt ggttgaggat | 240 |
| tagcaaagca ataagtgttt agcaaattgc taatatagta caagtgaaga acttcagaat | 300 |
| ctgcttgaat tctgttaaat gcagcaacta aataaatgcc acctcaccat tttggatgca | 360 |
| gtagtgatta ttcctccaaa gcatccagct aacaaatgaa ctttattccc tgggccacac | 420 |
| agatccagtt tgtaatttac agatatctca ccttccatgg agaattcaca tcagtagaaa | 480 |
| ttatattaag aatacctcac agctgcaaat acaaagctgc agctttactt agaatgttat | 540 |
| ttgcattaaa aaatcaattt ttatagctct aagattctag agaagctata ttctatttaa | 600 |
| tacacataaa caatacaaaa atgatagtaa agtttaaaa cttagacatc tgttttttaa | 660 |
| ataaattaaa gttttaaaac acgcataaaa attcatcgca ctgaaaaaag gaagcaaaca | 720 |
| gctttaaagg agtagttggt taaaaacata ttaaaaaacc acgcaagtct ccaaggaaca | 780 |
| aagtttgact tttgtaaaac agtggaaaat tttaccttaa ttttatcaat gtaattcact | 840 |
| tctctgtgat tgaacacttc atgggctcca ttttgcaaaa caatcttttg tccttcctca | 900 |
| gtaccagcag tgcccaaaat ctttaagcca taagctctag caatttggca tgctgctaat | 960 |
| ccaacctgaa aaacaaatat aacccaagag ttatatattc tctacactcc tgtaaacact | 1020 |
| taaatacata caatgaactt aagattccta taggacccac cctaaccttta aggaacttaa | 1080 |
| gagtgtaaat aagaaataa gaaaaacagc taactttaat tgagcattta aaatattcca | 1140 |
| ggaaccatac taaataattt ctacatattg ttttattcta tcctcacaat gaccctataa | 1200 |
| agtagatact attattgtcc ctattgtaca gataagaaag ttgaagcttc aaattataag | 1260 |
| taatttggcc aagtcatatg cggagatgga acaggagtt agaccagtct gactgcagaa | 1320 |
| cttgagtttt taaccactgc atcaagatgt ttgcagggtt taaagatgat cagaacatgc | 1380 |
| tctctgactt ctttgtgcat atgaaattct aaataacaaa tgtaaggcct ccaccattta | 1440 |
| agtagaagag ataggtatat gggcaaatta actaattcat ccatatggtg aatgtttata | 1500 |
| gagtgtttac gatgtgctag acatggtact taatgtaaga aataaactta tattctaagg | 1560 |
| gtggaggaag ataatagtca tatgaatgaa taaaataaat tcaggaaata aaagtgctaa | 1620 |
| gaaaaaataa gactggctgt tgggttaaag agacaggaat aggggctatt taggtcatca | 1680 |
| ggaagagcca ctctgaaaaa atgagacctg aaaaagtga ggaacaagcc acgagaacat | 1740 |
| ccggtcagcc acgtggagga tgctgtgggc atagtgaatg gccatggcta acctggcgag | 1800 |
| gtgggaatgc agttggggtc aaagaacaga aagagggca gtgtgtctca gggaggggcg | 1860 |
| tgtacgaaag ggtcgaagat gaggccagaa aggccaagtc acacagaatc tgagggggtga | 1920 |
| gggtagaggc ttccgagtat attaaaacct gtgcagaacc acgggagagc ttaagccagg | 1980 |
| aaatgatctg gttgactcag gctttaaaaa ggttgctcca attacatgtg aggcacaaag | 2040 |
| aaagcggtga ggaaaatggg aggaggaaga tcagtttgta gctgttagaa cagtctagat | 2100 |
| aagagatgaa gctggcttga acaaggtgg tggcactgga aaaataaac aaattcagat | 2160 |
| atagtttaga ggtaagctaa tgggacttcc tcacagattg aatgcgggag atgaggaaaa | 2220 |
| gagaaaaata caggctgtct cctatgtctt tggccagatt aactgggtag agtgagaaga | 2280 |
| ctggagaaca ctaagtttgt gaaaatctcc agatttcact ttgccaagtg tggtggcgca | 2340 |
| tgcctgtaat cccagctatg tgggaggctg aggcaggagg atcgcttggg cccaggaatt | 2400 | tgaggagttt gggattgcag tgatcatgcc actgcactcc agtctgggca acggagcaag    2460

<210> SEQ ID NO 19
<211> LENGTH: 2520
<212> TYPE: DNA
<213> ORGANISM: Homo Sapiens

<400> SEQUENCE: 19
atccagtgac agagttcatg tggatttctt gttaaattct aactgcagag ctctaacttt      60
tccctctaag ctcctgagag gcagattggc agctagtttc tcgaagaggt ttctgacagc     120
cctgcattgg gtgatttcat tgaagggctt attttaagtt ctgagtcctc ctcccccatt     180
cccccacatt agcattttca gccatgggtt gtggtgttaa ggacagggct gtatacgtgc     240
actccatgga tgtcatcaaa gtgcagcagg caagcagcag aagggagata aaggactaa      300 gaattcacag tgtggctta ccgtgctgtc tggggcaaca taggtaagct ttaatgagcc     360
ttagtttcct tatctaaggg aatatggaat taatatcaac cttaaagaac tgtttaaaat     420
tctaaataaa tatttttata acatatgcta cttgaaggca aaacaaggc cagtttatct     480 tagtctacac ccaatacagg tggaaaatct aacatatttt tgaagggtg ctctgttgag      540 tttattaacc aagaaatgct aaactaatga caaaacatca ccttcagaag accaaaatca     600
aaagttttac tacataaaga aaaaagcac ctttgactct atttataaat ctgactttta      660 aaatgacca aaggaactat aatgtgaaac ccataaaccc aagcttgttt caaaatacat      720 taaaaaaat acttactcct ccacttgccc catgaaccag aacactctct ccagctttca     780
cacaggcact gcaaaggaaa gcataagtta catcaccta ttttttgaag ctaattaatc     840
tcgggtgttt tcatcatctt aaggaattc taccctagt ctggctaaca cttacacaaa      900
cagcaaatgc aacctgacat acagccccaa atattcccta agctccacag aataaacaaa     960
gccttcaatt catttattcc ttgaacaaat atttattggg agtctttatg ttccaggcac    1020
tatgctgctg gacactggga tgactatgtg gtgctacttc tgagtggcta cagtccttgt    1080
gggttgtgaa gtaaaattgc tgagcctgga ggatctggaa tctctcattc ccatatatcc    1140
cccacagaaa gggcctcaaa gcaggtttat tatatagctc agtctttatt ctgtggtcta    1200
gagtaatgtc caagtaaaca cagtagctat ttttttttgcc caaggaaaga aagaaatttt    1260
tcttctccat gtctctgaac atcaggttgc accagccttg tactctttca gggaggaatg    1320
ctgagttagc aaaggtcaga gagtaggaaa tgcaataaat tctatcacaa agattcccat    1380
gtcatccccc tgaaatgtcc agattctctg gtgaaatggc attttctttt tacttccagt    1440
tcacatgact acttttctag tatgtactga aagaaggga catgcagcaa ggcatgaggg    1500
gatgcctcac tattccagat ggacggtgcc aatgtcaaaa gccagcagat gctgtgagat    1560
ccagatctga ctctcaggaa ggctctctta cttcctcaaa caatgtgggg tggccacact    1620
gcagagacat tatagaacat tatgctccac ctgggaaaga gaacagtaac cagagtcctg    1680 ctccagcta tgcaccaaca gctgagaagt ggcaacaatg agcaataagt gaagcttttct   1740 cccacactct tgcttagagc tgaagggact gaggacaata tgttaaagta aaacataaac    1800
ataaggggat aggatgacta gtgttaaact atgggtatg aaatacctcc caagaaaatt     1860
tttcaaaaat tcttataaga tgcccctcaa acactaaaga cacattctca taaatccctg    1920
gggcctgggg tgagggggaga aaaagcaggc aaatcccctc ctgaatcctt gcacagagtc    1980
gctgtgacag ttaattttat gtgtcaactt gactgggcca aggaacccaa tatttgttcc    2040

| | |
|---|---|
| aacattactc tgttacagaa acagtgtttt ttttttttt cgaatgagat taacaatgga | 2100 |
| atagctggat tttgagtaaa gcagatgacc ctctagaatg tgggtgggcc tcatccaatc | 2160 |
| agttgaaggc ttttgttttc aaagactgac ctccgatgag caagagtaaa ttcagccagc | 2220 |
| aaactttcta tggacttaaa ctgcacctct tccttgtgtc tcccatctgc tggcccaccg | 2280 |
| caacagattt tagactcacc agtcctccac aatttcatgg gtcaactctt taaaatcaat | 2340 |
| caatctgtgt gcgcgtgtgt gtgtgtgtgt gtgtatgtgt acagagtgac tgattcttaa | 2400 |
| ggaatttata tagagataaa tgatagatca gatcaaatag aagatcaaat agatagatga | 2460 |
| ttgactgata gatagacaga cagacacaca tcccgttgtt tgtttctctg gagaaccctg | 2520 |

<210> SEQ ID NO 20
<211> LENGTH: 384
<212> TYPE: DNA
<213> ORGANISM: Homo Sapiens
<220> FEATURE:
<221> NAME/KEY: allele
<222> LOCATION: 369
<223> OTHER INFORMATION: n can be a, c, g, or t

<400> SEQUENCE: 20

| | |
|---|---|
| acagacagag atagacagag gcagagtcag ggagaggcag agaaagaaag agaacaagaa | 60 |
| agcttaaaga tagtccaaac gcaaagctgt ctttaaaaaa tgcatactct attactggca | 120 |
| acaaagtttt ataatctata cattttatga accactaatc cttaatttat tcaagatcac | 180 |
| aacaggggac tcatattata gagtcaagta aatatcatta ccaacatttt atttaacagt | 240 |
| ttgtcctcct taattacatg gagaatgata tagtgactcc ttcatgcctt ttttctcct | 300 |
| taacaagcca tatgcaggaa agtttccatg ctgcgcaaac ataaaagaaa gttatatttc | 360 |
| attcctaana gaaaactgaa aagc | 384 |

<210> SEQ ID NO 21
<211> LENGTH: 2460
<212> TYPE: DNA
<213> ORGANISM: Homo Sapiens

<400> SEQUENCE: 21

| | |
|---|---|
| agtttggcta gttttggctt caaaattaat taaactgtat caatgtattt tgaagtgtta | 60 |
| agtcatctgt atgctttagc tccttctata gatgaggcaa atatacaaac agattaaact | 120 |
| gacttttaca gaataattat tcttttacct tgtttacatg gaaaggaatc ctccatttta | 180 |
| ggatgcacat aaaatgccag cctatgttga tgacattgcc ttaacacttt tttttttaagt | 240 |
| aattttacag ggtagttaac ctgtaaaaga aacagtggat aaacttgaaa atgctaatag | 300 |
| caaaaaacac ttcagccatg gcacatacaa ccagaagcca atgatatcct tcaactatag | 360 |
| aaattagcgg tgttttctgt ttattcctga agcaggattc catattcaag ccagaaattg | 420 |
| tcattcaaca gaaaaaatca ggtcaaaaca atcaatcaca taatgtagca agacaaaagt | 480 |
| atgtgcttat gtgaagaaaa acaaaaacaa caaataaccg aactttttatt ttcttgaata | 540 |
| taatattgat ggcaagattg ctaagaggtc atccctgtat ttagtttaga taaaggcttc | 600 |
| cagcatagaa cactgttaag aagtaactgt caggagctat gcagaagtga tgagaggcaa | 660 |
| ataatataaa aactagaaaa gcaggttttaa attttctata gactttatta cacattatta | 720 |
| tgttacgaga caaatgcaga taattcttaa tttatcaaat ttgtgagctt aattaacaaa | 780 |
| aatatttgac cctcaccaga aaaacagata actctaaatc tactctgaaa atctaatcaa | 840 |
| ttgcgaagta ttacctatttt ggagactatg tattatatca aagataaagc tactattctc | 900 |

```
acagaacata tggggtcatt ggcagccaac caataatgaa gtaaatattc taatatttgg      960
gaaaatactg agaaaactaa taaattgtcc tggatattat ttattcttgc ctttacaaaa     1020
gacttacaca tccaaatgag attagtttag aatagaggtt tttagttcag aaaatgttca     1080
aagtccaata cagtcatggc taatcagaga ctagagaacc tttataaagg taagtaggct     1140
tgaaaaccct tggaaactga gcagtcttat tttgaactag catgttttaa tcaaaggtat     1200
ggaattaatc aaatatcaat taagaattac tggaatgcac actcatgcca atgacaact     1260
aacatgttat ttcctactat gatgactctt tgatttgagt cagatggcat aaaaaaatat     1320
tgctagctat acaataaatt ttactcttct gcttctgctc tctaaagaaa atcttattt     1380
tttcacataa gaagctcatg gaatcgaatg ttaattaaag aaaagatagg gtaagtacaa     1440
ctgggggaaa gacagtacct ctaattacat aggaaatcca tgaaagaatt aatcatcata     1500
agagaagaat catttttcca gtagccccac taccatgaat gatattttca tgagcctcgg     1560
ccaccttctc caatggatat tgagaaccta tcacaggttt caaccagcca atttccattc     1620
cagcttgaag ggctgctgca tattgctgaa attcctccta agaaaggaa aaacaaattt      1680
ctttttgtag tgaaccgtat gatttaattt tcagaagcat taaaaacact tcagaatcta     1740
agtgttatac catgaagagt ctcttacaaa tgtgtgactt ttgtcaactt gtccagaact     1800
atagaaaaag tagttatcta cagggtaacc ataaatccca tctgcctgag acagtgttag     1860
tgtacaaaat acctgttgtc ctgaaattat tactagtatc acatttctat ctcaaaaggt     1920
atgcttacct ggatataaat tatactgtca ccctagttgt ccttctggtg actaatcctt     1980
accaactccc actagtcata taactaagtt taacatctat tcaaactttc agcttgcctg     2040
agtaggcaaa ctgtaccaat gtttaagtta ccaaaatcag aagtacttct tttcctacct     2100
tggttgagga aaagagagta actccaatta tactcgactc ctttgccatg gtgtctcgtg     2160
ggtttatttc aatagtacct ctgctgccaa caacctaaca tgaaaacag caattctaca     2220
gttaaagatt actgtaaaat agtgttaaat tgtggtaaaa cattaaagtg gtaaaaaaaa     2280
aaaaaagaaa aggaatactt actatcactc gtcctccatg tgacagaaga ctcaagtctt     2340
tactaagatt tacattagct aacatttcaa taattatatc aattcctttc tcaccaacat     2400
acttctatat aataaagag aaatgtagag taagatagca agtgaaaaac tgtaaaatag      2460
```

<210> SEQ ID NO 22
<211> LENGTH: 21
<212> TYPE: DNA
<213> ORGANISM: Homo Sapiens

<400> SEQUENCE: 22
tatgcagaag tgatgagagg c                                                21

<210> SEQ ID NO 23
<211> LENGTH: 21
<212> TYPE: DNA
<213> ORGANISM: Homo Sapiens

<400> SEQUENCE: 23
gcctctcatc acttctgcat a                                                21

<210> SEQ ID NO 24
<211> LENGTH: 21
<212> TYPE: DNA
<213> ORGANISM: Homo Sapiens

```
<400> SEQUENCE: 24
tactggaatg cacactcatg c                                             21

<210> SEQ ID NO 25
<211> LENGTH: 21
<212> TYPE: DNA
<213> ORGANISM: Homo Sapiens

<400> SEQUENCE: 25
gcatgagtgt gcattccagt a                                             21

<210> SEQ ID NO 26
<211> LENGTH: 1809
<212> TYPE: DNA
<213> ORGANISM: Homo Sapiens

<400> SEQUENCE: 26
tggaatcgaa tgttaattaa agaaaagata gggtaagtac aactggggga aagacagtac     60
ctctaattac ataggaaatc catgaaagaa ttaatcatca taagagaaga atcatttttc    120
cagtagcccc actaccatga atgatatttt catgagcctc ggccaccttc tccaatggat    180
attgagaacc tatcacaggt ttcaaccagc caatttccat tccagcttga agggctgctg    240
catattgctg aaattcctcc taagaaaagg aaaaacaaat ttcttttttgt agtgaaccgt    300 atgatttaat tttcagaagc attaaaaaca cttcagaatc taagtgttat accatgaaga    360
gtctcttaca aatgtgtgac ttttgtcaac ttgtccagaa ctatagaaaa agtagttatc    420
tacagggtaa ccataaatcc catctgcctg agacagtgtt agtgtacaaa atacctgttg    480
tcctgaaatt attactagta tcacatttct atctcaaaag gtatgcttac ctggatataa    540
attatactgt cacctagtt gtccttctgg tgactaatcc ttaccaactc ccactagtca    600
tataactaag tttaacatct attcaaactt tcagcttgcc tgagtaggca aactgtacca    660
atgtttaagt taccaaaatc agaagtactt cttttcctac cttggttgag gaaaagagag    720
taactccaat tatactcgac tcctttgcca tggtgtctcg tgggtttatt tcaatagtac    780
ctctgctgcc aacaacctaa catgaaaaac agcaattcta cagttaaaga ttactgtaaa    840
atagtgttaa attgtggtaa aacattaaag tggtaaaaaa aaaaaaaaga aaaggaatac    900
ttactatcac tcgtcctcca tgtgacagaa gactcaagtc tttactaaga tttacattag    960
ctaacatttc aataattata tcaattcctt tctcaccaac atacttctat ataataaaag   1020
agaaatgtag agtaagatag caagtgaaaa actgtaaaat agctactatc tgtacaagat   1080
attatagaaa tatgtttcaa atgatatata aatgctacat ctttgagact aataatgcaa   1140 aatttttaaat aatctaatta tataatcacg atgtaattcc aaggtaccag ccagaacatc   1200
taaactgata aaaatttgta ctaaatacat tgctgtagtg aaataaagtt tgtctggaat   1260
tttcaggtgc tagactcaac ttgagtataa aatacttagc tgaaaatttt ctatctgtaa   1320
aataaacttt cataaagaaa caataaatca aaagccccaa accccagggg ggctcccatt   1380
tttattaata aacaaaaagc aaaagaagat atcattagct gttcggtttt gcatgatttt   1440 tgttgttttta gtgcatttgg ttttgttcta aatggtttat catctgtttg atgcactaac   1500
tcttttgggc tcttggatgt tggacgctgg ctcttacaaa aagctacaca catctacatt   1560
atattcattt tatttttaaca cacacacaca aatgaatccc tgtgcccggg attgcactag   1620
gtaccaggaa tacaaataca aacatagggga gctcaaaaca aaactagtga gaaagatggg   1680
aaatactaca gtcatagcta taaagtaatg ggctaagtaa cacattagca gaaataaatc   1740
```

```
atagaataca gagaaaaaag gttaaggttt gattgcctgc catggtcaga taaagttcca    1800
cagagacga                                                            1809

<210> SEQ ID NO 27
<211> LENGTH: 20
<212> TYPE: DNA
<213> ORGANISM: Homo Sapiens

<400> SEQUENCE: 27
gcttgcctga gtaggcaaac                                                  20

<210> SEQ ID NO 28
<211> LENGTH: 20
<212> TYPE: DNA
<213> ORGANISM: Homo Sapiens

<400> SEQUENCE: 28
gtttgcctac tcaggcaagc                                                  20

<210> SEQ ID NO 29
<211> LENGTH: 21
<212> TYPE: DNA
<213> ORGANISM: Homo Sapiens

<400> SEQUENCE: 29
tgtaattcca aggtaccagc c                                                21

<210> SEQ ID NO 30
<211> LENGTH: 21
<212> TYPE: DNA
<213> ORGANISM: Homo Sapiens

<400> SEQUENCE: 30
ggctggtacc ttggaattac a                                                21

<210> SEQ ID NO 31
<211> LENGTH: 1650
<212> TYPE: DNA
<213> ORGANISM: Homo Sapiens

<400> SEQUENCE: 31
tgattgcaaa aaaggtaata aactctcact cttattttttt ccttcatttg taatgatcta     60
atttacacag tactcaatat ttgggaaatt ctaatctccc caacgtgagg aagtggttga    120
ggattagcaa agcaataagt gtttagcaaa ttgctaatat agtacaagtg aagaacttca    180
gaatctgctt gaattctgtt aaatgcagca actaaataaa tgccacctca ccattttgga    240
tgcagtagtg attattcctc caaagcatcc agctaacaaa tgaactttat tccctgggcc    300
acacagatcc agtttgtaat ttacagatat ctcaccttcc atggagaatt cacatcagta    360
gaaattatat taagaatacc tcacagctgc aaatacaaag ctgcagcttt acttagaatg    420
ttatttgcat taaaaatca attttttatag ctctaagatt ctagagaagc tatattctat    480
ttaatacaca taaacaatac aaaaatgata gtaaagtttt aaaacttaga catctgtttt    540
ttaaataaat taagttttta aaacacgcat aaaaattcat cgcactgaaa aaggaagca    600 aacagcttta aaggagtagt tggttaaaaa catattaaaa aaccacgcaa gtctccaagg    660
aacaaagttt gactttgta aaacagtgga aaatttacc ttaatttat caatgtaatt    720 cacttctctg tgattgaaca cttcatgggc tccattttgc aaaacaatct tttgtccttc    780
```

-continued

```
ctcagtacca gcagtgccca aaatctttaa gccataagct ctagcaattt ggcatgctgc    840
taatccaacc tgaaaaacaa atataaccca agagttatat attctctaca ctcctgtaaa    900
cacttaaata catacaatga acttaagatt cctataggac ccaccctaac tttaaggaac    960
ttaagagtgt aaatgaagaa ataagaaaaa cagctaactt taattgagca tttaaaatat   1020
tccaggaacc atactaaata atttctacat attgttttat tctatcctca caatgaccct   1080
ataaagtaga tactattatt gtccctattg tacagataag aaagttgaag cttcaaatta   1140
taagtaattt ggccaagtca tatgcggaga tggaaacagg agttagacca gtctgactgc   1200
agaacttgag ttttaaccca ctgcatcaag atgtttgcag ggtttaaaga tgatcagaac   1260
atgctctctg acttctttgt gcatatgaaa ttctaaataa caaatgtaag gcctccacca   1320
tttaagtaga agagataggt atatgggcaa attaactaat tcatccatat ggtgaatgtt   1380
tatagagtgt ttacgatgtg ctagacatgg tacttaatgt aagaaataaa cttatattct   1440
aagggtggag gaagataata gtcatatgaa tgaataaaat aaattcagga aataaaagtg   1500
ctaagaaaaa ataagactgg ctgttgggtt aaagagacag gaatagggggc tatttaggtc   1560 atcaggaaga gccactctga aaaatgaga cctgaaaaaa gtgaggaaca agccacgaga   1620
acatccggtc agccacgtgg aggatgctgt                                    1650
```

<210> SEQ ID NO 32
<211> LENGTH: 21
<212> TYPE: DNA
<213> ORGANISM: Homo Sapiens

<400> SEQUENCE: 32

```
gcaagtctcc aaggaacaaa g                                              21
```

<210> SEQ ID NO 33
<211> LENGTH: 21
<212> TYPE: DNA
<213> ORGANISM: Homo Sapiens

<400> SEQUENCE: 33

```
ctttgttcct tggagacttg c                                              21
```

<210> SEQ ID NO 34
<211> LENGTH: 21
<212> TYPE: DNA
<213> ORGANISM: Homo Sapiens

<400> SEQUENCE: 34

```
gatggaaaca ggagttagac c                                              21
```

<210> SEQ ID NO 35
<211> LENGTH: 21
<212> TYPE: DNA
<213> ORGANISM: Homo Sapiens

<400> SEQUENCE: 35

```
ggtctaactc ctgtttccat c                                              21
```

<210> SEQ ID NO 36
<211> LENGTH: 1557
<212> TYPE: DNA
<213> ORGANISM: Homo Sapiens

<400> SEQUENCE: 36

```
attctaactg cagagctcta acttttccct ctaagctcct gagaggcaga ttggcagcta    60
```

-continued

```
gtttctcgaa gaggtttctg acagccctgc attgggtgat tcattgaag ggcttatttt      120 aagttctgag tcctcctccc ccattccccc acattagcat tttcagccat gggttgtggt      180
gttaaggaca gggctgtata cgtgcactcc atggatgtca tcaaagtgca gcaggcaagc      240
agcagaaggg agatagaagg actaagaatt cacagtgtgg ctttaccgtg ctgtctgggg      300
caacataggt aagctttaat gagccttagt ttccttatct aagggaatat ggaattaata      360
tcaaccttaa agaactgttt aaaattctaa ataaatattt ttataacata tgctacttga      420
aggcaaaaac aaggccagtt tatcttagtc tacacccaat acaggtggaa aatctaacat      480
atttttgaag gggtgctctg ttgagtttat taaccaagaa atgctaaact aatgacaaaa      540
catcaccttc agaagaccaa aatcaaaagt tttactacat aaagaaaaaa agcacctttg      600
actctattta taaatctgac ttttaaaaat gaccaaagga actataatgt gaaacccata      660
aacccaagct tgtttcaaaa tacattaaaa aaaatactta ctcctccact tgccccatga      720
accagaacac tctctccagc tttcacacag gcactgcaaa ggaaagcata agttacatca      780
ccttattttt tgaagctaat taatctcggg tgttttcatc atcttaagga atttctaccc      840
ctagtctggc taacacttac acaaacagca aatgcaacct gacatacagc cccaaatatt      900
ccctaagctc cacagaataa acaaagcctt caattcattt attccttgaa caaatattta      960
ttgggagtct ttatgttcca ggcactatgc tgctggacac tgggatgact atgtggtgct     1020
acttctgagt ggctacagtc cttgtgggtt gtgaagtaaa attgctgagc ctggaggatc     1080
tggaatctct cattcccata tatccccac agaaagggcc tcaaagcagg tttattatat      1140
agctcagtct ttattctgtg gtctagagta atgtccaagt aaacacagta gctattttt      1200 ttgcccaagg aaagaaagaa attttttcttc tccatgtctc tgaacatcag gttgcaccag     1260
ccttgtactc tttcagggag gaatgctgag ttagcaaagg tcagagagta ggaaatgcaa     1320
taaattctat cacaaagatt cccatgtcat ccccctgaaa tgtccagatt ctctggtgaa     1380
atggcatttt cttttactt ccagttcaca tgactacttt tctagtatgt actgaaaaga      1440
agggacatgc agcaaggcat gagggggatgc ctcactattc cagatggacg gtgccaatgt     1500
caaaagccag cagatgctgt gagatccaga tctgactctc aggaaggctc tcttact        1557
```

<210> SEQ ID NO 37
<211> LENGTH: 21
<212> TYPE: DNA
<213> ORGANISM: Homo Sapiens

<400> SEQUENCE: 37

```
gtgaaaccca taaacccaag c                                                 21
```

<210> SEQ ID NO 38
<211> LENGTH: 21
<212> TYPE: DNA
<213> ORGANISM: Homo Sapiens

<400> SEQUENCE: 38

```
gcttgggttt atgggtttca c                                                 21
```

<210> SEQ ID NO 39
<211> LENGTH: 21
<212> TYPE: DNA
<213> ORGANISM: Homo Sapiens

<400> SEQUENCE: 39

```
ctccatgtct ctgaacatca g                                              21

<210> SEQ ID NO 40
<211> LENGTH: 21
<212> TYPE: DNA
<213> ORGANISM: Homo Sapiens

<400> SEQUENCE: 40
ctgatgttca gagacatgga g                                              21

<210> SEQ ID NO 41
<211> LENGTH: 21
<212> TYPE: DNA
<213> ORGANISM: Homo Sapiens

<400> SEQUENCE: 41
actgtggaaa cagccagtag a                                              21

<210> SEQ ID NO 42
<211> LENGTH: 21
<212> TYPE: DNA
<213> ORGANISM: Homo Sapiens

<400> SEQUENCE: 42
tcttgataac ctcgctgtgt c                                              21

<210> SEQ ID NO 43
<211> LENGTH: 20
<212> TYPE: DNA
<213> ORGANISM: Homo Sapiens

<400> SEQUENCE: 43
atgtgccacc ctctatccag                                                20

<210> SEQ ID NO 44
<211> LENGTH: 23
<212> TYPE: DNA
<213> ORGANISM: Homo Sapiens

<400> SEQUENCE: 44
ttagagatga tgaataaagc tcc                                            23

<210> SEQ ID NO 45
<211> LENGTH: 21
<212> TYPE: DNA
<213> ORGANISM: Homo Sapiens

<400> SEQUENCE: 45
cccagcctaa cagttctttt g                                              21

<210> SEQ ID NO 46
<211> LENGTH: 20
<212> TYPE: DNA
<213> ORGANISM: Homo Sapiens

<400> SEQUENCE: 46
ccactacgct cggccaattt                                                20

<210> SEQ ID NO 47
<211> LENGTH: 21
<212> TYPE: DNA
<213> ORGANISM: Homo Sapiens

<400> SEQUENCE: 47
```
aagagaacag taactcccgt c 21

<210> SEQ ID NO 48
<211> LENGTH: 21
<212> TYPE: DNA
<213> ORGANISM: Homo Sapiens

<400> SEQUENCE: 48
cagcactgat tccatgcata c 21

<210> SEQ ID NO 49
<211> LENGTH: 21
<212> TYPE: DNA
<213> ORGANISM: Homo Sapiens

<400> SEQUENCE: 49
gccagaagtt gtaggttcaa g 21

<210> SEQ ID NO 50
<211> LENGTH: 21
<212> TYPE: DNA
<213> ORGANISM: Homo Sapiens

<400> SEQUENCE: 50
ctttactcag tcccaagctc t 21

<210> SEQ ID NO 51
<211> LENGTH: 20
<212> TYPE: DNA
<213> ORGANISM: Homo Sapiens

<400> SEQUENCE: 51
gcgtgacaca tagcaagtgc 20

<210> SEQ ID NO 52
<211> LENGTH: 21
<212> TYPE: DNA
<213> ORGANISM: Homo Sapiens

<400> SEQUENCE: 52
gccagttctt caatagtacc c 21

<210> SEQ ID NO 53
<211> LENGTH: 21
<212> TYPE: DNA
<213> ORGANISM: Homo Sapiens

<400> SEQUENCE: 53
gagaagaacc tttgccaatg g 21

<210> SEQ ID NO 54
<211> LENGTH: 21
<212> TYPE: DNA
<213> ORGANISM: Homo Sapiens

<400> SEQUENCE: 54
ctccaccatt actctcacca a 21

<210> SEQ ID NO 55
<211> LENGTH: 21
<212> TYPE: DNA
<213> ORGANISM: Homo Sapiens

```
-continued

<400> SEQUENCE: 55
tgcctgtata ccgggatata c                                              21

<210> SEQ ID NO 56
<211> LENGTH: 22
<212> TYPE: DNA
<213> ORGANISM: Homo Sapiens

<400> SEQUENCE: 56
ttgacaaagg tatactgctg ga                                             22

<210> SEQ ID NO 57
<211> LENGTH: 20
<212> TYPE: DNA
<213> ORGANISM: Homo Sapiens

<400> SEQUENCE: 57
cttctgtctc cacaccttcc                                                20

<210> SEQ ID NO 58
<211> LENGTH: 20
<212> TYPE: DNA
<213> ORGANISM: Homo Sapiens

<400> SEQUENCE: 58
ggagaggtga gagagagatg                                                20

<210> SEQ ID NO 59
<211> LENGTH: 22
<212> TYPE: DNA
<213> ORGANISM: Homo Sapiens

<400> SEQUENCE: 59
aattgtttct cctactaccc tc                                             22

<210> SEQ ID NO 60
<211> LENGTH: 22
<212> TYPE: DNA
<213> ORGANISM: Homo Sapiens

<400> SEQUENCE: 60
aacccatctc aaagatttag gc                                             22

<210> SEQ ID NO 61
<211> LENGTH: 22
<212> TYPE: DNA
<213> ORGANISM: Homo Sapiens

<400> SEQUENCE: 61
aatgcctgta ttgaattgca gg                                             22

<210> SEQ ID NO 62
<211> LENGTH: 21
<212> TYPE: DNA
<213> ORGANISM: Homo Sapiens

<400> SEQUENCE: 62
taaaaccagt cttgggcttg g                                              21

<210> SEQ ID NO 63
<211> LENGTH: 1300
<212> TYPE: DNA
<213> ORGANISM: Homo Sapiens
```

<220> FEATURE:
<221> NAME/KEY: allele
<222> LOCATION: 1,2,3
<223> OTHER INFORMATION: n can be a, c, g, or t

<400> SEQUENCE: 63

| | |
|---|---|
| nnnattcagt accaaattta ctgtggaaac agccagtaga gaatacaaga aaatgttcaa | 60 |
| acaggcaagt aaataagtgt cttgtacctt aatgataaat ggtagtagta tagccattta | 120 |
| taatggcatt aatgattggt ttaatttaac ataatttata agctattgaa gtatggaaaa | 180 |
| ttataagcat atatattagg ttattaggac tcataaattt atgttattta cttccagttt | 240 |
| gtgagatgac ttgaattttt catgtttcct attctttact tccatagaca tggatggata | 300 |
| atatgggaag agctggtgag atggaactca agcccttcaa tggagaagat tatacatgta | 360 |
| tcacctttca gcctgatttg tctaagttta aaatgcaaag cctggacaaa gatattgttg | 420 |
| cactaatggt cagaagagca tatgatattg ctggatccac caaagatgtc aaagtctttc | 480 |
| ttaatggaaa taaactgcca tgagtatttt cctggatgtt aaggataata agggattttg | 540 |
| taatcattgt caagtgcaaa attgaatttt tcccctccc atatgttttt gtttgtttgt | 600 |
| ttgtttgttt gtttgagaca gagtctcaca ctgttgcccg ggctggagtg cagtggcacg | 660 |
| atctcggctc accgcaacct ccacctccca ggttcacgca attctcctgc ctcagcctcc | 720 |
| caagtagctg ggattacagg tgcctgccac cacacctggc taattttttg tattttttagt | 780 |
| agagacaggt ttcactatgt tggccaggct ggtctcgaac accagacctc atgatccacc | 840 |
| cgtcttggcc tcccaaagtg ctgggattac aggcatgagc cactgcacct ggcccaacca | 900 |
| tatgtatttt cttaccactt ctcacatatg ttcttgaaaa gagaatggta tgccacattt | 960 |
| tttaatcagc tcattttaaa cttaccgaag gaatttcttt ctcaaagaaa cacctaaaat | 1020 |
| aaatatttca tgtccttttt ttatttcct ttttctttct tttcttgata acctcgctgt | 1080 |
| gtcacccagg ctggagtaca gtgatgcaat cacggctcac tacagcctgg acctcccagg | 1140 |
| ctcaagcgat catcccacct cagcttctgg agtagctgga aatgcaggca gcaccaccat | 1200 |
| gcccagctaa ttttttttt tctttttaat agaggtgggg atctcactat gttgcccagg | 1260 |
| ctggtcttga actcctgggc tcaagtgatc cacccacctc | 1300 |

<210> SEQ ID NO 64
<211> LENGTH: 21
<212> TYPE: DNA
<213> ORGANISM: Homo Sapiens

<400> SEQUENCE: 64
tcttgataac ctcgctgtgt c          21

<210> SEQ ID NO 65
<211> LENGTH: 21
<212> TYPE: DNA
<213> ORGANISM: Homo Sapiens

<400> SEQUENCE: 65
ttgataacct cgctgtgtca c          21

<210> SEQ ID NO 66
<211> LENGTH: 20
<212> TYPE: DNA
<213> ORGANISM: Homo Sapiens

<400> SEQUENCE: 66

```
gataacctcg ctgtgtcacc                                              20

<210> SEQ ID NO 67
<211> LENGTH: 20
<212> TYPE: DNA
<213> ORGANISM: Homo Sapiens

<400> SEQUENCE: 67
ataacctcgc tgtgtcaccc                                              20

<210> SEQ ID NO 68
<211> LENGTH: 20
<212> TYPE: DNA
<213> ORGANISM: Homo Sapiens

<400> SEQUENCE: 68
caggctggag tacagtgatg                                              20

<210> SEQ ID NO 69
<211> LENGTH: 20
<212> TYPE: DNA
<213> ORGANISM: Homo Sapiens

<400> SEQUENCE: 69
aggctggagt acagtgatgc                                              20

<210> SEQ ID NO 70
<211> LENGTH: 21
<212> TYPE: DNA
<213> ORGANISM: Homo Sapiens

<400> SEQUENCE: 70
ctggagtaca gtgatgcaat c                                            21

<210> SEQ ID NO 71
<211> LENGTH: 21
<212> TYPE: DNA
<213> ORGANISM: Homo Sapiens

<400> SEQUENCE: 71
ggagtacagt gatgcaatca c                                            21

<210> SEQ ID NO 72
<211> LENGTH: 21
<212> TYPE: DNA
<213> ORGANISM: Homo Sapiens

<400> SEQUENCE: 72
gagtacagtg atgcaatcac g                                            21

<210> SEQ ID NO 73
<211> LENGTH: 21
<212> TYPE: DNA
<213> ORGANISM: Homo Sapiens

<400> SEQUENCE: 73
agtacagtga tgcaatcacg g                                            21

<210> SEQ ID NO 74
<211> LENGTH: 20
<212> TYPE: DNA
<213> ORGANISM: Homo Sapiens

<400> SEQUENCE: 74
```

```
cagtgatgca atcacggctc                                              20

<210> SEQ ID NO 75
<211> LENGTH: 20
<212> TYPE: DNA
<213> ORGANISM: Homo Sapiens

<400> SEQUENCE: 75
gtgatgcaat cacggctcac                                              20

<210> SEQ ID NO 76
<211> LENGTH: 20
<212> TYPE: DNA
<213> ORGANISM: Homo Sapiens

<400> SEQUENCE: 76
gcaatcacgg ctcactacag                                              20

<210> SEQ ID NO 77
<211> LENGTH: 20
<212> TYPE: DNA
<213> ORGANISM: Homo Sapiens

<400> SEQUENCE: 77
caatcacggc tcactacagc                                              20

<210> SEQ ID NO 78
<211> LENGTH: 20
<212> TYPE: DNA
<213> ORGANISM: Homo Sapiens

<400> SEQUENCE: 78
aatcacggct cactacagcc                                              20

<210> SEQ ID NO 79
<211> LENGTH: 20
<212> TYPE: DNA
<213> ORGANISM: Homo Sapiens

<400> SEQUENCE: 79
tcaagcgatc atcccacctc                                              20

<210> SEQ ID NO 80
<211> LENGTH: 20
<212> TYPE: DNA
<213> ORGANISM: Homo Sapiens

<400> SEQUENCE: 80
aagcgatcat cccacctcag                                              20

<210> SEQ ID NO 81
<211> LENGTH: 20
<212> TYPE: DNA
<213> ORGANISM: Homo Sapiens

<400> SEQUENCE: 81
gatcatccca cctcagcttc                                              20

<210> SEQ ID NO 82
<211> LENGTH: 20
<212> TYPE: DNA
<213> ORGANISM: Homo Sapiens
```

```
<400> SEQUENCE: 82
tcatcccacc tcagcttctg                                              20

<210> SEQ ID NO 83
<211> LENGTH: 20
<212> TYPE: DNA
<213> ORGANISM: Homo Sapiens

<400> SEQUENCE: 83
cacctcagct tctggagtag                                              20

<210> SEQ ID NO 84
<211> LENGTH: 20
<212> TYPE: DNA
<213> ORGANISM: Homo Sapiens

<400> SEQUENCE: 84
acctcagctt ctggagtagc                                              20

<210> SEQ ID NO 85
<211> LENGTH: 20
<212> TYPE: DNA
<213> ORGANISM: Homo Sapiens

<400> SEQUENCE: 85
ctcagcttct ggagtagctg                                              20

<210> SEQ ID NO 86
<211> LENGTH: 20
<212> TYPE: DNA
<213> ORGANISM: Homo Sapiens

<400> SEQUENCE: 86
tcagcttctg gagtagctgg                                              20

<210> SEQ ID NO 87
<211> LENGTH: 21
<212> TYPE: DNA
<213> ORGANISM: Homo Sapiens

<400> SEQUENCE: 87
cttctggagt agctggaaat g                                            21

<210> SEQ ID NO 88
<211> LENGTH: 21
<212> TYPE: DNA
<213> ORGANISM: Homo Sapiens

<400> SEQUENCE: 88
ttctggagta gctggaaatg c                                            21

<210> SEQ ID NO 89
<211> LENGTH: 20
<212> TYPE: DNA
<213> ORGANISM: Homo Sapiens

<400> SEQUENCE: 89
ggagtagctg gaaatgcagg                                              20

<210> SEQ ID NO 90
<211> LENGTH: 20
<212> TYPE: DNA
<213> ORGANISM: Homo Sapiens
```

```
<400> SEQUENCE: 90
gagtagctgg aaatgcaggc                                                     20

<210> SEQ ID NO 91
<211> LENGTH: 20
<212> TYPE: DNA
<213> ORGANISM: Homo Sapiens

<400> SEQUENCE: 91
gtagctggaa atgcaggcag                                                     20

<210> SEQ ID NO 92
<211> LENGTH: 20
<212> TYPE: DNA
<213> ORGANISM: Homo Sapiens

<400> SEQUENCE: 92
tagctggaaa tgcaggcagc                                                     20

<210> SEQ ID NO 93
<211> LENGTH: 20
<212> TYPE: DNA
<213> ORGANISM: Homo Sapiens

<400> SEQUENCE: 93
gggatctcac tatgttgccc                                                     20

<210> SEQ ID NO 94
<211> LENGTH: 20
<212> TYPE: DNA
<213> ORGANISM: Homo Sapiens

<400> SEQUENCE: 94
tctcactatg ttgcccaggc                                                     20

<210> SEQ ID NO 95
<211> LENGTH: 20
<212> TYPE: DNA
<213> ORGANISM: Homo Sapiens

<400> SEQUENCE: 95
gcctgggcaa catagtgaga                                                     20

<210> SEQ ID NO 96
<211> LENGTH: 20
<212> TYPE: DNA
<213> ORGANISM: Homo Sapiens

<400> SEQUENCE: 96
gcctgggcaa catagtgaga                                                     20

<210> SEQ ID NO 97
<211> LENGTH: 2208
<212> TYPE: DNA
<213> ORGANISM: Homo Sapiens

<400> SEQUENCE: 97
tgcctgccac cacacctggc taatttttg tattttagt agagacaggt ttcactatgt           60
tggccaggct ggtctcgaac accagacctc atgatccacc cgtcttggcc tcccaaagtg        120
ctgggattac aggcatgagc cactgcacct ggcccaacca tatgtatttt cttaccactt        180
```

-continued

```
ctcacatatg ttcttgaaaa gagaatggta tgccacattt tttaatcagc tcattttaaa      240
cttaccgaag gaatttcttt ctcaaagaaa cacctaaaat aaatatttca tgtccttttt      300 ttatttcct tttcttct tttcttgata acctcgctgt gtcacccagg ctggagtaca         360
gtgatgcaat cacggctcac tacagcctgg acctcccagg ctcaagcgat catcccacct      420
cagcttctgg agtagctgga aatgcaggca gcaccaccat gcccagctaa tttttttttt     480 tcttttaat agaggtgggg atctcactat gttgcccagg ctggtcttga actcctgggc      540
tcaagtgatc cacccacctc ggcctgtgtc ctttaatgac cattcccta tgcctatcag      600 tgaacatcat tgcattggtt ttggaaagtc ctcatagtct atcattgaac ctattttta     660 ataactttct taatactgtt acctttaatt cctgtacagg aaaggatttt cgtagttatg      720
tggacatgta tttgaaggac aagttggatg aaactggtaa ctccttgaaa gtaatacatg      780
aacaagtaaa ccacaggtgg gaagtgtgtt taactatgag tgaaaaaggc tttcagcaaa      840
ttagctttgt caacagcatt gctacatcca aggtaatttt attcttaaat tattaatcat      900
gatttatctt tacatatatg tgttcttatt gttttttaata tataaagtgg acttgaatat     960
tgggctagct tagtataaag gaggttaaat tagtttttaa tgtttgatta ttataatttt     1020
gaggatactg agttttacag tttggtattt ttccttatta gggtggcaga catgttgatt     1080
atgtagctga tcagattgtg actaaacttg ttgatgttgt gaagaagaag aacaagggtg     1140
gtgttgcagt aaaagcacat caggtatgtg cttttggcag ttttcttttt ctaaagtcaa     1200
ggaagaagag aaaggctata aataaagcat gagtacattt ttagtggctt aatatcaact     1260
tctattgcag gtgaaaaatc acatgtggat ttttgtaaat gccttaattg aaaacccaac     1320
ctttgactct cagacaaaag aaaacatgac tttacaaccc aagagctttg gatcaacatg     1380
ccaattgagt gaaaaattta tcaaagcttg agtacttaga ggaaaataaa aatagaaaca     1440
cctgacttta ttttccattg cacttcttag ctctgcagaa acaatgattc ttctcatagt     1500
gagcttctcc aagtcttccc aatctgaaaa ggaagtaaaa aagggcttta ctttaactga     1560
tttaccaaag acttaatgac cgtctatatt tcagtatttc ccaattacat tttaccatta     1620
agcttagatc acttttgaat taatctagct gtttaacaaa caccctcact taaatgccta     1680
agacttgctt tcagtcaaca catccaaaat tgaatttgtt acctccatac tcactgatt     1740 gcccatacaa gcagcccccc actctccaac aaaaaaacaa cttcctatct tagtaaaaag     1800
ccccaaccaa cctctaggtt gtataaacaa gaaagctggg agccttcctt tatttcccct     1860
cctctctaat ccggtcaata agaatcatct cttggatgct gcagtagctt ctcaccatta     1920
tctctttttt ggtttactac aataggttct taaccttcat actggttaag tcctttcctt     1980
ggaatgcttt tgagtgactt ttgtgttaaa acacccattt ttatcttcac tctcatttga     2040
aatctttcaa tgacttccac tcagggaaag tccaaattcc ataatttggc caacaagaaa     2100
gatctgctgt aatctaatta cacctacttc tccaactcat ctcagtgcca gttttcgta     2160 tattgtcctg ttgcttttaa attactgaaa agcacagtgc tcttcccc                 2208
```

<210> SEQ ID NO 98
<211> LENGTH: 21
<212> TYPE: DNA
<213> ORGANISM: Homo Sapiens

<400> SEQUENCE: 98

```
ccattccctt atgcctatca g                                                 21
```

```
<210> SEQ ID NO 99
<211> LENGTH: 21
<212> TYPE: DNA
<213> ORGANISM: Homo Sapiens

<400> SEQUENCE: 99
gaccattccc ttatgcctat c                                            21

<210> SEQ ID NO 100
<211> LENGTH: 20
<212> TYPE: DNA
<213> ORGANISM: Homo Sapiens

<400> SEQUENCE: 100
tcaagtgatc cacccacctc                                              20

<210> SEQ ID NO 101
<211> LENGTH: 20
<212> TYPE: DNA
<213> ORGANISM: Homo Sapiens

<400> SEQUENCE: 101
actcctgggc tcaagtgatc                                              20

<210> SEQ ID NO 102
<211> LENGTH: 20
<212> TYPE: DNA
<213> ORGANISM: Homo Sapiens

<400> SEQUENCE: 102
tgaactcctg ggctcaagtg                                              20

<210> SEQ ID NO 103
<211> LENGTH: 20
<212> TYPE: DNA
<213> ORGANISM: Homo Sapiens

<400> SEQUENCE: 103
cttgaactcc tgggctcaag                                              20

<210> SEQ ID NO 104
<211> LENGTH: 20
<212> TYPE: DNA
<213> ORGANISM: Homo Sapiens

<400> SEQUENCE: 104
aggctggtct tgaactcctg                                              20

<210> SEQ ID NO 105
<211> LENGTH: 20
<212> TYPE: DNA
<213> ORGANISM: Homo Sapiens

<400> SEQUENCE: 105
tcactatgtt gcccaggctg                                              20

<210> SEQ ID NO 106
<211> LENGTH: 20
<212> TYPE: DNA
<213> ORGANISM: Homo Sapiens

<400> SEQUENCE: 106
tcactatgtt gcccaggctg                                              20
```

```
<210> SEQ ID NO 107
<211> LENGTH: 21
<212> TYPE: DNA
<213> ORGANISM: Homo Sapiens

<400> SEQUENCE: 107
gcctaagact tgctttcagt c                                      21

<210> SEQ ID NO 108
<211> LENGTH: 21
<212> TYPE: DNA
<213> ORGANISM: Homo Sapiens

<400> SEQUENCE: 108
cctccatact cactgatttg c                                      21

<210> SEQ ID NO 109
<211> LENGTH: 21
<212> TYPE: DNA
<213> ORGANISM: Homo Sapiens

<400> SEQUENCE: 109
ctccatactc actgatttgc c                                      21

<210> SEQ ID NO 110
<211> LENGTH: 21
<212> TYPE: DNA
<213> ORGANISM: Homo Sapiens

<400> SEQUENCE: 110
tccatactca ctgatttgcc c                                      21

<210> SEQ ID NO 111
<211> LENGTH: 21
<212> TYPE: DNA
<213> ORGANISM: Homo Sapiens

<400> SEQUENCE: 111
cactgatttg cccatacaag c                                      21

<210> SEQ ID NO 112
<211> LENGTH: 21
<212> TYPE: DNA
<213> ORGANISM: Homo Sapiens

<400> SEQUENCE: 112
ctgatttgcc catacaagca g                                      21

<210> SEQ ID NO 113
<211> LENGTH: 21
<212> TYPE: DNA
<213> ORGANISM: Homo Sapiens

<400> SEQUENCE: 113
tgatttgccc atacaagcag c                                      21

<210> SEQ ID NO 114
<211> LENGTH: 20
<212> TYPE: DNA
<213> ORGANISM: Homo Sapiens

<400> SEQUENCE: 114
tttgcccata caagcagccc                                        20
```

<210> SEQ ID NO 115
<211> LENGTH: 20
<212> TYPE: DNA
<213> ORGANISM: Homo Sapiens

<400> SEQUENCE: 115
cccaaccaac ctctaggttg                                          20

<210> SEQ ID NO 116
<211> LENGTH: 21
<212> TYPE: DNA
<213> ORGANISM: Homo Sapiens

<400> SEQUENCE: 116
taaacaagaa agctgggagc c                                        21

<210> SEQ ID NO 117
<211> LENGTH: 20
<212> TYPE: DNA
<213> ORGANISM: Homo Sapiens

<400> SEQUENCE: 117
caagaaagct gggagccttc                                          20

<210> SEQ ID NO 118
<211> LENGTH: 20
<212> TYPE: DNA
<213> ORGANISM: Homo Sapiens

<400> SEQUENCE: 118
aagaaagctg ggagccttcc                                          20

<210> SEQ ID NO 119
<211> LENGTH: 21
<212> TYPE: DNA
<213> ORGANISM: Homo Sapiens

<400> SEQUENCE: 119
ctgggagcct tcctttattt c                                        21

<210> SEQ ID NO 120
<211> LENGTH: 21
<212> TYPE: DNA
<213> ORGANISM: Homo Sapiens

<400> SEQUENCE: 120
tgggagcctt cctttatttc c                                        21

<210> SEQ ID NO 121
<211> LENGTH: 21
<212> TYPE: DNA
<213> ORGANISM: Homo Sapiens

<400> SEQUENCE: 121
gaatcatctc ttggatgctg c                                        21

<210> SEQ ID NO 122
<211> LENGTH: 21
<212> TYPE: DNA
<213> ORGANISM: Homo Sapiens

<400> SEQUENCE: 122

| | | |
|---|---|---|
| atcatctctt ggatgctgca g | | 21 |

<210> SEQ ID NO 123
<211> LENGTH: 21
<212> TYPE: DNA
<213> ORGANISM: Homo Sapiens

<400> SEQUENCE: 123

| | | |
|---|---|---|
| atctcttgga tgctgcagta g | | 21 |

<210> SEQ ID NO 124
<211> LENGTH: 20
<212> TYPE: DNA
<213> ORGANISM: Homo Sapiens

<400> SEQUENCE: 124

| | | |
|---|---|---|
| ctcttggatg ctgcagtagc | | 20 |

<210> SEQ ID NO 125
<211> LENGTH: 20
<212> TYPE: DNA
<213> ORGANISM: Homo Sapiens

<400> SEQUENCE: 125

| | | |
|---|---|---|
| ggatgctgca gtagcttctc | | 20 |

<210> SEQ ID NO 126
<211> LENGTH: 20
<212> TYPE: DNA
<213> ORGANISM: Homo Sapiens

<400> SEQUENCE: 126

| | | |
|---|---|---|
| tgctgcagta gcttctcacc | | 20 |

<210> SEQ ID NO 127
<211> LENGTH: 21
<212> TYPE: DNA
<213> ORGANISM: Homo Sapiens

<400> SEQUENCE: 127

| | | |
|---|---|---|
| ctggttaagt cctttccttg g | | 21 |

<210> SEQ ID NO 128
<211> LENGTH: 21
<212> TYPE: DNA
<213> ORGANISM: Homo Sapiens

<400> SEQUENCE: 128

| | | |
|---|---|---|
| ttcaatgact tccactcagg g | | 21 |

<210> SEQ ID NO 129
<211> LENGTH: 21
<212> TYPE: DNA
<213> ORGANISM: Homo Sapiens

<400> SEQUENCE: 129

| | | |
|---|---|---|
| atgacttcca ctcagggaaa g | | 21 |

<210> SEQ ID NO 130
<211> LENGTH: 20
<212> TYPE: DNA
<213> ORGANISM: Homo Sapiens

<400> SEQUENCE: 130

-continued cttccactca gggaaagtcc                                          20

<210> SEQ ID NO 131
<211> LENGTH: 21
<212> TYPE: DNA
<213> ORGANISM: Homo Sapiens

<400> SEQUENCE: 131
ctcagggaaa gtccaaattc c                                        21

<210> SEQ ID NO 132
<211> LENGTH: 21
<212> TYPE: DNA
<213> ORGANISM: Homo Sapiens

<400> SEQUENCE: 132
tggccaacaa gaaagatctg c                                        21

<210> SEQ ID NO 133
<211> LENGTH: 21
<212> TYPE: DNA
<213> ORGANISM: Homo Sapiens

<400> SEQUENCE: 133
gccaacaaga aagatctgct g                                        21

<210> SEQ ID NO 134
<211> LENGTH: 21
<212> TYPE: DNA
<213> ORGANISM: Homo Sapiens

<400> SEQUENCE: 134
cacctacttc tccaactcat c                                        21

<210> SEQ ID NO 135
<211> LENGTH: 21
<212> TYPE: DNA
<213> ORGANISM: Homo Sapiens

<400> SEQUENCE: 135
cctacttctc caactcatct c                                        21

<210> SEQ ID NO 136
<211> LENGTH: 21
<212> TYPE: DNA
<213> ORGANISM: Homo Sapiens

<400> SEQUENCE: 136
cttctccaac tcatctcagt g                                        21

<210> SEQ ID NO 137
<211> LENGTH: 21
<212> TYPE: DNA
<213> ORGANISM: Homo Sapiens

<400> SEQUENCE: 137
ttctccaact catctcagtg c                                        21

<210> SEQ ID NO 138
<211> LENGTH: 20
<212> TYPE: DNA
<213> ORGANISM: Homo Sapiens -continued

<400> SEQUENCE: 138
ctccaactca tctcagtgcc                                                   20

<210> SEQ ID NO 139
<211> LENGTH: 20
<212> TYPE: DNA
<213> ORGANISM: Homo Sapiens

<400> SEQUENCE: 139
ccaactcatc tcagtgccag                                                   20

<210> SEQ ID NO 140
<211> LENGTH: 2580
<212> TYPE: DNA
<213> ORGANISM: Homo Sapiens

<400> SEQUENCE: 140

```
gatctcagtt cactgcaacc cgcgcctccc aggttaaagc aattctcctg cctcagcctc        60
ccaagcagct aggattacag ccatctcacc accaccatgc ctggctaccc tttttttttt       120
tttttttttt tttttgagac ggagtttcac ttttgtcacc caggctggag tgcaatggtg       180
cgatcttggc tcgctgcaac ctctacctcc tgggttcaag cgattctcct gcctcagcct       240
cccgagtagc tggaattaca ggtgcccacc accacgccag ctaattttg tattttagt         300
agagccgggg tttcgccatg ttggccaggc cggtctcaaa ctcctgacct caggtgttct       360
gcccaccttg gcctcctaaa gtgctgggat tataggcgtg agccaccgtg cctggtctaa       420
tttgttttaa ccactatatc tccaacaagt agctcagtgc tagcacaata taattatata       480
gtaaatattt attgaacgaa tgaaccaaaa ggagcagctc cctcagtggt gataacctga       540
catgggaaga tgtgccaccc tctatccaga aattattgtt ctacatcttt ttaattttg        600
aatcattttt atttgtatta aggctcattt gtattctaga tttctgatag atcccttctt       660
ccctaatatg atccctaata tgaatcttct cgttttcagg cattggctgt ggtattgtag       720
aaagcatact aaactgggtg aagtttaagg cccaagtcca gttaaacaag aagtgttcag       780
ctgtaaaaca taatagaatc aagggaattc ccaaactcga tgatgccaat gatgcaggta       840
tatatttaat aatgtttcca aacttttaag tcttatagtt gttatttat tcattaatgg        900
cataccacgg atatttattt ttcccttgac agaataacta tattcaacag ataacttgt        960
taaaaatcgg cccgtttcct attatggaag atttaggtca tttccatgtt ataaataata     1020
ttgaggtgat tattttggag tataaaacaa gaatgtttat attatgatct attacctaac     1080
aaataaattt gctcattata tagtaaattg tgttttatca caaggctata acagcatgt      1140
tcaagttagt atatttgagg ttgaactaaa tgtgctaata ttaatatgta tattttatt      1200
ttaggggggcc gaaactccac tgagtgtacg cttatcctga ctgagggaga ttcagccaaa    1260
actttggctg tttcaggcct tggtgtggtt gggagagaca aatatggggt tttccctctt    1320
agaggaaaaa tactcaatgt tcgagaagct tctcataagc aggtagaata taagacgatc    1380
ttcagaatct aaatctaatt tataatacaa gactttatgc ttatatttaa ttccctcatt     1440
aggcatttta aaatatattt tagacaattt gtgcttattt tgagaaatta ggtacattgt    1500
agcctatttt aacagacctt tctgatgtag taaattataa gctaatagct caaaatactg     1560
gagctcaaga aaatccaagc aacatatact gttaaatttc tttgttcttt tcaaatttat     1620
aaacgatgct ttttttggta tatgtccatt tcagatcatg gaaatgctg agattaacaa      1680
tatcatcaag attgtgggtc ttcagtacaa gaaaaactat gaagatgaag attcattgaa     1740
```

```
gacgcttcgt tatgggaaga taatgattat gacagatcag tcagatttgt tattaaattt    1800
ttagattgtt caactaaatt aagcatgtct taatttaatt tcattgtttt ttgccatgaa    1860 aataaaattac ttaaatagga gctttattca tcatctctaa tcaacatcta atcagatatg   1920
cttatatcat atgtatgttg caaatacagg ttaagtgagt ctggatttga acagacctttt  1980 tttgattccc atagaaaatt tgacaaattg ccagtaggtc agtcataata ttttttttatt  2040 tctaaacaat tctttgtttg tttgagatgg agtttcgccc ttgtcgccca ggctggagtg   2100
caatggtgca atcttggctc actgcaacct ccgcctcatg ggttcaagcg attctcctgc   2160
ctcagcctcc cgagtagctg ggattgcagg cggatgccac cacacccaac taatttttgt   2220
atttttagtg agacagggt ttcaccatgt tggccaggct ggtctcgaac gcctgacctc    2280
aggcgatccg cctgcctcgg cctcccaaag ttctgggatt acagatgtta gctaccacgc   2340
ccagcctaac agttcttttg aactttggct ttcaaatctt tctaggacca agatggttcc    2400
cacatcaaag gcttgctgat taattttatc catcacaact ggccctctct tctgcgacat   2460
cgttttctgg aggaatttat cactcccatt gtaaaggtac gctaatttct aagtaccatc    2520
atggatattt taagaccccta ctcctcaaac ctggatatac atataagccc cgtcacatgt  2580
```

<210> SEQ ID NO 141
<211> LENGTH: 20
<212> TYPE: DNA
<213> ORGANISM: Homo Sapiens

<400> SEQUENCE: 141
atgtgccacc ctctatccag                                                20

<210> SEQ ID NO 142
<211> LENGTH: 20
<212> TYPE: DNA
<213> ORGANISM: Homo Sapiens

<400> SEQUENCE: 142
atgtgccacc ctctatccag                                                20

<210> SEQ ID NO 143
<211> LENGTH: 21
<212> TYPE: DNA
<213> ORGANISM: Homo Sapiens

<400> SEQUENCE: 143
gagtgcaatg gtgcaatctt g                                              21

<210> SEQ ID NO 144
<211> LENGTH: 21
<212> TYPE: DNA
<213> ORGANISM: Homo Sapiens

<400> SEQUENCE: 144
caagattgca ccattgcact c                                              21

<210> SEQ ID NO 145
<211> LENGTH: 21
<212> TYPE: DNA
<213> ORGANISM: Homo Sapiens

<400> SEQUENCE: 145
caagattgca ccattgcact c                                              21

```
<210> SEQ ID NO 146
<211> LENGTH: 41
<212> TYPE: DNA
<213> ORGANISM: Homo Sapiens
<220> FEATURE:
<221> NAME/KEY: allele
<222> LOCATION: 21,41
<223> OTHER INFORMATION: n can be a, c, g, or t

<400> SEQUENCE: 146 aggggtaga ttttaaaaat ncatgttaat gttatttact n            41

<210> SEQ ID NO 147
<211> LENGTH: 41
<212> TYPE: DNA
<213> ORGANISM: Homo Sapiens
<220> FEATURE:
<221> NAME/KEY: allele
<222> LOCATION: 21,41
<223> OTHER INFORMATION: n can be a, c, g, or t

<400> SEQUENCE: 147 aggggtaga ttttaaaaat ncatgttaat gttatttact n            41

<210> SEQ ID NO 148
<211> LENGTH: 41
<212> TYPE: DNA
<213> ORGANISM: Homo Sapiens
<220> FEATURE:
<221> NAME/KEY: allele
<222> LOCATION: 41
<223> OTHER INFORMATION: n can be a, c, g, or t

<400> SEQUENCE: 148
aggtgtaaga ttttaaaaat acatgttaat gttatttact n           41

<210> SEQ ID NO 149
<211> LENGTH: 41
<212> TYPE: DNA
<213> ORGANISM: Homo Sapiens
<220> FEATURE:
<221> NAME/KEY: allele
<222> LOCATION: 8,41
<223> OTHER INFORMATION: n can be a, c, g, or t

<400> SEQUENCE: 149
aggggtanga tttcaaaaat acatgttaat gttatttact n           41

<210> SEQ ID NO 150
<211> LENGTH: 41
<212> TYPE: DNA
<213> ORGANISM: Homo Sapiens
<220> FEATURE:
<221> NAME/KEY: allele
<222> LOCATION: 8,41
<223> OTHER INFORMATION: n can be a, c, g, or t

<400> SEQUENCE: 150
aggggtanga ttttaaaaat acatgttaat gttatttact n           41

<210> SEQ ID NO 151
<211> LENGTH: 41
<212> TYPE: DNA
<213> ORGANISM: Homo Sapiens
<220> FEATURE:
<221> NAME/KEY: allele
<222> LOCATION: 41
<223> OTHER INFORMATION: n can be a, c, g, or t
```

```
<400> SEQUENCE: 151 agggtaaga ttttaaaaat acatgttaat gttatttact n                          41

<210> SEQ ID NO 152
<211> LENGTH: 41
<212> TYPE: DNA
<213> ORGANISM: Homo Sapiens
<220> FEATURE:
<221> NAME/KEY: allele
<222> LOCATION: 41
<223> OTHER INFORMATION: n can be a, c, g, or t

<400> SEQUENCE: 152 agggtaaga ttttaaaaat acatgttaat gttatttact n                          41

<210> SEQ ID NO 153
<211> LENGTH: 15
<212> TYPE: DNA
<213> ORGANISM: Homo Sapiens

<400> SEQUENCE: 153
tttatctgac tggag                                                      15

<210> SEQ ID NO 154
<211> LENGTH: 15
<212> TYPE: DNA
<213> ORGANISM: Homo Sapiens

<400> SEQUENCE: 154
tttatctgac tggag                                                      15

<210> SEQ ID NO 155
<211> LENGTH: 15
<212> TYPE: DNA
<213> ORGANISM: Homo Sapiens

<400> SEQUENCE: 155
tttatctcac tggag                                                      15

<210> SEQ ID NO 156
<211> LENGTH: 401
<212> TYPE: DNA
<213> ORGANISM: Homo Sapiens

<400> SEQUENCE: 156
attatgctcg attatgctcg attatgctcg attatgctcg attatgctcg attatgctcg     60
attatgctcg attatgctcg attatgctcg attatgctcg attatgctcg attatgctcg    120
attatgctcg attatgctcg attatgctcg attatgctcg attatgctcg attatgctcg    180
attatgctcg attatgctcg sattatgctc gattatgctc gattatgctc gattatgctc    240
gattatgctc gattatgctc gattatgctc gattatgctc gattatgctc gattatgctc    300
gattatgctc gattatgctc gattatgctc gattatgctc gattatgctc gattatgctc    360
gattatgctc gattatgctc gattatgctc gattatgctc g                        401

<210> SEQ ID NO 157
<211> LENGTH: 401
<212> TYPE: DNA
<213> ORGANISM: Homo Sapiens

<400> SEQUENCE: 157
```

```
yttatgctcg attatgctcg attatgctcg attatgctcg attatgctcg attatgctcg        60
attatgctcg rttatgctcg attatgctcg attatgctcg attatgctcg attatgctcg       120
attatgctcg attatgctcg attatgctcg attatgctcg attatgctcg attatgctcg       180
attatgctcg attatgctcg sattatgctc gatmatgctc gattatgctc gattatgctc       240
gattatgctc gattatgctc gattatgctc gattatgctc gattatgctc gattatgctc       300
gattatgctc gattatgctc gattatgctc gattatgctc gattatgctc gattatgctc       360
gattatgctc gattatgctc gattatgctc gattatgctc g                           401
```

<210> SEQ ID NO 158
<211> LENGTH: 11
<212> TYPE: DNA
<213> ORGANISM: Homo Sapiens
<220> FEATURE:
<221> NAME/KEY: allele
<222> LOCATION: 2
<223> OTHER INFORMATION: n can be a, c, g, or t

<400> SEQUENCE: 158

```
cntctgagtt a                                                             11
```

<210> SEQ ID NO 159
<211> LENGTH: 11
<212> TYPE: DNA
<213> ORGANISM: Homo Sapiens
<220> FEATURE:
<221> NAME/KEY: allele
<222> LOCATION: 2
<223> OTHER INFORMATION: n can be a, c, g, or t

<400> SEQUENCE: 159

```
cntctgagtt a                                                             11
```

<210> SEQ ID NO 160
<211> LENGTH: 11
<212> TYPE: DNA
<213> ORGANISM: Homo Sapiens
<220> FEATURE:
<221> NAME/KEY: allele
<222> LOCATION: 2
<223> OTHER INFORMATION: n can be a, c, g, or t

<400> SEQUENCE: 160

```
cntttgagtt a                                                             11
```

<210> SEQ ID NO 161
<211> LENGTH: 11
<212> TYPE: DNA
<213> ORGANISM: Homo Sapiens
<220> FEATURE:
<221> NAME/KEY: allele
<222> LOCATION: 2
<223> OTHER INFORMATION: n can be a, c, g, or t

<400> SEQUENCE: 161

```
cntctgagtt a                                                             11
```

<210> SEQ ID NO 162
<211> LENGTH: 11
<212> TYPE: DNA
<213> ORGANISM: Homo Sapiens
<220> FEATURE:
<221> NAME/KEY: allele
<222> LOCATION: 2
<223> OTHER INFORMATION: n can be a, c, g, or t

```
<400> SEQUENCE: 162
cntttgagtt a                                                            11

<210> SEQ ID NO 163
<211> LENGTH: 11
<212> TYPE: DNA
<213> ORGANISM: Homo Sapiens
<220> FEATURE:
<221> NAME/KEY: allele
<222> LOCATION: 2
<223> OTHER INFORMATION: n can be a, c, g, or t

<400> SEQUENCE: 163
cntctgagtt a                                                            11

<210> SEQ ID NO 164
<211> LENGTH: 11
<212> TYPE: DNA
<213> ORGANISM: Homo Sapiens
<220> FEATURE:
<221> NAME/KEY: allele
<222> LOCATION: 2
<223> OTHER INFORMATION: n can be a, c, g, or t

<400> SEQUENCE: 164
cntctgagtt a                                                            11

<210> SEQ ID NO 165
<211> LENGTH: 11
<212> TYPE: DNA
<213> ORGANISM: Homo Sapiens
<220> FEATURE:
<221> NAME/KEY: allele
<222> LOCATION: 2
<223> OTHER INFORMATION: n can be a, c, g, or t

<400> SEQUENCE: 165
cntctgagtt a                                                            11

<210> SEQ ID NO 166
<211> LENGTH: 11
<212> TYPE: DNA
<213> ORGANISM: Homo Sapiens
<220> FEATURE:
<221> NAME/KEY: allele
<222> LOCATION: 2
<223> OTHER INFORMATION: n can be a, c, g, or t

<400> SEQUENCE: 166
cntctgagtt a                                                            11

<210> SEQ ID NO 167
<211> LENGTH: 11
<212> TYPE: DNA
<213> ORGANISM: Homo Sapiens
<220> FEATURE:
<221> NAME/KEY: allele
<222> LOCATION: 2
<223> OTHER INFORMATION: n can be a, c, g, or t

<400> SEQUENCE: 167
cntctgagtt a                                                            11

<210> SEQ ID NO 168
<211> LENGTH: 11
<212> TYPE: DNA
```

```
<213> ORGANISM: Homo Sapiens
<220> FEATURE:
<221> NAME/KEY: allele
<222> LOCATION: 2
<223> OTHER INFORMATION: n can be a, c, g, or t

<400> SEQUENCE: 168
cntttgagtt a                                                              11

<210> SEQ ID NO 169
<211> LENGTH: 11
<212> TYPE: DNA
<213> ORGANISM: Homo Sapiens
<220> FEATURE:
<221> NAME/KEY: allele
<222> LOCATION: 2
<223> OTHER INFORMATION: n can be a, c, g, or t

<400> SEQUENCE: 169
cntctgagtt a                                                              11

<210> SEQ ID NO 170
<211> LENGTH: 11
<212> TYPE: DNA
<213> ORGANISM: Homo Sapiens
<220> FEATURE:
<221> NAME/KEY: allele
<222> LOCATION: 2
<223> OTHER INFORMATION: n can be a, c, g, or t

<400> SEQUENCE: 170
cntctgagtt a                                                              11

<210> SEQ ID NO 171
<211> LENGTH: 11
<212> TYPE: DNA
<213> ORGANISM: Homo Sapiens
<220> FEATURE:
<221> NAME/KEY: allele
<222> LOCATION: 2
<223> OTHER INFORMATION: n can be a, c, g, or t

<400> SEQUENCE: 171
cntctgagtt a                                                              11

<210> SEQ ID NO 172
<211> LENGTH: 11
<212> TYPE: DNA
<213> ORGANISM: Homo Sapiens
<220> FEATURE:
<221> NAME/KEY: allele
<222> LOCATION: 2
<223> OTHER INFORMATION: n can be a, c, g, or t

<400> SEQUENCE: 172
cntctgagtt a                                                              11

<210> SEQ ID NO 173
<211> LENGTH: 11
<212> TYPE: DNA
<213> ORGANISM: Homo Sapiens
<220> FEATURE:
<221> NAME/KEY: allele
<222> LOCATION: 2
<223> OTHER INFORMATION: n can be a, c, g, or t

<400> SEQUENCE: 173
cntttgagtt a                                                              11
```

```
<210> SEQ ID NO 174
<211> LENGTH: 11
<212> TYPE: DNA
<213> ORGANISM: Homo Sapiens
<220> FEATURE:
<221> NAME/KEY: allele
<222> LOCATION: 2
<223> OTHER INFORMATION: n can be a, c, g, or t

<400> SEQUENCE: 174
cntttgagtt a                                                          11

<210> SEQ ID NO 175
<211> LENGTH: 11
<212> TYPE: DNA
<213> ORGANISM: Homo Sapiens
<220> FEATURE:
<221> NAME/KEY: allele
<222> LOCATION: 2
<223> OTHER INFORMATION: n can be a, c, g, or t

<400> SEQUENCE: 175
cntttgagtt a                                                          11

<210> SEQ ID NO 176
<211> LENGTH: 11
<212> TYPE: DNA
<213> ORGANISM: Homo Sapiens

<400> SEQUENCE: 176
cattcgagtt a                                                          11

<210> SEQ ID NO 177
<211> LENGTH: 11
<212> TYPE: DNA
<213> ORGANISM: Homo Sapiens
<220> FEATURE:
<221> NAME/KEY: allele
<222> LOCATION: 4
<223> OTHER INFORMATION: n can be a, c, g, or t

<400> SEQUENCE: 177
catncgagtt a                                                          11

<210> SEQ ID NO 178
<211> LENGTH: 11
<212> TYPE: DNA
<213> ORGANISM: Homo Sapiens
<220> FEATURE:
<221> NAME/KEY: allele
<222> LOCATION: 4
<223> OTHER INFORMATION: n can be a, c, g, or t

<400> SEQUENCE: 178
catncgagtt a                                                          11

<210> SEQ ID NO 179
<211> LENGTH: 11
<212> TYPE: DNA
<213> ORGANISM: Homo Sapiens
<220> FEATURE:
<221> NAME/KEY: allele
<222> LOCATION: 4
<223> OTHER INFORMATION: n can be a, c, g, or t

<400> SEQUENCE: 179
```
catncgagtt a 11

<210> SEQ ID NO 180
<211> LENGTH: 11
<212> TYPE: DNA
<213> ORGANISM: Homo Sapiens
<220> FEATURE:
<221> NAME/KEY: allele
<222> LOCATION: 4
<223> OTHER INFORMATION: n can be a, c, g, or t

<400> SEQUENCE: 180
catncgagtt a 11

<210> SEQ ID NO 181
<211> LENGTH: 11
<212> TYPE: DNA
<213> ORGANISM: Homo Sapiens
<220> FEATURE:
<221> NAME/KEY: allele
<222> LOCATION: 4
<223> OTHER INFORMATION: n can be a, c, g, or t

<400> SEQUENCE: 181
catnagagtt a 11

<210> SEQ ID NO 182
<211> LENGTH: 11
<212> TYPE: DNA
<213> ORGANISM: Homo Sapiens
<220> FEATURE:
<221> NAME/KEY: allele
<222> LOCATION: 1,2
<223> OTHER INFORMATION: n can be a, c, g, or t

<400> SEQUENCE: 182
nnaatagagt a 11

<210> SEQ ID NO 183
<211> LENGTH: 11
<212> TYPE: DNA
<213> ORGANISM: Homo Sapiens
<220> FEATURE:
<221> NAME/KEY: allele
<222> LOCATION: 1,2,3,4,5,6
<223> OTHER INFORMATION: n can be a, c, g, or t

<400> SEQUENCE: 183
nnnnnnggtt a 11

<210> SEQ ID NO 184
<211> LENGTH: 11
<212> TYPE: DNA
<213> ORGANISM: Homo Sapiens
<220> FEATURE:
<221> NAME/KEY: allele
<222> LOCATION: 2
<223> OTHER INFORMATION: n can be a, c, g, or t

<400> SEQUENCE: 184
cntctgagtt a 11

<210> SEQ ID NO 185
<211> LENGTH: 11
<212> TYPE: DNA
<213> ORGANISM: Homo Sapiens
<220> FEATURE:
<221> NAME/KEY: allele

```
<222> LOCATION: 2
<223> OTHER INFORMATION: n can be a, c, g, or t

<400> SEQUENCE: 185
cntctgagtt a                                                              11

<210> SEQ ID NO 186
<211> LENGTH: 11
<212> TYPE: DNA
<213> ORGANISM: Homo Sapiens
<220> FEATURE:
<221> NAME/KEY: allele
<222> LOCATION: 2
<223> OTHER INFORMATION: n can be a, c, g, or t

<400> SEQUENCE: 186
cntctgagtt a                                                              11

<210> SEQ ID NO 187
<211> LENGTH: 11
<212> TYPE: DNA
<213> ORGANISM: Homo Sapiens
<220> FEATURE:
<221> NAME/KEY: allele
<222> LOCATION: 2
<223> OTHER INFORMATION: n can be a, c, g, or t

<400> SEQUENCE: 187
cntctgagtt a                                                              11

<210> SEQ ID NO 188
<211> LENGTH: 11
<212> TYPE: DNA
<213> ORGANISM: Homo Sapiens
<220> FEATURE:
<221> NAME/KEY: allele
<222> LOCATION: 2
<223> OTHER INFORMATION: n can be a, c, g, or t

<400> SEQUENCE: 188
cntctgagtt a                                                              11

<210> SEQ ID NO 189
<211> LENGTH: 11
<212> TYPE: DNA
<213> ORGANISM: Homo Sapiens
<220> FEATURE:
<221> NAME/KEY: allele
<222> LOCATION: 4
<223> OTHER INFORMATION: n can be a, c, g, or t

<400> SEQUENCE: 189
catncgagtt a                                                              11

<210> SEQ ID NO 190
<211> LENGTH: 11
<212> TYPE: DNA
<213> ORGANISM: Homo Sapiens
<220> FEATURE:
<221> NAME/KEY: allele
<222> LOCATION: 2
<223> OTHER INFORMATION: n can be a, c, g, or t

<400> SEQUENCE: 190
cntccgagtt a                                                              11

<210> SEQ ID NO 191
```

```
<211> LENGTH: 11
<212> TYPE: DNA
<213> ORGANISM: Homo Sapiens
<220> FEATURE:
<221> NAME/KEY: allele
<222> LOCATION: 2
<223> OTHER INFORMATION: n can be a, c, g, or t

<400> SEQUENCE: 191
cntccgagtt a                                                            11

<210> SEQ ID NO 192
<211> LENGTH: 11
<212> TYPE: DNA
<213> ORGANISM: Homo Sapiens
<220> FEATURE:
<221> NAME/KEY: allele
<222> LOCATION: 2
<223> OTHER INFORMATION: n can be a, c, g, or t

<400> SEQUENCE: 192
cnttcgagtt a                                                            11

<210> SEQ ID NO 193
<211> LENGTH: 11
<212> TYPE: DNA
<213> ORGANISM: Homo Sapiens
<220> FEATURE:
<221> NAME/KEY: allele
<222> LOCATION: 2
<223> OTHER INFORMATION: n can be a, c, g, or t

<400> SEQUENCE: 193
cntccgagtt a                                                            11

<210> SEQ ID NO 194
<211> LENGTH: 11
<212> TYPE: DNA
<213> ORGANISM: Homo Sapiens
<220> FEATURE:
<221> NAME/KEY: allele
<222> LOCATION: 4
<223> OTHER INFORMATION: n can be a, c, g, or t

<400> SEQUENCE: 194
ctcncgagtt a                                                            11

<210> SEQ ID NO 195
<211> LENGTH: 11
<212> TYPE: DNA
<213> ORGANISM: Homo Sapiens
<220> FEATURE:
<221> NAME/KEY: allele
<222> LOCATION: 4
<223> OTHER INFORMATION: n can be a, c, g, or t

<400> SEQUENCE: 195
ctcncgagtt a                                                            11

<210> SEQ ID NO 196
<211> LENGTH: 11
<212> TYPE: DNA
<213> ORGANISM: Homo Sapiens

<400> SEQUENCE: 196
cattcgagtt a                                                            11
```

```
<210> SEQ ID NO 197
<211> LENGTH: 11
<212> TYPE: DNA
<213> ORGANISM: Homo Sapiens

<400> SEQUENCE: 197
cattcgagtt a                                                          11

<210> SEQ ID NO 198
<211> LENGTH: 11
<212> TYPE: DNA
<213> ORGANISM: Homo Sapiens

<400> SEQUENCE: 198
catccgagtt a                                                          11

<210> SEQ ID NO 199
<211> LENGTH: 11
<212> TYPE: DNA
<213> ORGANISM: Homo Sapiens
<220> FEATURE:
<221> NAME/KEY: allele
<222> LOCATION: 2
<223> OTHER INFORMATION: n can be a, c, g, or t

<400> SEQUENCE: 199
cntccgagtt a                                                          11

<210> SEQ ID NO 200
<211> LENGTH: 11
<212> TYPE: DNA
<213> ORGANISM: Homo Sapiens
<220> FEATURE:
<221> NAME/KEY: allele
<222> LOCATION: 4
<223> OTHER INFORMATION: n can be a, c, g, or t

<400> SEQUENCE: 200
catntgagtt a                                                          11

<210> SEQ ID NO 201
<211> LENGTH: 11
<212> TYPE: DNA
<213> ORGANISM: Homo Sapiens

<400> SEQUENCE: 201
tattcgagtt a                                                          11

<210> SEQ ID NO 202
<211> LENGTH: 11
<212> TYPE: DNA
<213> ORGANISM: Homo Sapiens

<400> SEQUENCE: 202
tcatcgagtt a                                                          11

<210> SEQ ID NO 203
<211> LENGTH: 11
<212> TYPE: DNA
<213> ORGANISM: Homo Sapiens

<400> SEQUENCE: 203
tcttcgagtt a                                                          11

<210> SEQ ID NO 204
```

```
<211> LENGTH: 11
<212> TYPE: DNA
<213> ORGANISM: Homo Sapiens
<220> FEATURE:
<221> NAME/KEY: allele
<222> LOCATION: 4
<223> OTHER INFORMATION: n can be a, c, g, or t

<400> SEQUENCE: 204
catncgagtt a                                                              11

<210> SEQ ID NO 205
<211> LENGTH: 11
<212> TYPE: DNA
<213> ORGANISM: Homo Sapiens

<400> SEQUENCE: 205
tcttcgagtt a                                                              11

<210> SEQ ID NO 206
<211> LENGTH: 11
<212> TYPE: DNA
<213> ORGANISM: Homo Sapiens
<220> FEATURE:
<221> NAME/KEY: allele
<222> LOCATION: 5
<223> OTHER INFORMATION: n can be a, c, g, or t

<400> SEQUENCE: 206
tctcngagtt a                                                              11

<210> SEQ ID NO 207
<211> LENGTH: 11
<212> TYPE: DNA
<213> ORGANISM: Homo Sapiens

<400> SEQUENCE: 207
tctccgagtt a                                                              11

<210> SEQ ID NO 208
<211> LENGTH: 11
<212> TYPE: DNA
<213> ORGANISM: Homo Sapiens
<220> FEATURE:
<221> NAME/KEY: allele
<222> LOCATION: 4
<223> OTHER INFORMATION: n can be a, c, g, or t

<400> SEQUENCE: 208
catncgagtt a                                                              11

<210> SEQ ID NO 209
<211> LENGTH: 11
<212> TYPE: DNA
<213> ORGANISM: Homo Sapiens
<220> FEATURE:
<221> NAME/KEY: allele
<222> LOCATION: 2
<223> OTHER INFORMATION: n can be a, c, g, or t

<400> SEQUENCE: 209
cnttcgagtt a                                                              11

<210> SEQ ID NO 210
<211> LENGTH: 11
<212> TYPE: DNA
<213> ORGANISM: Homo Sapiens
```

-continued

```
<220> FEATURE:
<221> NAME/KEY: allele
<222> LOCATION: 2
<223> OTHER INFORMATION: n can be a, c, g, or t

<400> SEQUENCE: 210
cntccgagtt a                                                              11

<210> SEQ ID NO 211
<211> LENGTH: 11
<212> TYPE: DNA
<213> ORGANISM: Homo Sapiens

<400> SEQUENCE: 211
catccgagtt a                                                              11

<210> SEQ ID NO 212
<211> LENGTH: 11
<212> TYPE: DNA
<213> ORGANISM: Homo Sapiens
<220> FEATURE:
<221> NAME/KEY: allele
<222> LOCATION: 2
<223> OTHER INFORMATION: n can be a, c, g, or t

<400> SEQUENCE: 212
cntccgagtt a                                                              11

<210> SEQ ID NO 213
<211> LENGTH: 11
<212> TYPE: DNA
<213> ORGANISM: Homo Sapiens
<220> FEATURE:
<221> NAME/KEY: allele
<222> LOCATION: 2
<223> OTHER INFORMATION: n can be a, c, g, or t

<400> SEQUENCE: 213
cnttcgagtt a                                                              11

<210> SEQ ID NO 214
<211> LENGTH: 11
<212> TYPE: DNA
<213> ORGANISM: Homo Sapiens
<220> FEATURE:
<221> NAME/KEY: allele
<222> LOCATION: 1,2,10
<223> OTHER INFORMATION: n can be a, c, g, or t

<400> SEQUENCE: 214
nncttgagtn a                                                              11

<210> SEQ ID NO 215
<211> LENGTH: 11
<212> TYPE: DNA
<213> ORGANISM: Homo Sapiens

<400> SEQUENCE: 215
aatccgagtt a                                                              11

<210> SEQ ID NO 216
<211> LENGTH: 11
<212> TYPE: DNA
<213> ORGANISM: Homo Sapiens

<400> SEQUENCE: 216
```

-continued

```
cattcgagtt a                                                         11

<210> SEQ ID NO 217
<211> LENGTH: 11
<212> TYPE: DNA
<213> ORGANISM: Homo Sapiens

<400> SEQUENCE: 217
actccgagtt a                                                         11

<210> SEQ ID NO 218
<211> LENGTH: 11
<212> TYPE: DNA
<213> ORGANISM: Homo Sapiens
<220> FEATURE:
<221> NAME/KEY: allele
<222> LOCATION: 2
<223> OTHER INFORMATION: n can be a, c, g, or t

<400> SEQUENCE: 218
cntccgagtt a                                                         11

<210> SEQ ID NO 219
<211> LENGTH: 11
<212> TYPE: DNA
<213> ORGANISM: Homo Sapiens
<220> FEATURE:
<221> NAME/KEY: allele
<222> LOCATION: 2
<223> OTHER INFORMATION: n can be a, c, g, or t

<400> SEQUENCE: 219
cntccgagtt a                                                         11

<210> SEQ ID NO 220
<211> LENGTH: 200
<212> TYPE: DNA
<213> ORGANISM: Homo Sapiens
<220> FEATURE:
<221> NAME/KEY: allele
<222> LOCATION: 96,120,148,149,150,175
<223> OTHER INFORMATION: n can be a, c, g, or t

<400> SEQUENCE: 220
agttacaatg atataatctg gtcttccatt tttataaagc aggcgtgcat tagactggac     60
ccaagtccat cggttgtttt ttgtaagaag ccgganaaac tatcatgcca ctttctccan   120
tcttaatcac taaaataaaa ttaaawannn attaaattat caaaccccca aatcnaatat   180
agtaaagatt attcctaaaa                                               200

<210> SEQ ID NO 221
<211> LENGTH: 11
<212> TYPE: DNA
<213> ORGANISM: Homo Sapiens

<400> SEQUENCE: 221
acaatcctta a                                                         11

<210> SEQ ID NO 222
<211> LENGTH: 11
<212> TYPE: DNA
<213> ORGANISM: Homo Sapiens

<400> SEQUENCE: 222
acaatcctta a                                                         11
```

<210> SEQ ID NO 223
<211> LENGTH: 11
<212> TYPE: DNA
<213> ORGANISM: Homo Sapiens

<400> SEQUENCE: 223
acaatcctta a                                                           11

<210> SEQ ID NO 224
<211> LENGTH: 11
<212> TYPE: DNA
<213> ORGANISM: Homo Sapiens

<400> SEQUENCE: 224
acaatcctta a                                                           11

<210> SEQ ID NO 225
<211> LENGTH: 11
<212> TYPE: DNA
<213> ORGANISM: Homo Sapiens

<400> SEQUENCE: 225
acaatcctta a                                                           11

<210> SEQ ID NO 226
<211> LENGTH: 11
<212> TYPE: DNA
<213> ORGANISM: Homo Sapiens

<400> SEQUENCE: 226
acaatcctta a                                                           11

<210> SEQ ID NO 227
<211> LENGTH: 11
<212> TYPE: DNA
<213> ORGANISM: Homo Sapiens

<400> SEQUENCE: 227
acaatcctta a                                                           11

<210> SEQ ID NO 228
<211> LENGTH: 11
<212> TYPE: DNA
<213> ORGANISM: Homo Sapiens

<400> SEQUENCE: 228
acaatcctta a                                                           11

<210> SEQ ID NO 229
<211> LENGTH: 11
<212> TYPE: DNA
<213> ORGANISM: Homo Sapiens

<400> SEQUENCE: 229
acaatcctta a                                                           11

<210> SEQ ID NO 230
<211> LENGTH: 11
<212> TYPE: DNA
<213> ORGANISM: Homo Sapiens

<400> SEQUENCE: 230

```
acaatcctta a                                                    11

<210> SEQ ID NO 231
<211> LENGTH: 11
<212> TYPE: DNA
<213> ORGANISM: Homo Sapiens

<400> SEQUENCE: 231
acaatcctta a                                                    11

<210> SEQ ID NO 232
<211> LENGTH: 11
<212> TYPE: DNA
<213> ORGANISM: Homo Sapiens

<400> SEQUENCE: 232
acaatcctta a                                                    11

<210> SEQ ID NO 233
<211> LENGTH: 11
<212> TYPE: DNA
<213> ORGANISM: Homo Sapiens

<400> SEQUENCE: 233
acaatcctta a                                                    11

<210> SEQ ID NO 234
<211> LENGTH: 11
<212> TYPE: DNA
<213> ORGANISM: Homo Sapiens

<400> SEQUENCE: 234
acaatcctta a                                                    11

<210> SEQ ID NO 235
<211> LENGTH: 12
<212> TYPE: DNA
<213> ORGANISM: Homo Sapiens
<220> FEATURE:
<221> NAME/KEY: allele
<222> LOCATION: 9,10,12
<223> OTHER INFORMATION: n can be a, c, g, or t

<400> SEQUENCE: 235
acaatcctnn an                                                   12

<210> SEQ ID NO 236
<211> LENGTH: 13
<212> TYPE: DNA
<213> ORGANISM: Homo Sapiens
<220> FEATURE:
<221> NAME/KEY: allele
<222> LOCATION: 9,10,11,12,13
<223> OTHER INFORMATION: n can be a, c, g, or t

<400> SEQUENCE: 236
acaaacctnn nnn                                                  13

<210> SEQ ID NO 237
<211> LENGTH: 11
<212> TYPE: DNA
<213> ORGANISM: Homo Sapiens

<400> SEQUENCE: 237
acaaacctta t                                                    11
```

-continued

```
<210> SEQ ID NO 238
<211> LENGTH: 200
<212> TYPE: DNA
<213> ORGANISM: Homo Sapiens

<400> SEQUENCE: 238
ctcaggtccc acagcaacaa tatcattcaa actgcaatta aaacatacac acataatata      60
taaggtgaag gtattgaaca ttacaggatt attaactggc attcctcact gtctattcct     120
aaaatcaaga tgtgggatgg agccttcgtg ctagctataa tggaacacaa ttaatatgaa     180
attagtcctg ccgatacaat                                                 200

<210> SEQ ID NO 239
<211> LENGTH: 36
<212> TYPE: DNA
<213> ORGANISM: Homo Sapiens

<400> SEQUENCE: 239
cttaaagggc gaattcgttt aaacctgcag gactag                                36
```